(12) United States Patent
Pezeshki

(10) Patent No.: US 12,415,098 B2
(45) Date of Patent: *Sep. 16, 2025

(54) REUSABLE PURIFIED AIR BREATHING DEVICE WITH A RETRACTABLE DISPLAY SCREEN

(71) Applicant: BLUE TRON TECHNOLOGIES INC., Pasadena, CA (US)

(72) Inventor: Reza Pezeshki, Pasadena, CA (US)

(73) Assignee: BLUE TRON TECHNOLOGIES INC., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/744,634

(22) Filed: Jun. 16, 2024

(65) Prior Publication Data

US 2024/0342517 A1 Oct. 17, 2024

Related U.S. Application Data

(63) Continuation of application No. 18/519,052, filed on Nov. 26, 2023, now Pat. No. 12,048,855, which is a
(Continued)

(51) Int. Cl.
*A62B 18/02* (2006.01)
*A61L 9/20* (2006.01)
(Continued)

(52) U.S. Cl.
CPC ............ *A62B 18/025* (2013.01); *A61L 9/20* (2013.01); *A62B 9/003* (2013.01); *A62B 18/006* (2013.01);
(Continued)

(58) Field of Classification Search
CPC ....... A61L 9/20; A61L 2209/12; A62B 9/003; A62B 18/006; A62B 23/02; A62B 9/02;
(Continued)

(56) References Cited

U.S. PATENT DOCUMENTS

| | | | |
|---|---|---|---|
| 6,606,114 B1 * | 8/2003 | Gordon | G02B 27/0172 348/64 |
| 6,837,240 B1 * | 1/2005 | Olstad | B63C 11/12 351/158 |

(Continued)

FOREIGN PATENT DOCUMENTS

| CA | 2201961 | 11/2002 |
|---|---|---|
| CN | 109090756 | 12/2018 |

(Continued)

OTHER PUBLICATIONS

English translation for KR 101997813, translated by Espacenet.com, translated on Oct. 16, 2024.*

(Continued)

*Primary Examiner* — Tu A Vo
(74) *Attorney, Agent, or Firm* — Makoui Law, PC; Ali Makoui

(57) ABSTRACT

An air breathing device includes a casing and an air passage cavity encompassed by the casing. The device includes an air intake port and an air discharge port that connect the air passage cavity to the outside of the casing. The device includes a damper (gravity or motorized) that allows the air to flow into the air passage cavity during inhalation through the air intake port. The device includes a damper (gravity or motorized) that allows the air to exit the air passage cavity during exhalation through the air discharge port. The device includes a retractable display screen to display content to the wearer. The device includes a fixed display screen to display images of the mouth of the wearer captured by a camera lens or simulated based on the wearer's captured voice. The device includes UV lights, filters, network connections, camera lenses, speakers, microphones, ear plugs, and heating coils.

23 Claims, 46 Drawing Sheets

Related U.S. Application Data continuation-in-part of application No. PCT/US2022/030764, filed on May 24, 2022, which is a continuation of application No. 17/751,216, filed on May 23, 2022, now Pat. No. 11,684,810.

(60) Provisional application No. 63/315,686, filed on Mar. 2, 2022, provisional application No. 63/192,575, filed on May 25, 2021.

(51) Int. Cl.
| | |
|---|---|
| A62B 9/00 | (2006.01) |
| A62B 18/00 | (2006.01) |
| A62B 18/08 | (2006.01) |
| A62B 18/10 | (2006.01) |
| A62B 23/02 | (2006.01) |
| G06F 3/147 | (2006.01) |

(52) U.S. Cl.
CPC .............. *A62B 18/02* (2013.01); *A62B 18/08* (2013.01); *A62B 18/10* (2013.01); *A62B 23/02* (2013.01); *A61L 2209/111* (2013.01); *A61L 2209/12* (2013.01); *A61L 2209/14* (2013.01); *A61L 2209/15* (2013.01); *G06F 3/147* (2013.01)

(58) Field of Classification Search
CPC ....... A62B 18/10; A62B 18/02; A62B 18/025; G06F 3/147; A61F 9/06; A41D 13/11–1192; A61M 16/06–0694
See application file for complete search history.

(56) References Cited

U.S. PATENT DOCUMENTS

| | | | |
|---|---|---|---|
| 10,335,618 | B2 | 7/2019 | Zhou et al. |
| 10,573,271 | B1 * | 2/2020 | Lvovskiy ............... A42B 3/042 |
| 11,452,793 | B1 | 9/2022 | Fulbrook |
| 11,684,810 | B2 * | 6/2023 | Pezeshki .................... A61L 9/20 128/201.19 |
| 12,048,855 | B1 * | 7/2024 | Pezeshki ............... A62B 18/02 |
| 2004/0003810 | A1 | 1/2004 | Templeton et al. |
| 2004/0216745 | A1 | 11/2004 | Yuen et al. |
| 2007/0089221 | A1 * | 4/2007 | Manzella ............... A61B 90/50 2/456 |
| 2007/0101867 | A1 | 5/2007 | Hunter et al. |
| 2007/0163588 | A1 | 7/2007 | Hebrank et al. |
| 2007/0181129 | A1 * | 8/2007 | Mattinson ............... A62B 18/08 128/206.21 |
| 2007/0253207 | A1 | 11/2007 | Coombs et al. |
| 2008/0023002 | A1 * | 1/2008 | Guelzow ............... A62B 18/08 2/5 |
| 2008/0185001 | A1 * | 8/2008 | McWilliams ........... B63C 11/12 128/204.21 |
| 2009/0133700 | A1 | 5/2009 | Martin et al. |
| 2010/0095439 | A1 * | 4/2010 | Nolan .................... A42B 3/286 2/15 |
| 2010/0307332 | A1 | 12/2010 | Yuen |
| 2012/0042877 | A1 | 2/2012 | Wu et al. |
| 2012/0174922 | A1 | 7/2012 | Virr et al. |
| 2013/0305437 | A1 * | 11/2013 | Weller ............... G02B 27/0179 2/422 |
| 2015/0217145 | A1 * | 8/2015 | Teetzel ................... A62B 9/006 359/885 |
| 2016/0001108 | A1 | 1/2016 | Zhou et al. |
| 2016/0044276 | A1 * | 2/2016 | Shearman ............... A42B 3/042 348/207.1 |
| 2016/0309827 | A1 * | 10/2016 | Dodson ................ A42B 3/0426 |
| 2017/0004895 | A1 * | 1/2017 | Holman ................... A42B 3/30 |
| 2017/0216099 | A1 * | 8/2017 | Saladino ............... A42B 1/247 |
| 2018/0014597 | A1 * | 1/2018 | Cooke .................... A42B 3/042 |
| 2018/0087680 | A1 | 3/2018 | Wilhelm et al. |
| 2018/0264161 | A1 | 9/2018 | Welch |
| 2018/0304107 | A1 * | 10/2018 | Juran ..................... A62B 18/02 |
| 2019/0113751 | A9 * | 4/2019 | Waldern ................ G02B 27/48 |
| 2019/0117820 | A1 | 4/2019 | Dam |
| 2019/0209797 | A1 | 7/2019 | Marsh |
| 2021/0059344 | A1 * | 3/2021 | Ralston .................... G06F 3/013 |
| 2021/0077762 | A1 | 3/2021 | Mauger et al. |
| 2021/0086005 | A1 * | 3/2021 | O'Brien ................... C08L 5/08 |
| 2021/0109354 | A1 * | 4/2021 | Lavoie ................. A62B 18/082 |
| 2021/0113859 | A1 | 4/2021 | Martin |
| 2021/0290793 | A1 | 9/2021 | Tung |
| 2021/0299485 | A1 | 9/2021 | Cubon |
| 2021/0312842 | A1 * | 10/2021 | Tashima ................... A42B 3/30 |
| 2021/0316167 | A1 * | 10/2021 | Keith ..................... A62B 18/08 |
| 2021/0329995 | A1 | 10/2021 | Dietz et al. |
| 2021/0330851 | A1 | 10/2021 | Bell |
| 2021/0338879 | A1 | 11/2021 | Davis et al. |
| 2021/0339058 | A1 | 11/2021 | Conner |
| 2021/0339062 | A1 | 11/2021 | Vasudeva et al. |
| 2021/0368885 | A1 * | 12/2021 | Atri ....................... A42B 3/225 |
| 2022/0054866 | A1 | 2/2022 | Yuen |
| 2022/0062664 | A1 | 3/2022 | Yuen |
| 2022/0080230 | A1 * | 3/2022 | Lamoncha ........... G06V 40/174 |
| 2022/0155597 | A1 * | 5/2022 | Berger .................. G09G 3/002 |
| 2022/0279874 | A1 * | 9/2022 | Bergman ............... G10L 15/26 |
| 2022/0295935 | A1 * | 9/2022 | Hall ..................... G02B 27/017 |
| 2022/0305302 | A1 * | 9/2022 | Hall ..................... A62B 18/006 |
| 2022/0339470 | A1 | 10/2022 | Bowden et al. |

FOREIGN PATENT DOCUMENTS

| | | | | |
|---|---|---|---|---|
| CN | 111772267 | | 10/2020 | |
| CN | 113426038 | | 9/2021 | |
| DE | 10355752 | | 4/2005 | |
| DE | 202021100057 | | 1/2021 | |
| EP | 1059043 | A1 * | 12/2000 | ............. A42B 3/326 |
| EP | 1130448 | A1 * | 9/2001 | ............. A62B 18/08 |
| KR | 101773586 | B1 * | 8/2017 | |
| KR | 101997813 | B1 * | 10/2019 | |
| WO | WO-2020130028 | A1 * | 6/2020 | ............. A42B 3/042 |
| WO | WO-2021241034 | A1 * | 12/2021 | |
| WO | WO 2022/251246 | | 12/2022 | |

OTHER PUBLICATIONS

English translation for WO 2021241034, translated by Espacenet.com, translated on Oct. 17, 2024.*
English translation for EP 1059043, machine translated by espacenet.com, translated on May 16, 2025.*
U.S. Appl. No. 18/519,052, filed Nov. 26, 2023, Pezeshki, Reza.
Portions of prosecution history of U.S. Appl. No. 17/751,216, filed Jun. 27, 2023, Pezeshki, Reza.
Portions of prosecution history of U.S. Appl. No. 18/519,052, filed Jul. 10, 2024, Pezshki, Reza.
Author Unknown, "Half Facepiece Respirator 6000 series, Reusable," 3M Occupational Health and Environmental Safety Division, Jul. 1, 2009, pp. 1-3.
Item posted on Amazon, Author unknown, "Qwork Sand Blasting Hood Cap, Shawl Sandblaster Protective Gear Mask, Anti Dust/Wind Sandblasting Tool Mask, Heat / Cut / Scratch Resistant Neck Protector, White," Retrieved from the Internet: <Qwork, https://www.amazon.com/QWORK-Sandblaster-Protective-Sandblasting-Resistant/dp/B0BCJRFMXJ/ref=sr_1_1_sspa?crid=11AVTW1PIH1M&keywords=qwork+sand+blasting+hood&qid=1706933476&sprefix=qwork+sand+blasting+hoo%2Caps%2C134&sr=8-1-spons&sp_csd=d2lkZ2V0TmFtZT1zcF9hdGY&psc=1>, Aug. 31, 2022, pp. 1-5.
Author unknown, 3M Secure Click Full Facepiece Reusable Respirator Series FF-800, 3M Personal Safety Division, Aug. 2022, pp. 1-5.
Author unknown, "Origine Dinamo Solid Glossy Black with Smoke Visor," Speedoz Limited, Month unknown but before filing date of the present application, 2023, pp. 1-4.
English translation for CN 111772267, listed as item # 5 above.
English translation for CN 113426038, listed as item # 6 above.
English translation of the Abstract for DE 10355752, listed as item # 7 above.

(56) References Cited

OTHER PUBLICATIONS

English translation for DE 202021100057, listed as item # 8 above.
International Search Report and Written Opinion of PCT/US2022/030764, Aug. 15, 2020, Pezeshki, Reza.
Beardsell, Iain, et al., "Get Through MCEM Part A: MCQs," the Royal Society of Medicine Press, Aug. 2009, cover page and p. 33.
Skaria, Shaji D., et al., "Respiratory Source Control Using Surgical Masks With Nanofiber Media," Annals of Occupational Hygiene, vol. 58, No. 6, Apr. 2014, pp. 771-781.
Author unknown, "3M Rugged Comfort Half Facepiece Reusable Respirator 6500 Series," 3M Personal Safety Division, month unknow, 2015, pp. 1-2.
Kim, Do-Kyun, et al., "UVC LED Irradiation Effectively Inactivates Aerosolized Viruses, Bacteria, and Fungi in a Chamber-Type Air Disinfection System," Applied and Environmental Microbiology vol. 84, Issue 17, Sep. 2018, pp. 1-11.
Author unknown, "Using UV Reflective Materials to Maximize Disinfection," Crystal IS, Inc., Jun. 2016, pp. 1-6.
Hebling, Martin, et al., "Ultraviolet irradiation doses for coronavirus inactivation—review and analysis of coronavirus photoinactivation studies," GMS Hygiene and Infection Control 2020, vol. 15, May 2020, pp. 1-8.
Author Unknown, "UV-C LED Product Specifications SMD 3535 Packaged LED," Bolb Inc., V4.0, Mar. 2021, pp. 1-11.
Shimoda, Hiroshi, et al., "Efficacy of 265-nm ultraviolet light in inactivating infectious SARS-CoV-2," Journal of Photochemistry and Photobiology 7 (2021) 100050, Jun. 17, 2021, pp. 1-3.
Author unknown, "How UV-C effect for disinfection?", Stanley Electric Co., LTD., available online at <https:www.stanley.co.jp/e/product/uvc_product/effect/>, on May 6, 2021, as evidenced by the Internet archive Wayback Machine <https://web.archive.org/web/20210506085305/https://www.stanley.co.jp/e/product/uvc_product/effect/>, pp. 1-19.
Author unknown, "Surface disinfection with UV-C technology," Stanley Electric Co., LTD., <https://www.stanley.co.jp/e/product/uvc_product/sterilization/surface.html >, available online on Sep. 20, 2021, as evidenced by the Internet archive Wayback Machine <https://web.archive.org/web/20210920013045/https://www.stanley.co.jp/e/product/uvc_product/sterilization/surface.html>, pp. 1-6.

* cited by examiner

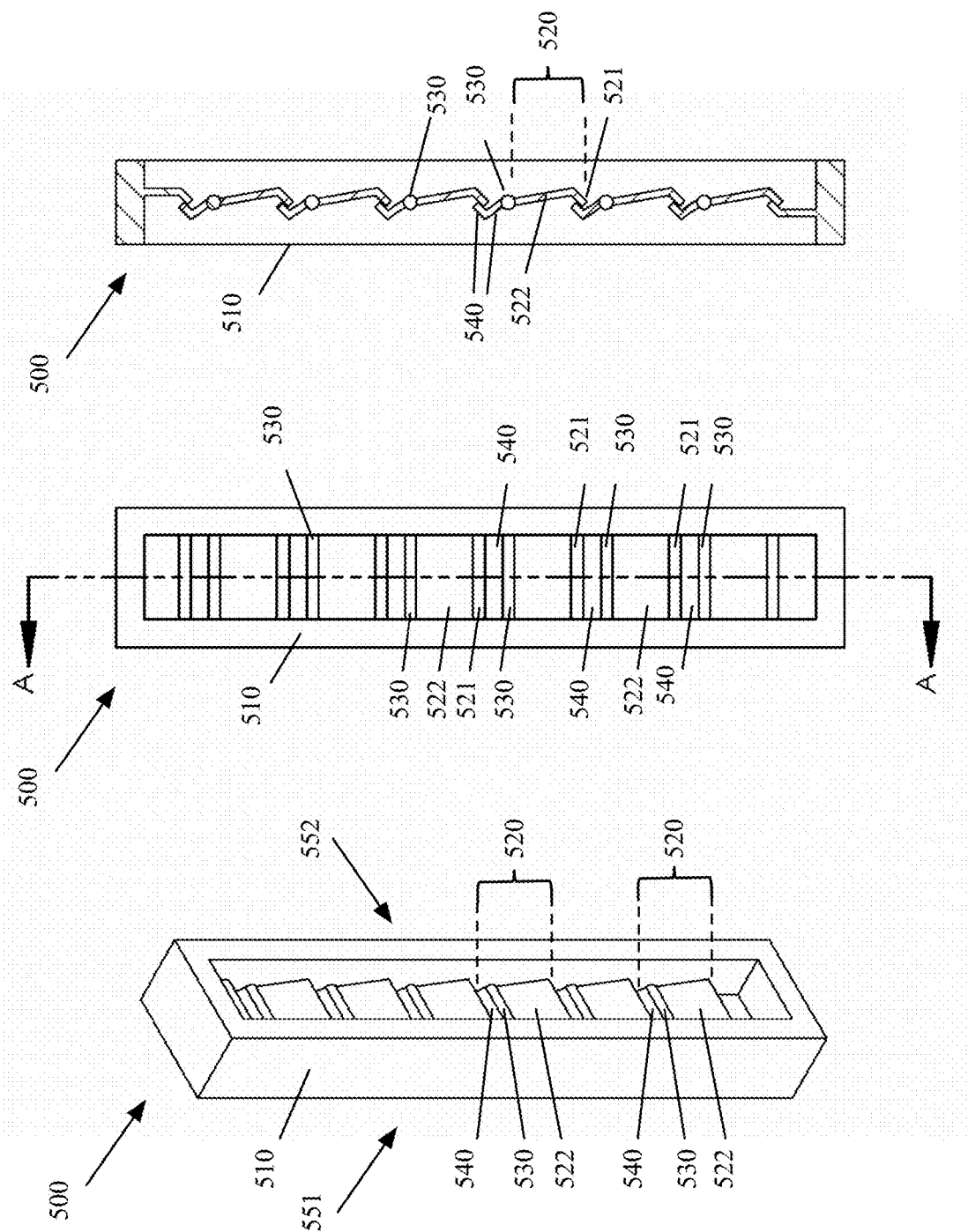

UV light status indicator

REUSABLE PURIFIED AIR BREATHING DEVICE WITH A RETRACTABLE DISPLAY SCREEN

CLAIM OF BENEFIT TO PRIOR APPLICATIONS

This application is a continuation of U.S. patent application Ser. No. 18/519,052, filed Nov. 26, 2023. U.S. patent application Ser. No. 18/519,052 is a continuation-in-part of PCT Application PCT/US2022/030764, filed on May 24, 2022, published as WO 2022/251246. PCT Application PCT/US2022/030764 claims the benefit of U.S. patent application Ser. No. 17/751,216, filed on May 23, 2022, issued as U.S. Pat. No. 11,684,810, U.S. Provisional Patent Application Ser. No. 63/315,686, filed on Mar. 2, 2022, and U.S. Provisional Patent Application Ser. No. 63/192,575, filed on May 25, 2021. The contents of U.S. patent application Ser. No. 18/519,052, PCT Application PCT/US2022/030764, published as WO 2022/251246, U.S. patent application Ser. No. 17/751,216, issued as U.S. Pat. No. 11,684,810, U.S. Provisional Patent Application 63/315,686, and Provisional Patent Application 63/192,575 are hereby incorporated by reference.

BACKGROUND

Respirators are devices that are used to protect the wearers from inhaling hazardous gases, microorganisms, and particulates in the air. Some respirators may be designed to filter fumes, vapors, and dust particles. Some respirators may be designed to filter microorganisms such as viruses, microbes, fungi, etc. The respirators include single use face masks and reusable gas respirators with replaceable filter cartridges. The respirators are used for health and safety reasons by workers in health care, manufacturing, construction, mining, and other industries as well as by private persons when coming into contact with other persons in crowded places.

BRIEF DESCRIPTION OF THE DRAWINGS

The various embodiments of the present reusable purified air breathing device now will be discussed in detail with an emphasis on highlighting the advantageous features. These embodiments depict the novel and non-obvious reusable purified air breathing device shown in the accompanying drawings, which are for illustrative purposes only. These drawings include the following figures, in which like numerals indicate like parts:

FIG. 5A is a side perspective view and FIG. 5B is a front elevation view of an air flow control device or damper, according to various aspects of the present disclosure;

FIG. 5C is a side cross sectional view of the damper of FIGS. 5A and 5B along the line A-A shown in FIG. 5B;

DETAILED DESCRIPTION

Figure 1:
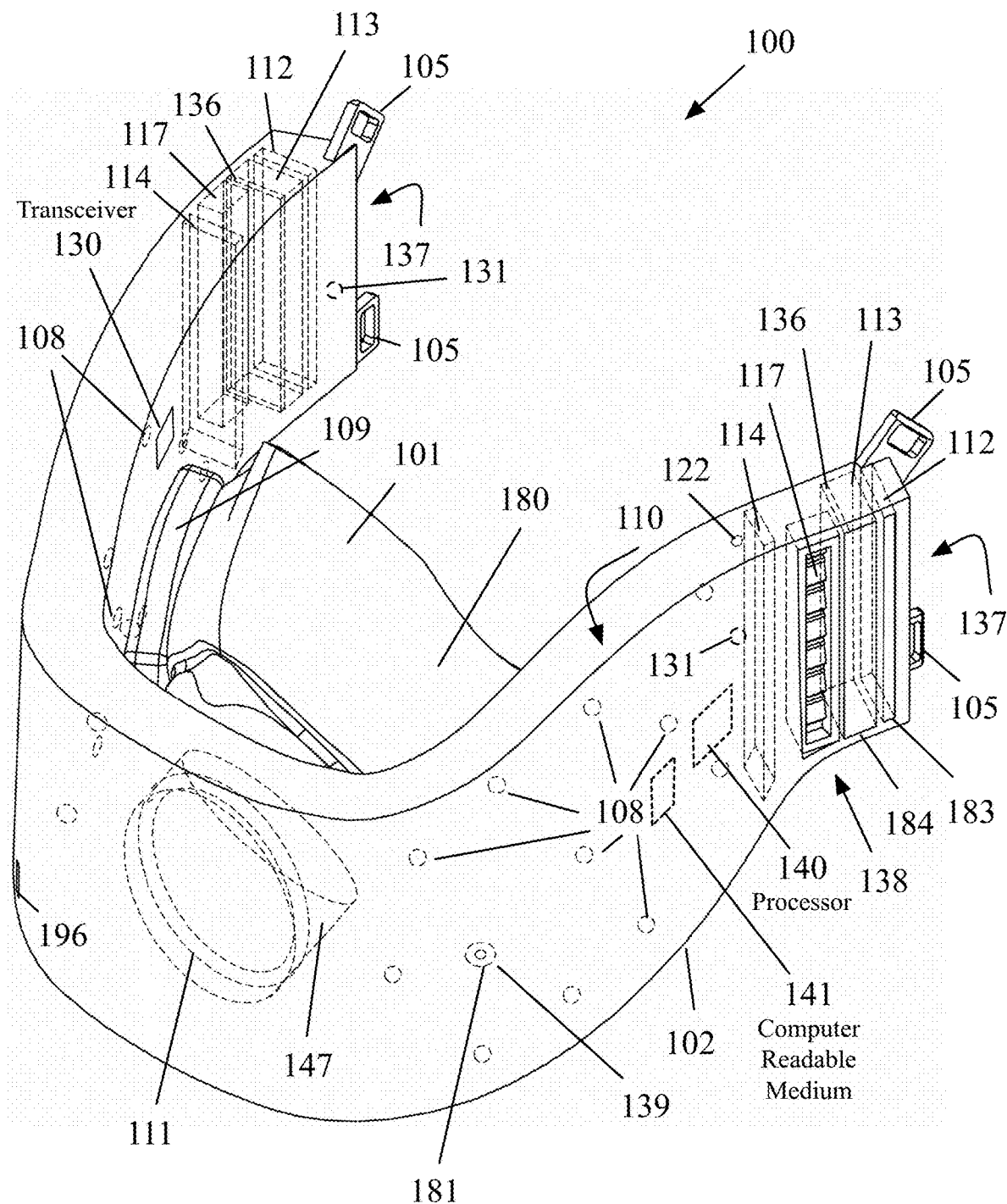
FIG. 1 is a perspective view of a reusable purified air breathing device, according to various aspects of the present disclosure.

One aspect of the present embodiments includes the realization that a long-standing challenge has been to devise a respirator (or face mask) that would sterilize the breathing air from ambient contaminants, such as viruses, bacteria, air particulates, fumes, and volatile compounds. The existing respirators that are designed mostly for industrial applications do not destroy microorganism, such as viruses and bacteria. On the other hand, the respirators that are used to stop microorganism do not filter fumes and volatile compounds.

In addition, the existing industrial respirators are equipped with heavy duty filters with relatively high air pressure drops that would make breathing difficult. High air pressure drop causes air leakage around the perimeter of the existing respirators since air travels through the path of least resistance. Because of the high filter pressure drops, these respirators are required to be tightly fastened against the face to minimize air entry from around the perimeter into the respirators, making the respirators uncomfortable to use. These respirators may make it difficult for users to communicate with other persons while wearing the respirators. The users may not be able to use cellular phones and/or to have access to different networks such as the Internet and/or an intranet.

The present embodiments, as described in detail below, solve the above-mentioned problems by providing a reusable purified air breathing device that removes undesirable air particulates and volatile compounds, and sterilizes the breathing air before entering into the users' body. In addition, the purified air breathing device of the present embodiments sterilizes the breathing air being discharged before leaving the air breathing device back to the environment, preventing the spread of diseases from a sick person to other people.

The air breathing devices of the present embodiments may include a set of dampers (or louvers) that may control the direction of the air into and out of the air breathing device during inhaling and exhaling of the air by the users. The air breathing devices of the present embodiments may include ultraviolet (UV) light sources (or lamps) that may destroy microorganisms such as viruses, bacteria, and fungi. The air breathing devices of the present embodiments may include a heating mechanism to heat the air before the air is inhaled by the users.

The air breathing devices of the present embodiments may include one or more replaceable air filters, such as, particulate filters and/or carbon filters. In some embodiments, an air filter and a carbon filter may be included, or combined, into one replaceable cartridge. The particulate filters may be made of fibrous or porous material, and may be configured to capture particulates such as dust, pollen, mist, fumes, and smoke. The particulate filters may be configured to filter oil based particles and non-oil based particles. The carbon filter may be configured to filter gases through a bed of activated carbon. The carbon filter may remove odors and gaseous pollutants such as volatile organic compounds or ozone.

The air breathing devices of the present embodiments may include network connections, camera lenses, speakers, microphones, ear plugs, etc., to facilitate connecting to different networks and/or communicating with other persons. The air breathing devices of the present embodiments may include one or more display screens to display information to the person who is wearing the air breathing devices and/or to other persons.

The remaining detailed description describes the present embodiments with reference to the drawings. In the drawings, reference numbers label elements of the present embodiments. These reference numbers are reproduced below in connection with the discussion of the corresponding drawing features.

I. Purified Air Breathing Device

Figure 2:
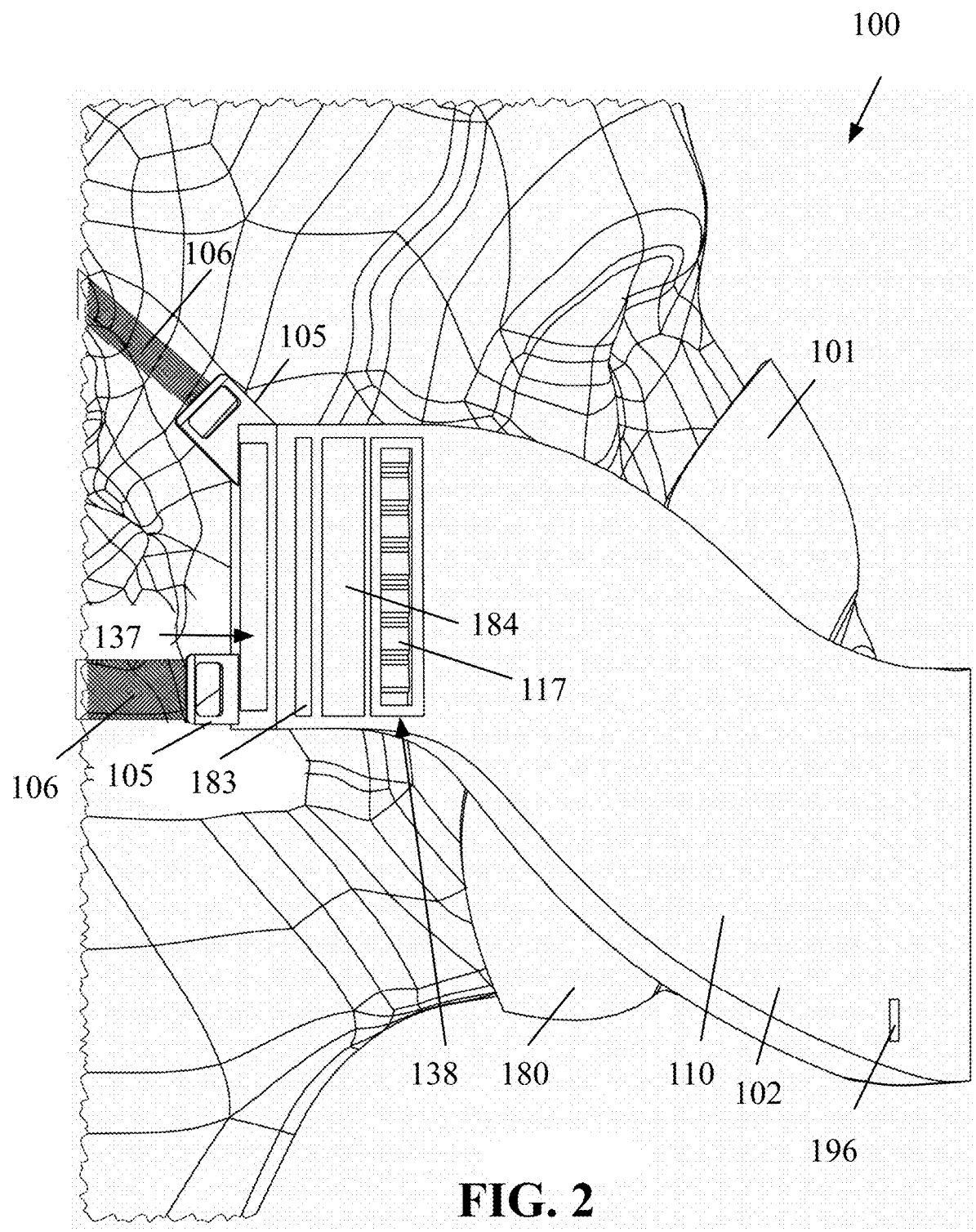
FIG. 2 is a side elevation view.
Figure 3:
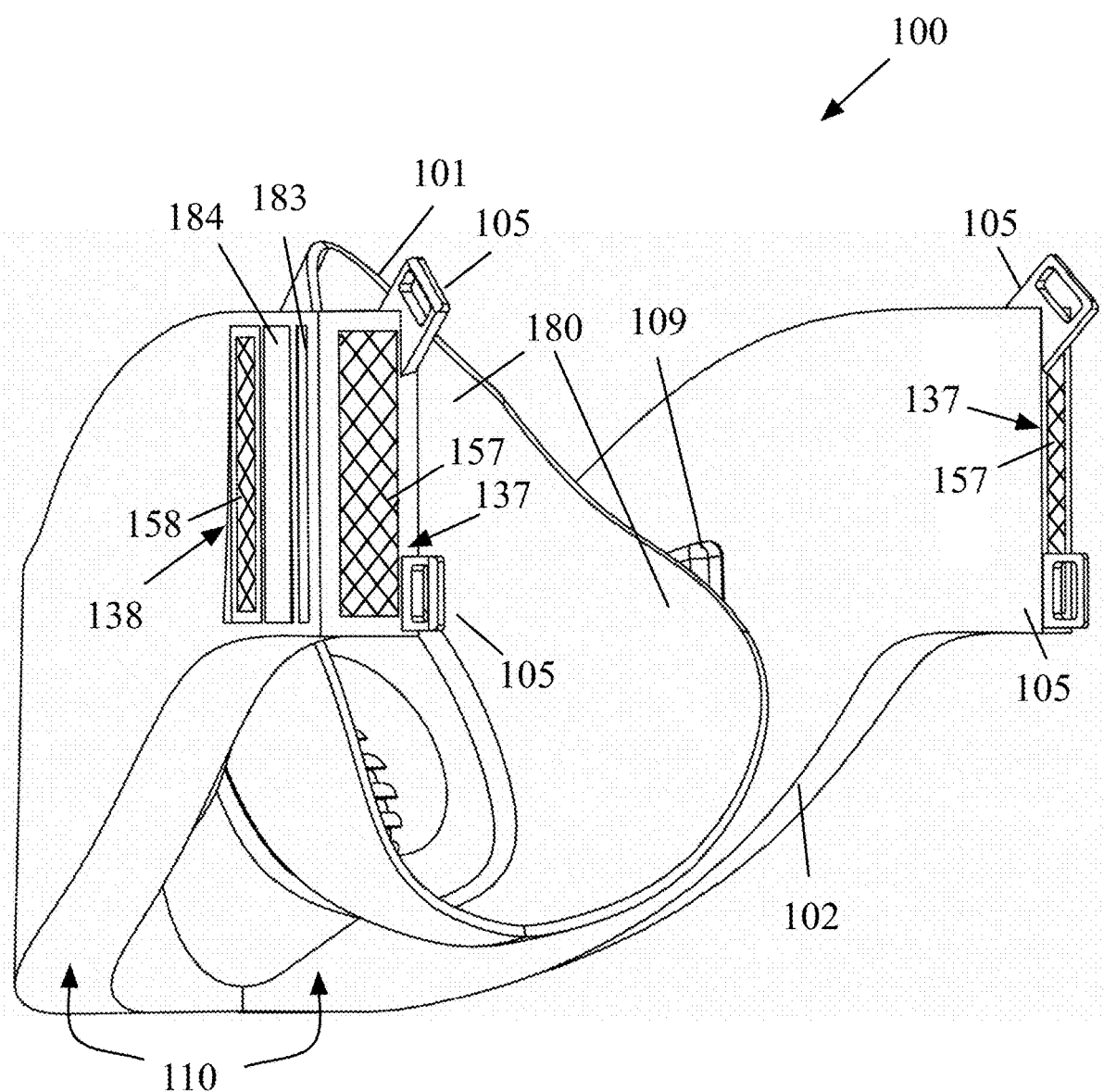
FIG. 3 is a back perspective view.
Figure 4A:
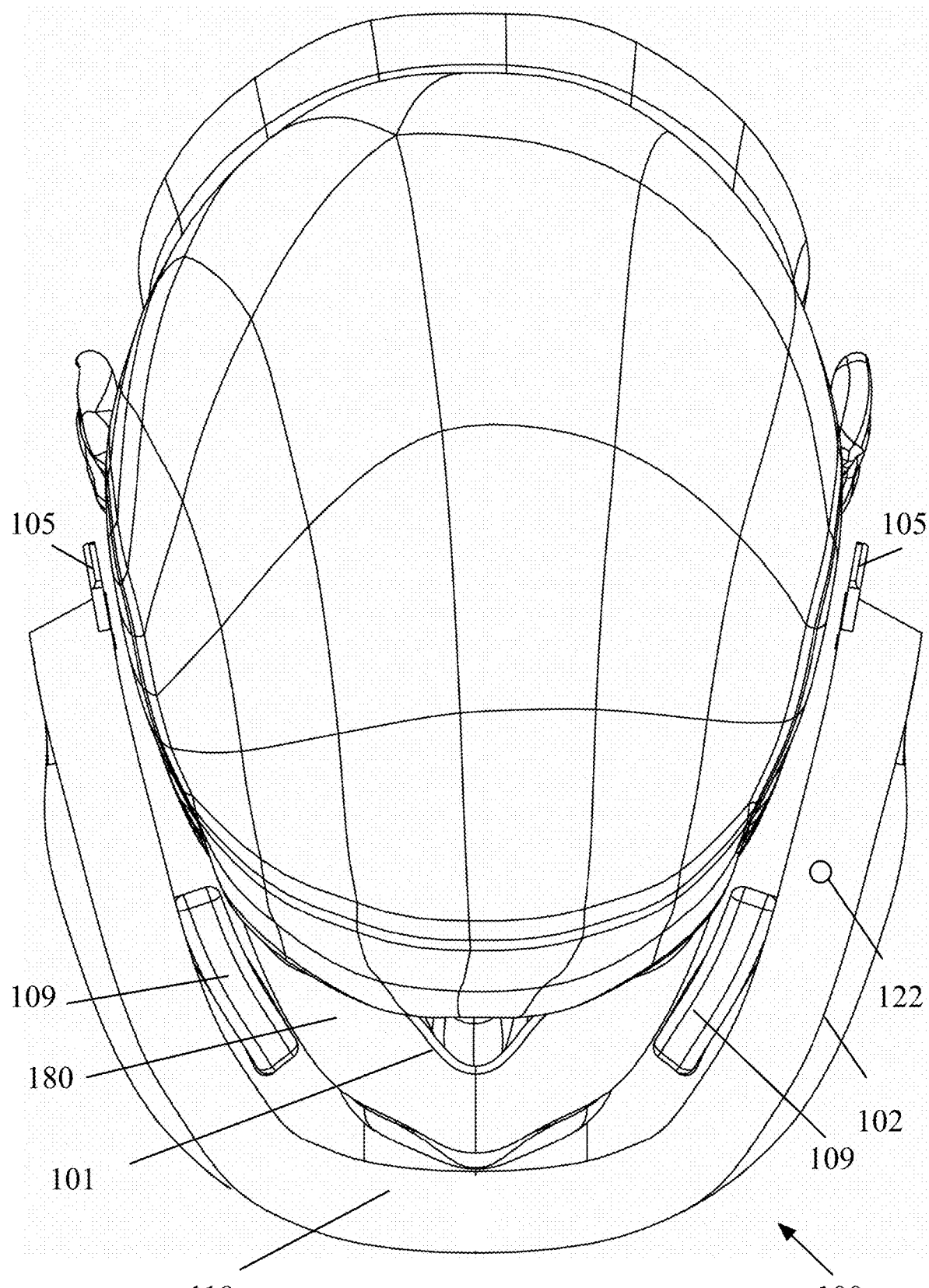
FIG. 4A is a top view.
Figure 4B:
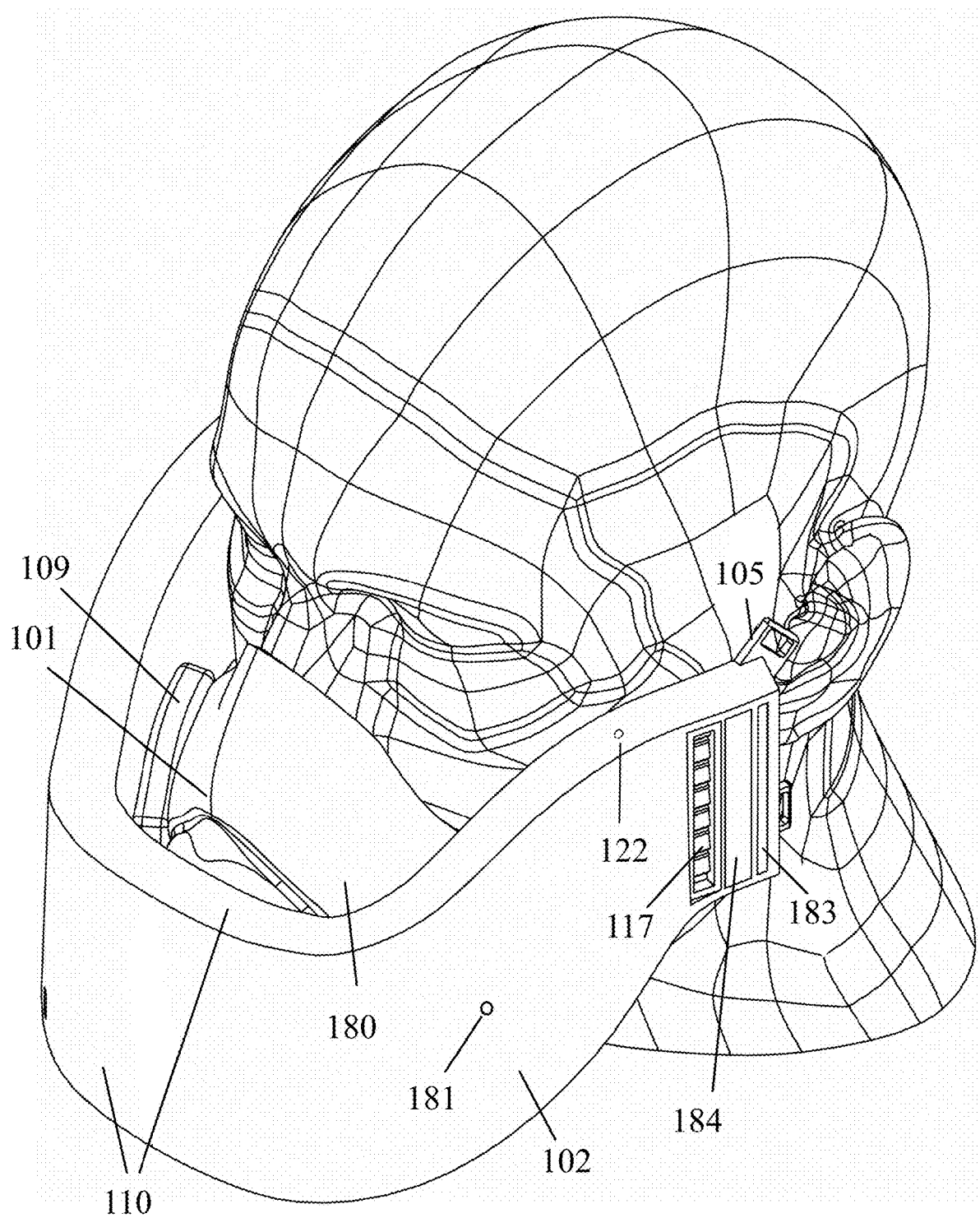
FIG. 4B is a side perspective view.
Figure 4C:
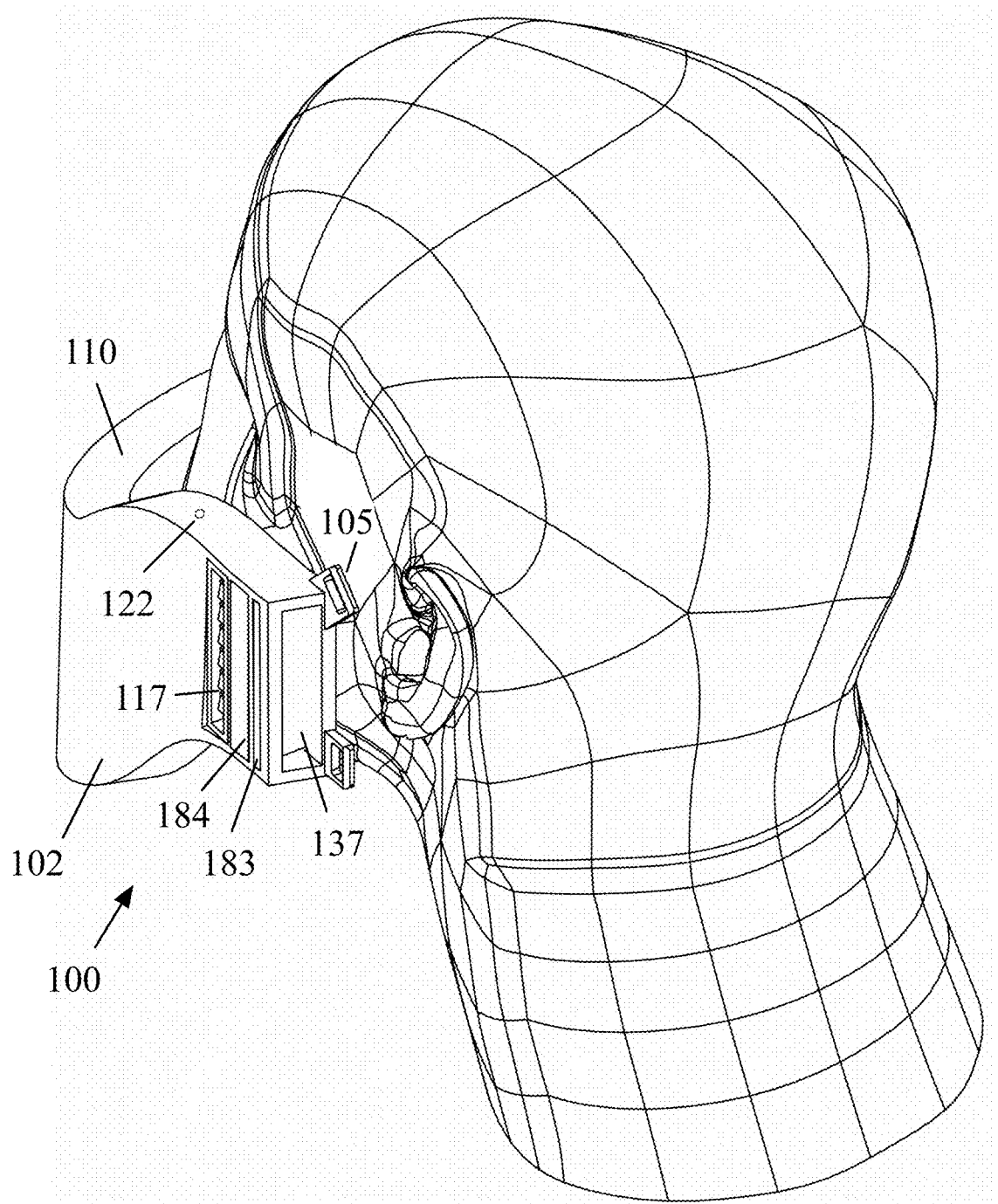
FIG. 4C is a back perspective view.
Figure 4D:
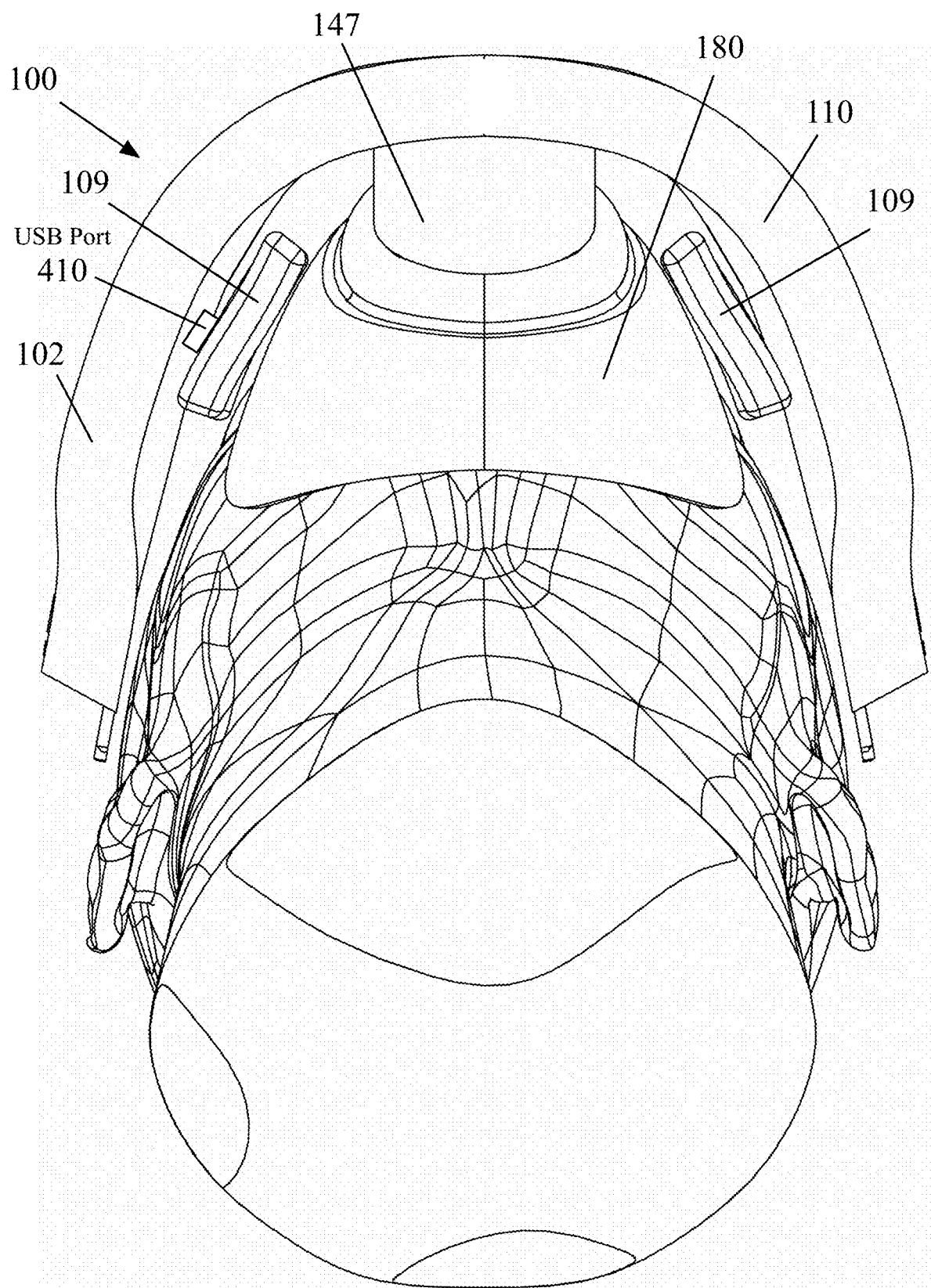
FIG. 4D is a bottom view of the reusable purified air breathing device of FIG. 1.

Some of the present embodiments provide a reusable purified air breathing device. FIG. 1 is a perspective view of a reusable purified air breathing device 100, according to various aspects of the present disclosure. FIG. 2 is a side elevation view, FIG. 3 is a back perspective view, FIG. 4A is a top view, FIG. 4B is a front and side perspective view, FIG. 4C is a back and side perspective view, and FIG. 4D is a bottom view of the reusable purified air breathing device of FIG. 1.

FIGS. 2-4D only show the components of the air breathing device 100 that are visible from the outside of the air breathing device 100. The person depicted in some of the figures in this disclosure is to illustrate how the air breathing device 100 of the present embodiments may be worn by a person (this person is referred to herein as the wearer).

With reference to FIGS. 1 to 4D, the air breathing device 100 may include a facepiece 180, a casing 102, several harness handles 105, a set of harnesses 106 (FIG. 2), one or more UV light sources 108, a UV light status indicator 196, one or more rechargeable batteries 109, a decontamination chamber (or air passage cavity) 110, one or more UVC light isolation screens 111 and 114, one or more air filter cartridges 112, several sets of dampers 113 and 117, a UV Light on/off switch 122, one or more communications transceivers 130 (e.g., one or more wired or wireless transceivers), a processor 140, an air tube 147 for air transfer between the decontamination chamber 110 and the facepiece 180, one or more electric heating coils 136, and an air pressure differential sensor 139.

With further reference to FIGS. 1 to 4D, the air breathing device's casing 102 may be made of a material, such as, for example, and without limitations, hard plastic. The exterior of the casing may be thermally insulated by a layer of insulating material, by injected foam insulation, or by other material and methods. For example, in some embodiments, the body of the casing 102 may include a cavity close to the exterior of the casing 102, and foam insulation may be injected into the cavity during the manufacturing of the casing 102. In some embodiments, the exterior of the casing 102 may include a layer of insulating material. In some embodiments, the back side of the air breathing device, which is close to the face of the wearer, may not be insulated to provide thermal comfort to the wearer.

The facepiece 180 may be attached to the wearer's face and chin. The facepiece 180 may include a nose enclosure 101 to enclose the nose of the wearer. The air breathing device 100 may include a lining at the edges of the casing 102, and/or inside the facepiece 180, where the casing 102, and/or the facepiece 180 come into contact with the wearer's face. The lining may be made of soft and flexible material such as, for example, and without limitations, silicone, to make the air breathing device 100 airtight and to protect the wearer's face against the rigid casing material.

The casing 102, the lining, and/or the facepiece 180, in some embodiments, may be made in different sizes to match the faces of different persons. For example, and without limitations, the air breathing device 100 may be made in different sizes, such as, extra small, small, medium, large, extra-large, etc. Each size may come with an appropriate size of casing, lining, and/or nose enclosure.

The lining, in some embodiments, may be customized to fit an individual person's face contours. For example, an external computer system at a point of sale, or at an establishment, such as, for example, and without limitations, a hospital, a factory, etc., may be used to measure an individual person's face contours. Next, the computer's processor may identify an air breathing device size that best fits the individual person's face. The computer's processor may then select one of many different sizes of casing, facepieces, and linings for the selected air breathing device size to further fit the air breathing device to the person's face.

It should be noted that the casing 102 in different embodiments may have different shapes and/or different contours. For example, in FIG. 1, the front and/or the sides of the casing 102 may be curved towards the back (towards the face of the wearer) in order to facilitate the lining to better fit to the contours of a person's face. In other embodiments, the front and the four sides of the casing 102 may be formed in different shapes. Accordingly, the present embodiments are not limited to the exemplary shape of the casing 102 shown in FIG. 1.

The air breathing device 100 may include one or more air intake ports 137. Different embodiments may include different numbers of air intake ports 137, and the air intake port(s) 137 may be positioned on different locations on the casing 102. The embodiment of FIGS. 1 to 4D include two air intake ports 137 on the back side of the casing 102, as shown in FIG. 3.

The air breathing device 100 may include one or more air discharge ports 138. Different embodiments may include different numbers of air discharge ports 138, and the air discharge port(s) 138 may be positioned on different locations on the casing 102. The embodiment of FIGS. 1 to 4D include two air discharge ports 138 on the two sides of the casing 102 (only one air discharge ports 138 is shown in the perspective view of FIG. 1).

The air intake ports 137 may be covered by perforated protective screens 157 to prevent the entry of large particles and debris into the air filter cartridges 112 and the intake dampers 113. The air discharge ports 138 may be covered by perforated protective screens 158 to prevent the entry of large particles and debris into the discharge dampers 117. The perforated protective screens 157 and 158 are only shown in FIG. 3. The perforated protective screens are not shown in other figures to maintain clarity.

The air breathing device 100 may include several sets of dampers 113 and 117. The damper 113 and 117 are used to regulate the air flow into, and out of, the air breathing device 100, respectively. The dampers 113 and 117, in some embodiments, may be gravity dampers. In other embodiments, the dampers may be motorized dampers, controlled based on the air pressure differential sensor 139 readings, to regulate the motorized dampers.

The air breathing device 100, in some embodiments (for example in any embodiments described herein with reference to FIGS. 1-32), may include the processor 140 and the computer readable media 141. The computer readable media 141 may include different types of memory units, such as, read-only-memory, volatile read-and-write memory, and/or non-volatile read-and-write memory. The read-only-memory may store static data and instructions that are needed by the processor 140. The non-volatile read-and-write memory may store instructions and data even when the power to the non-volatile memory is off. Some embodiments may use a small mass-storage device (such as a magnetic or optical disk and its corresponding disk drive) as the non-volatile read-and-write memory.

The volatile read-and-write memory device may be random access memory and may be used as system memory. The system memory may store some of the instructions and data that the processor needs at runtime. In some embodiments, the processes of the present embodiments may be stored in the system memory, the non-volatile memory, and/or the read-only memory. From these various memory units, the processor 140 may retrieve instructions to execute, and data to process, in order to execute and control different electronic components of the air breathing device 100 and to perform the processes of some embodiments. As used in this specification, the terms computer readable medium and computer readable media are entirely restricted to non-transitory, tangible, physical objects that store information in a form that is readable by a computer. These terms exclude any wireless signals, wired download signals, and any other ephemeral or transitory signals.

FIG. 5A is a side perspective view, and FIG. 5B is a front elevation view of an air flow control device or damper 500, according to various aspects of the present disclosure. FIG. 5C is a side cross sectional view of the damper 500 along the line A-A shown in FIG. 5B. With reference to FIGS. 5A-5C, the damper 500 may be any of the intake dampers 113 or the discharge dampers 117 described above.

The damper 500, also referred to as a gravity damper or gravity louver, may include a casing 510 and one or more blades 520. Each blade 520 may include one or more plates. In the depicted embodiment, each blade 520 includes two plates 521 and 522. The plates 521 and 522 of each blade 520 may move across a hinge 530 in order to tightly attach the plate 520 to an adjacent plate. Each blade 520 may be connected to the casing 510 by a hinge 530. The plates 521 and 522 are always at a fixed angle with respect to each other and rotate together around the corresponding hinge 530. Only some of the blades, plates, and hinges are labeled to maintain clarity. Some embodiments may include a backplate 540 next to each hinge 530 to further ensure the tight attachment of the adjacent blades when the blades are closed to block the passage of the air.

In absence of airflow, the blades 520 of the gravity damper are in close position. The blades 520 of the gravity damper 500 are configured to open or close in response to air pressure difference between the outside and inside of the air breathing device 100. The physical arrangement of the intake dampers 113 of the entry port 137 and discharge dampers 117 of the discharge port 138 (FIGS. 5A, 5B, and 5C) are identical and only differ in their orientation in relation to each other. The orientation of the intake dampers 113 are opposite to the discharge dampers 117.

The blades 520 of the intake damper 113 are hinged toward the inside of the casing 102 of the air breathing device 100 so that the air can only enter into the casing 102 in response to the air pressure inside the decontamination chamber 110 being less than the air pressure outside the casing 102 (e.g., during the air inhalation when the inside air pressure is less than the outside air pressure). During the air inhalation, the blades of discharge dampers 117 are in close position and do not allow the air to enter into, or exit from, the air breathing device 100 through the air discharge port 138.

The blades 520 of the discharge damper 117 are hinged toward the outside of the casing 102 of the air breathing device 100 so that the air can only leave out of the casing 102 in response to the air pressure inside the decontamination chamber 110 being more than the air pressure outside the casing 102 (e.g., during the exhalation when the inside air pressure is more than the outside air pressure). During the air exhalation, the blades of intake dampers 113 are in close position and do not allow the air to enter into, or exit from, the air breathing device 100 through the air intake port 137.

The dampers 113 and 117 are, therefore, configured, such that the breathing air may only enter into the air breathing device 100 through air intake ports 137, and may leave the air breathing device 100 through the discharge port 138. The dampers 113 and 117 provide the technical advantage of controlling the path of breathing air in response to air pressure difference between the inside of the decontamination chamber 110 and the outside of the casing 102 when the air is being inhaled and exhaled.

The intake dampers 113 may be accessed (e.g., for service or replacement) by removing the access cover 184 that provides access to both the air intake dampers 113 and the electric heating coil 136. The discharge dampers 117 may be accessed (e.g., for service or replacement) through the discharge port 138.

Figure 6:
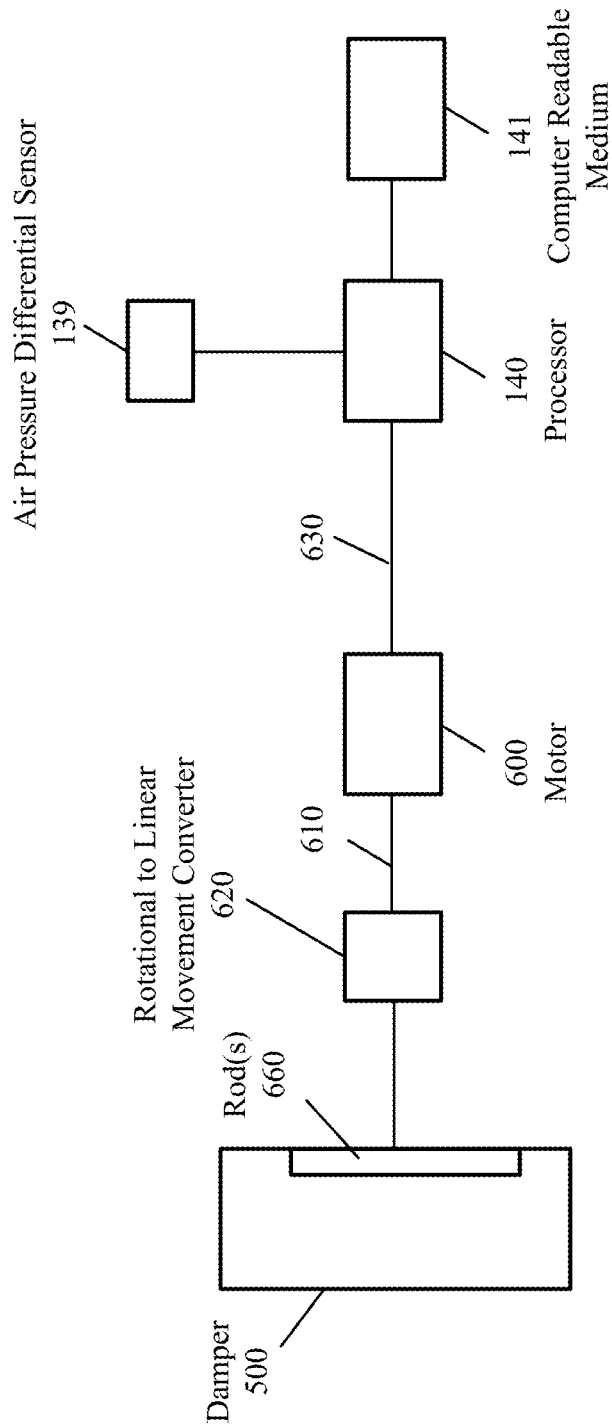
FIG. 6 is an electromechanical functional block diagram illustrating the control of the motorized dampers, according to various aspects of the present disclosure.

Some embodiments may use motorized dampers. In these embodiments, the flow of the breathing air is controlled through the use of motorized dampers. FIG. 6 is an electro-mechanical functional block diagram illustrating the control of the motorized dampers, according to various aspects of the present disclosure. The motorized dampers 500 may be controlled by the processor 140 of the air breathing device based on the measurements made by the air pressure differential sensor 139.

With reference to FIG. 1, the air pressure differential sensor 139 may be located on the surface of the casing 102 of the air breathing device 100. The air pressure differential sensor 139 measures, through the opening 181 of the casing 102, the difference between the air pressure inside and outside of the casing 102.

With reference to FIG. 6, the motorized damper 500 may have similar components as the gravity damper of FIGS. 5A-5C. With reference to FIG. 6, the motorized damper 500 may be any of the intake dampers 113 or the discharge dampers 117 described above. The hinges 530 (FIGS. 5A-5C) of the damper 500 may be connected to one or more rods 660 that may be connected to the rotating shaft 610 of the motor 600 through a rotational to linear movement converter 620 in some embodiments. In other embodiments, the rods may be moved by a piston-like linear movement. FIG. 6 shows only one damper 500 and one motor 600. It should be understood that some embodiments may use one motor 600 to control all air intake dampers 113 and all air discharge dampers 117, some embodiments may include one motor 600 per damper 113 or 117, some embodiments may include one motor 600 to control all air intake dampers 113 and another motor 600 to control all air discharge dampers 117, or one motor 600 to control each group of air intake dampers 113 and air discharge dampers 117 that are close to each (e.g., the air intake dampers 113 and the air discharge dampers 117 that are on the same side of the casing 102).

The processor 140 may receive air pressure differential readings from the air pressure differential sensor 139. The processor 140 may determine whether to open or close the damper 500 based on the air pressure differential readings and whether the damper 500 is an air intake damper 113 or a discharge damper 117.

For example, when the air pressure differential readings indicates that the air pressure inside the casing 102 of the air breathing device is larger than the air pressure outside of the casing 102 by a first threshold, the processor 140 may send one or more signals (e.g., through a wired or wireless link 630) to the motor 600 to close the blades 520 of the air intake dampers 113 and open the blades 520 of the discharge dampers 117 to allow the air that is exhaled by the wearer to exit the casing 102. When the air pressure differential readings indicates that the air pressure inside the casing 102 of the air breathing device is lower than the air pressure outside of the casing 102 by a second threshold, the processor 140 may send one or more signals to the motor 600 to open the blades 520 of the air intake dampers 113 and close the blades 520 of the discharge dampers 117 to allow the outside air to enter the casing 102.

The motor 600 may receive the signals from the processor and in response to the signals may rotate the rotating shaft 610. The rotational to linear movement converter 620 may convert the rotational movements of the shaft 620 to linear movements and may move the rod(s) that control the position of the blades 520 (FIGS. 5A-5C). In response, the hinges 530 may rotate the blades 520 to open or close the blades.

The gravity dampers and the motorized dampers of the air breathing devices of the present embodiments provide the technical advantage of being modular and replaceable. If the gravity dampers and the motorized dampers of the present embodiments are broken or functionally compromised, they may be replaced with new dampers without the need to replace the entire air breathing device.

Figure 4E:
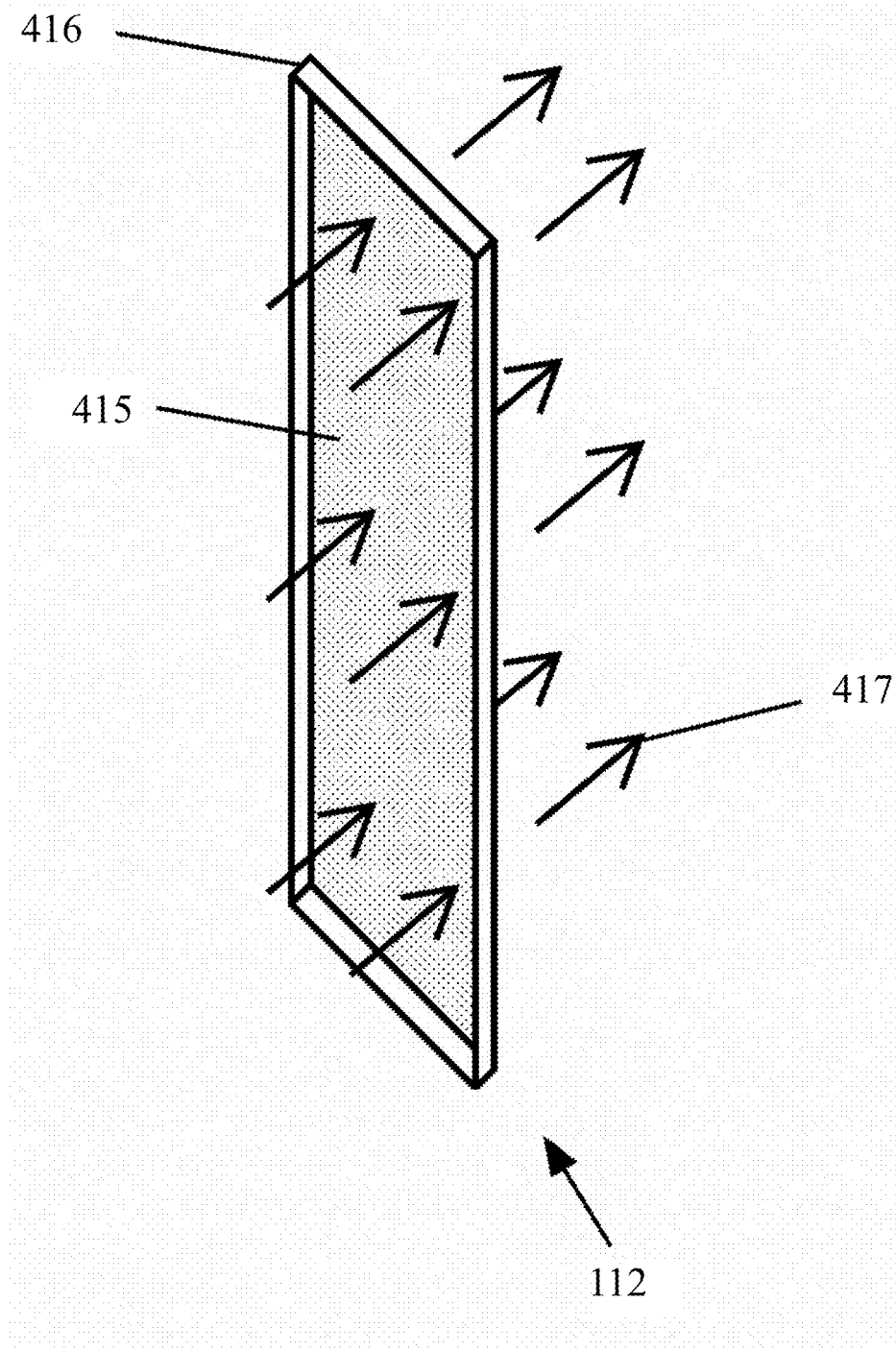
FIG. 4E is a side perspective view of an air filter cartridge, according to various aspects of the present disclosure.

FIG. 4E is a side perspective view of an air filter cartridge, according to various aspects of the present disclosure. With reference to FIGS. 1 to 4E, the air breathing device 100 may include a replaceable air filter cartridge 112 at each air intake port 137. The air filter cartridge 112 may be accessed (e.g., for replacement) through the air filter cartridge cover 183. As shown in FIG. 4E, the air filter cartridge 112 may include one or more filters 415 and a frame 416. The air filter cartridges 112, in some embodiments, may include one or more particulate filter and one or more carbon filters combined into one cartridge. For example, and without limitations, the air filter cartridges 112 may include one layer of carbon filter between two layers of particulate filters. In the perspective of FIG. 4E, one of the air filters (e.g., a particulate filter) is shown. The air filter cartridges 112, in some embodiments, may include only a particulate filter or only a carbon filter.

The particulate filters may be made of fibrous or porous material, and may be configured to capture (e.g., through electrostatically charged fibers, such as, for example, and without limitations, poly-propylene, microfibers, nanofibers, or other material) particulates such as dust, pollen, mist, fumes, and smoke. The particulate filters may be configured to filter oil based particles and non-oil based particles.

The carbon filter may be configured to filter gases through a bed of activated carbon (activated charcoal). The carbon filter may remove odors and gaseous pollutants such as volatile organic compounds or ozone. In addition to, or in lieu of, the air filter cartridges 112 that include both particulate and carbon filters, some embodiments may include individual particulate filters and/or individual carbon filters.

The air filter cartridges 112 of the present embodiments have substantially the same filter surface area as the interior of the air breathing device 100 at the locations where the air filter cartridges are inserted. For example, the filter surface area of the air filter cartridge 112 of the present embodiments may be 80% of more of the area of the interior of the air breathing device 100 at a cross section made at the location where the air filter cartridge is inserted.

The shape of the air filter conforms to the shape of the interior of the cavity 102 of the air breathing device, thereby minimizing the difference in filtration rate at various points of the filter. As such, air filter cartridges of the present embodiments provide the technical advantage of maintaining a uniform air flow direction through the air filter cartridges (e.g., as shown by the arrows 417). In contrast, the air that enters the prior art masks through an air filter immediately goes through a narrow hole before the air enters the interior of the mask. As such, the direction of the air flow through the prior art air filter cartridges is nonuniform, for example, pointed to the center of the air filter cartridge.

The filters of the present embodiments may be configured to suit different applications such as, medical, industrial, and/or personal use. Some of the present embodiments may require the filters to be replaced after a period of time, for example, after several days, several weeks, several months, etc. In some embodiments, the air pressure differential sensor 139 measurements may be used to determine whether the air filters need to be changed. For example, the air filters may need to be changed when the air pressure differential sensor 139 measurements exceed a threshold over a period of time. As described below, some embodiments may include a processor that may provide air filter replacement warnings and/or may control the motorized dampers based on the measurements received from the air pressure differential sensor 139.

Since the prior art respirators rely solely on heavy duty filters to cleanse and disinfect the air, the prior art respirators inherently have high air pressure drops, which makes breathing difficult for the wearers. The breathing air devices of the present embodiments use the UVC light to disinfect the air and kill and/or disable harmful microorganisms and do not rely on heavy duty air filters to disinfect the air. The breathing air devices of the present embodiments that include UVC lights provide the technical advantage of using air filters, such as nanofiber air filters, with relatively low air pressure drop, in conjunction with the cleansing action of the UVC light rays, that make it easier for the wearers to breath than the prior art respirators.

With continued reference to FIGS. 1 to 4C and FIGS. 14 to 17C, the intake ports 137, the replaceable air filter cartridges 112, and the intake dampers 113, in some embodiments, may be designed to be substantially the same physical size to assure a uniform air velocity profile across the filter media. Unlike prior arts, a uniform air velocity profile across the filter media is maintained to result in uniform dust particles, fumes, and vapor loading on the filter media, hence increasing the overall air filtration efficiency. Unlike prior arts, the replaceable cartridge 112 is located inside of the air breathing device 100, and therefore it is protected from environmental conditions like rain and snow.

With further reference to FIGS. 1 to 4D, the air breathing device 100 may include one or more UV light sources 108 (shown as small round circles in FIG. 1) inside the decontamination chamber 110. For clarity, only some of the UV light sources are labeled and/or shown in FIG. 1. The UV rays have sterilization and disinfection effects by destroying the molecular structure of DNA and RNA in microorganisms, such as viruses, bacteria, and fungi, resulting in growth cell death and/or regenerative cell death. The UV rays are divided into A, B, C, and D bands, and the microorganisms disinfection effect is most effective in the C band (UVC) with a wavelength ranging between 200 to 280 nm (nanometers), which may destroy microorganisms' DNA and RNA.

The UV light sources 108, in some embodiments, may be UVC light sources. The UVC light sources 108 may generate UV light with a wavelength of 200 to 280 nm. For example, in some embodiments, the UVC light sources may generate UV rays with a wavelength that is substantially close to 265 nm. The UVC light sources 108 in some embodiments may be UVC light emitting diodes (LEDs). The UVC light sources 108 and the air filter cartridges 112 may create a decontamination chamber 110 inside the casing 102 of the air breathing device 100. The terms decontamination chamber and air passage cavity is interchangeably used in this disclosure to refer to a cavity that is encompassed by the air breathing device casing 102. The decontamination chamber (or air passage cavity) may be connected to the outside of the casing 102 through one or more air intake ports 137 and one or more air discharge ports 138. The decontamination chamber (or air passage cavity) may be connected to the wearer's mouth through the air tube 147 that transfers air between the decontamination chamber (or air passage cavity) and the wearer's mouth.

At least a portion of (e.g., and without limitations, 75%, 85%, 95%, 99%, etc.) of the interior surface of the decontamination chamber 110 may be comprised of (e.g., may be made of, or may be covered by) a material that reflects UVC light. The reflective material includes material such as, for example, and without limitations, aluminum foil, expanded polytetrafluoroethylene (ePTFE), polyethylene film, etc. The reflective surface provides the technical advantage of increasing the exposure of the microorganisms to UV rays.

In some embodiments, the interior surface of the air breathing device's casing 102 may be embedded with one or more of the UV light sources 108 that may expose both incoming and leaving air (in and out of the air breathing device 100) to UV rays to sterilize and disinfect the air to avoid the spread of deceases. As described below, the air breathing device 100 is configured to totally encapsulate the UV rays, such that the skin, mouth, or eyes of the wearer are not exposed to UV rays, and the UV rays may not leave the casing 102 and enter into the surrounding area.

The number and the radiation flux of the UV light sources of the air breathing device 100, in some embodiments, may be selected such that a percentage of (e.g., and without limitations, 90%, 95%, 99%, etc.) of one type of microorganism or a percentage of multiple different types of microorganisms inside the air breathing device 100 are inactivated by the UV rays. The following is an example calculation of the efficacy of UV light, with peak emitted wavelength of 265 nm, in inactivating the severe acute respiratory syndrome coronavirus 2 (SARS-CoV-2) virus that causes COVID-19.

The radiation dosage of a UV light source may be expressed as shown in Equation (1):

$$D = E \times t \qquad \text{Eq. (1)}$$

where, D is radiation dosage in micro Joules per square centimeters $$\left[\frac{\mu J}{cm^2}\right],$$

E is the radiation intensity in micro Watts per square centimeters $$\left[\frac{\mu W}{cm^2}\right],$$

and t is the exposure time in seconds [s].

The article by Hiroshi Shimoda, et al, "Efficacy of 265-nm ultraviolet light in inactivating infectious SARS-COV-2," Journal of Photochemistry and Photobiology, Jun. 17, 2021, pp. 1-3, has provided the inactivation rates of SARS-COV-2 for different UV radiation doses and different UV wavelengths. The contents of this paper is incorporated herein by reference. The required dosage per Shimoda et al. for 99% inactivation of SARS-COV-2 using UVC LEDs, with peak emitting wavelength of 265 nm, may be expressed in Table 1:

TABLE 1

| | |
|---|---|
| Radiation intensity of light source $\left[\frac{\mu W}{cm^2}\right]$ | 210 |
| Exposure time [s] | 14.4 |
| Dosage required for 99% inactivation of SARS-CoV-2 $\left[\frac{\mu J}{cm^2}\right]$ | 3,022 |

Table 2 expresses the calculated exposure time for 140,000 μW of radiant flux, with peak emitted wavelength of 265 nm, in each of the two channels of the air breathing device 100 of the present embodiments (each channel is the portion of the decontamination chamber 110 that is located between one of the two UVC light isolation screens 114 and the central point of the UVC light isolation screen 111 of FIG. 1). The radiant influx may be increased to any desired value by adding more UVC light sources. The required dosage expressed in Table 2 is based on the research article by Shimoda et al. The radiation intensity expressed in Table 2 is calculated based on the performance data of a commercially available UVC light source, published as "UV-C LED Product Specifications SMD 3535 Packaged LED," by Bolb Inc., V4.0 March 2021. The contents of this publication is incorporated herein by reference.

The manufacturer has published the value of radiation intensity of 275 nm wavelength light for distance of 1 cm. This value is 8100

$$\left[\frac{\mu J}{cm^2}\right].$$

The manufacturer has also published the value of radiant flux of the light when it emits light with wavelength of 275 nm and 265 nm. The radiant flux for 275 nm wavelength is 40000 μW and for 265 nm is 35000 μW. As the radiation intensity is proportion to the radiant flux, the radiation intensity of 265 nm light emitted from this UVC LED light may be calculated as follows:

Radiation Intensity of Bolb Inc.'s UVC LED light model SMD 3535 emitted peak wavelength of 265 nm at 1 cm is $$3500/4000 \times 8100 = 7087 \left[\frac{\mu J}{cm^2}\right].$$

If four of these UVC LED lights are used inside each channel of the air breathing device 100, and assuming that each channel has 93% surface reflectivity as a result of being covered with a UVC reflective material such as ePTFE, then the radiation intensity inside each channel may be calculated as follows:

Radiation Intensity inside each channel is $$0.93 \times 4 \times 7087 \cong 26250 \left[\frac{\mu W}{cm^2}\right].$$

The assumption of 1 cm distance between the microorganisms travelling inside each channel of the air breathing device 100 and the UVC LED light source and reflective surfaces is a conservative assumption as the average wall to wall distance that the microorganisms are exposed to UVC light inside each channel is less than 1 cm.

TABLE 2

| | |
|---|---|
| Dosage required for 99% inactivation of SARS-CoV-2 $\left[\frac{\mu J}{cm^2}\right]$ | 3022 |
| Distance from source [cm] | 1 |
| Radiation intensity $\left[\frac{\mu W}{cm^2}\right]$ | 26250 |
| Required Exposure time to achieve 99% inactivation of SARS-CoV-2 calculated by using Eq. (1) [s] | 0.115 |

Table 3 shows the duration of air exposure to UVC light inside the air breathing device 100 of the present embodiments in inhale or exhale process. The parameters in Table 3 may be used for calculation of time duration of air exposure to UVC rays inside the air breathing device 100 of the present embodiments.

TABLE 3

| | |
|---|---|
| Tidal capacity of an average adult human's lung [cm³] | 500 |
| Volume of air passing through each channel in one inhale or exhale [cm³] | 250 |
| Cross sectional area of air channel in the air breathing device 100 [cm²] | 5 |
| Duration of peak, instantaneous inhale or exhale at rest [s] | 0.59 |
| Velocity of air through the air channel [cm/s] | 84.75 |
| Length of each channel of the air breathing device 100 [cm] | 13 |
| Duration of air exposure to UVC [s] | 0.153 |

Based on Table 3, the inhaled or exhaled air is exposed to UVC rays inside the air breathing device 100 for 0.153 seconds. This value is about 32% higher than the required exposure time of 0.115 seconds in Table 2 to achieve 99% inactivation rate with 140,000 ρW of UVC light radiant flux (which is the capacity of the air breathing device 100 with 4 LED light sources emitting UVC light, with wavelength of 265 nm, inside each channel). This result shows that the air breathing device 100 is able to achieve at least 99% SARS-COV-2 inactivation rate. However, it is also feasible to increase the radiant flux by adding more UVC light sources. For example, the radiant flux may be increased from 140,000 μW to 280,000 μW, to achieve higher inactivation rates.

There have been successful research efforts to determine the required UV light radiation dose for inactivation of various microorganisms such as viruses, bacteria, and fungi. For example, the research article by Do-Kyun Kim et al., "UVC LED Irradiation Effectively Inactivates Aerosolized Viruses, Bacteria, and Fungi in a Chamber-Type Air Disinfection System," Applied and Environment Microbiology, Volume 84, Issue 17, September 2018, pp. 1-11, has data on the required doses for different inactivation rates of various viruses, bacteria, and fungi. The contents of this paper is incorporated herein by reference. Such data may be used to adjust the radiant flux inside the decontamination chamber 110 of the air breathing device 100 in order to inactivate a specific microorganism that is present in the air.

This adjustment in radiant flux maybe performed by turning off some of the UV light sources inside the chamber or by adjusting the radiant power of each UV light source. For example, commercially available UV LED lights are able to emit down to about 10% of their rated radiant flux.

The microorganism that may be present in the air may be selected from a user interface of an external electronic device and may be communicated to the air breathing device 100. The processor 140 of the air breathing device 100 may set the radiant power to a level which inactivates the selected microorganism at a user defined rate, for example, 99% inactivation rate for SARS-COV-2. The data for the required radiation dose for inactivation of various microorganisms may be uploaded to the air breathing device 100 by an external electronic device, such that, as new data become available or new microorganisms are discovered, the air breathing device 100 may continue to stay useful for the wearer.

The UV light sources 108 may be powered by one or more on-board rechargeable batteries (e.g., and without limitations, lithium ion batteries) 109, and/or powered through an external source via an electric connection, such, as, for example, and without limitations, a universal serial bus (USB) port 410 (shown in FIG. 4D) mounted on the casing 102. The batteries 109, in some embodiments, may be removed and the air breathing device 100 may operate via the external power source to reduce the weight of the air breathing device 100 and provide additional comfort for the wearer. Power through the USB port 410 may be used, for example, and without limitations, when the wearer is sitting in an airplane chair or in an office chair over an extended period of time. Power through the USB port 410 may be also used to recharge the batteries. The electric connection (or the USB port 410) may also be used to send and receive signals with electronic devices that are external to the air breathing device 100.

In some embodiments, the UV light sources 108 may be turned on or off by a UV Light on/off switch 122. For example, in an environment where there is little or no danger of microorganism exposure, the UV light sources 108 may be turned off and the air breathing device 100 may be used to protect the wearer from dust, fumes, noxious gases, etc., present in the ambient or generated during various tasks. The UV light status indicator 196 may be a window covered by a glass that converts the UV light to a visible harmless light to indicate whether the UV light sources 108 are operating or not.

The casing 102 of the air breathing device 100 may be made of an opaque material to isolate the UV rays in the interior of the casing 102 and prevent the UV rays to leak out of the back side of the casing 102 towards the face of the wearer. The UVC light isolation screen 111 may be configured to prevent the mouth of the wearer from being exposed to the UV rays. The air breathing device 100 may include the air tube 147 to transfer air between the decontamination chamber 110 and the facepiece 180. The air tube may be made of an opaque material. The air may be transferred through air tube 147 into, and out of, the wearer's mouth. The UVC light isolation screen 111 may be positioned inside the air tube 147 to prevent UV rays to leak from the decontamination chamber 110 into the wearer's mouth.

The UVC light isolation screens 114 may be configured to prevent the UV light from leaking to the outside of the casing 102 through the air intake ports 137 and the air discharge ports 138. The casing 102 and the UVC light isolation screens 111 and 114 provide the technical advantage of completely confining the UV rays inside the casing 102 and preventing the UV rays from reaching the wearer and from entering the surrounding area even during the replacement of the air filter cartridge.

Figure 7A:
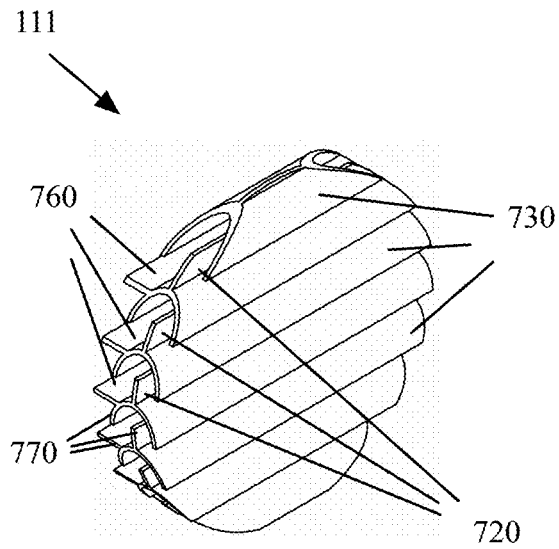
FIG. 7A is a front perspective view.
Figure 7B:
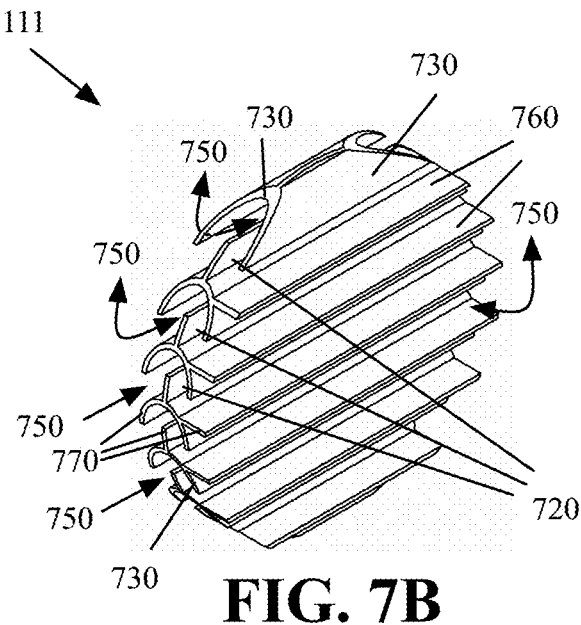
FIG. 7B is a back perspective view.
Figure 7C:
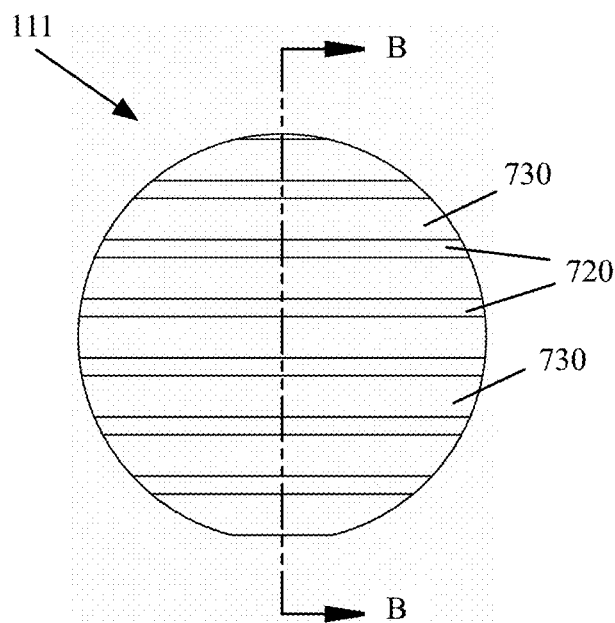
FIG. 7C is a back elevation view of a UVC light screen that is located inside the air tube, according to various aspects of the present disclosure.
Figure 7D:
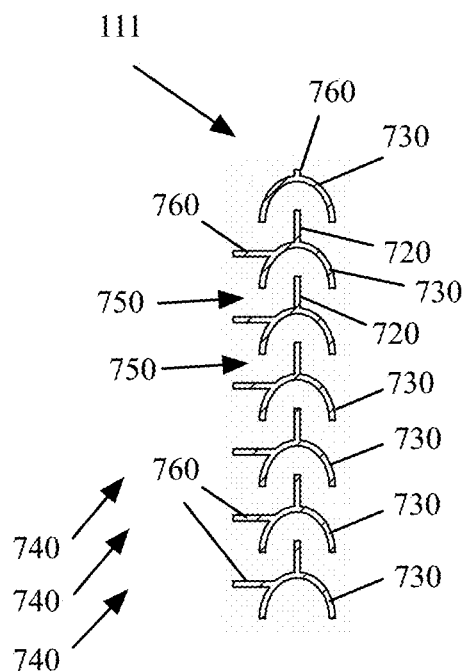
FIG. 7D is a side cross sectional view of the UVC light screen of FIGS. 7A-7C along the line B-B shown in FIG. 7C.

FIG. 7A is a front perspective view, FIG. 7B is a back perspective view, and FIG. 7C is a back elevation view of a UVC light screen 111 that is located inside the air tube 147 of FIG. 1, according to various aspects of the present disclosure. FIG. 7D is a side cross sectional view of the UVC light screen 111 along the line B-B shown in FIG. 7C.

With reference to FIGS. 7A-7D, the UVC light screen 111 may be located inside the air tube 147 (FIG. 1). The UVC light screen 111 blocks UVC light from reaching the wearer's face while allowing air to pass. The UVC light screen 111 may be made of, or covered by, materials that is opaque to the UVC light and do not reflect the UVC light.

As shown, the UVC light screen 111 may include three sets of one or more plates 720, 730, and 760. The depicted embodiment includes a plurality of plates 720, a plurality of plates 730, and a plurality of plates 760. The set of plates 730 may include one or more curved plates 730, the set of plates 720 may include one or more plates 720 that may be of an arbitrary shape, and the set of plates 760 may include one or more plates 760 that may be of an arbitrary shape. The sets of plates 720, 730, and 760 may be made of, or covered by, materials that is opaque to the UVC light and do not reflect the UVC light.

As shown in the cross section of FIG. 7D, the three sets of opaque plates 720, 730, and 760 collectively block all UVC lights 740, but allow air to go through the openings 750 among the plates 720, 730, and 760. Each of the plates 720 may be positioned to extend within the curvature of a plate 730. The set of plates 720, 730, and 760 are configured such that the UVC light 740 is prevented from reaching the wearer's face while the air may pass through the openings 750 that are around the plate(s) 720 and within the concaved side of the plate(s) 730.

The opposite sides of the sets of plates 720, 730, and 760 (collectively marked as 770 on FIGS. 7A and 7B) may be connected to the casing of the air breathing device. The function of the set of plates 760, in the depicted embodiment, is to block UVC light 740 in oblique angles to pass through the openings 750. Each plate 720 may be connected to a plate 730, and each plate 760 may be connected to a plate 730 as shown in FIG. 7D. For clarity, some of the plates 720, 730, 760, some of the openings 750, and some of the opposite ends 770 that are connected to the casing are not labeled in FIGS. 7A-7D.

The collective shape of the set of plates 730 may substantially conform to the shape of the cross section of the air tube 147. For example, when the cross section of the air tube 147 is substantially circular, the collective shape of the set of plates 730 may be substantially circular. In other embodiments, the cross section of the air tube 147 and the collective shape of the set of plates 730 may be substantially rectangular, or may be an arbitrary shape.

Figure 8A:
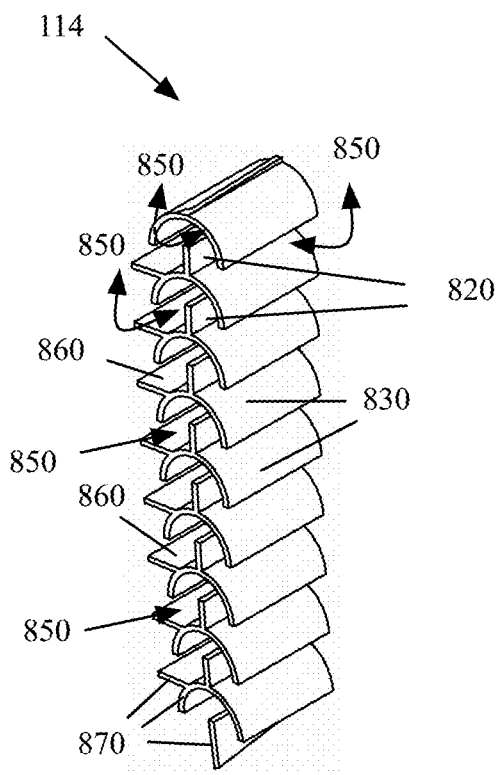
FIG. 8A is a front perspective view.
Figure 8B:
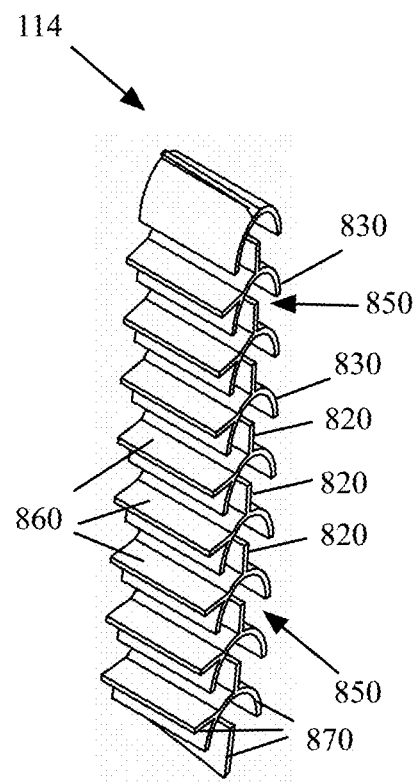
FIG. 8B is a back perspective view.
Figure 8C:
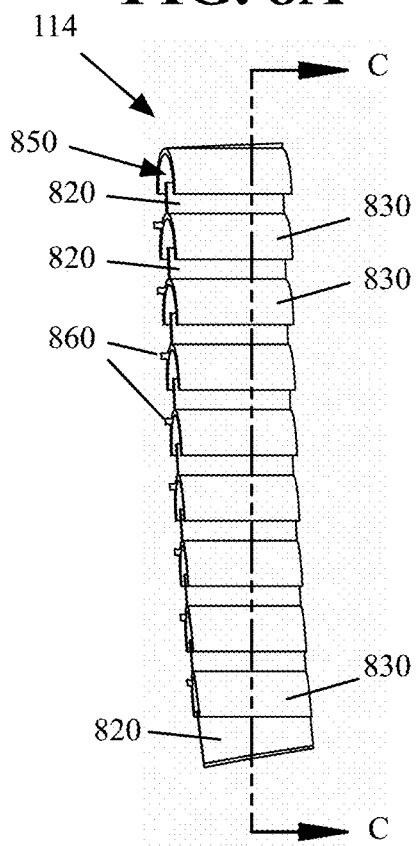
FIG. 8C is a back elevation view of a UVC light screen that may prevent the UVC light to leak outside the casing of the air breathing device, according to various aspects of the present disclosure.
Figure 8D:
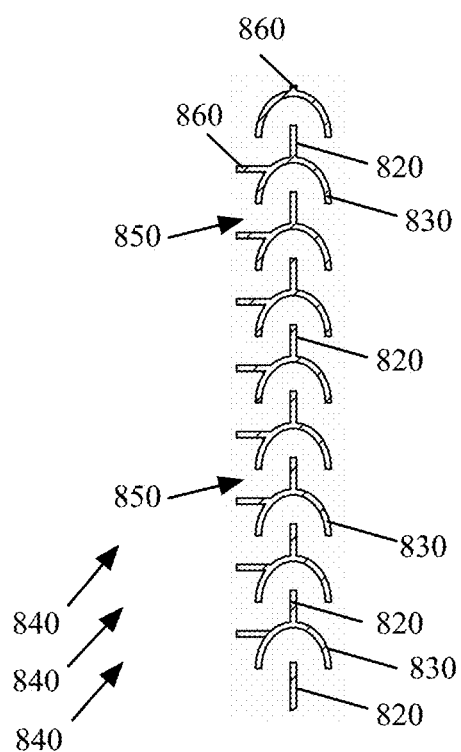
FIG. 8D is a side cross sectional view of the UVC light screen of FIGS. 8A-8C along the line C-C shown in FIG. 8C.

FIG. 8A is a front perspective view, FIG. 8B is a back perspective view, and FIG. 8C is a back elevation view of a UVC light screen 114 that may prevent the UVC light to leak outside the casing 102 of the air breathing device, according to various aspects of the present disclosure. FIG. 8D is a side cross sectional view of the UVC light screen 114 along the line C-C shown in FIG. 8C.

With reference to FIGS. 8A-8D, the UVC light screen 114 prevents the UVC light to leak outside the casing 102 of the air breathing device 100. The UVC light screen 114 may be made of, or covered by, materials that is opaque to the UVC light and do not reflect the UVC light. As shown in FIG. 1, the UVC light screens 114 may be used to block UVC light from reaching the air intake ports 137 or air discharge ports 138 while allowing air to pass.

With further reference to FIGS. 8A-8D, the UVC light screen 114 may include three sets of one or more plates 820, 830, and 860. The depicted embodiment includes a plurality of plates 820, a plurality of plates 830, and a plurality of plates 860. The set of plates 830 may include one or more curved plates 830, the set of plates 820 may include one or more plates 820 that may be of an arbitrary shape, and the set of plates 860 may include one or more plates 860 that may be of an arbitrary shape. The sets of plates 820, 830, and 860 may be made of, or covered by, materials that is opaque to the UVC light and do not reflect the UVC light.

As shown in the cross section of FIG. 8D, the three sets of opaque plates 820, 830, and 860 collectively block all UVC lights 840, but allow air to go around the openings 850 among the plates 820, 830, and 860. Each of the plates 820 may be positioned to extend within the curvature of a plate 830. The set of plates 820, 830, and 860 are configured such that the UVC light 840 is prevented from reaching outside the casing of the air berating device into the surrounding environment while the air may pass through the openings 850 that are around the plate(s) 820 and within the concaved side of the plate(s) 830.

The opposite sides of the sets of plates 820, 830, and 860 (collectively marked as 870 on FIGS. 8A and 8B) may be connected to the casing of the air breathing device. The function of the set of plates 860, in the depicted embodiment, is to block UVC light 840 in oblique angles to pass through the openings 850. Each plate 820 may be connected to a plate 830, and each plate 860 may be connected to plate 830 as shown in FIG. 8D. For clarity, some of the plates 820, 830, 860, some of the openings 850, and some of the opposite ends 870 that are connected to the casing are not labeled in FIGS. 8A-8D.

It should be noted that the light screens 111 and 114 are two examples of UVC light screens that some embodiments use to allow the air to go through and block UVC light. Other embodiments may use other types of UVC light screens to achieve the same result of allowing the air to go through and blocking the UVC light. For example, some embodiments may use a surface with grate like perforations that block the UVC light but allow the air to go around the perforations.

The air breathing device 100 may include one or more harness handles 105. the harness handles 105 may be used to a set of harnesses (or straps) 106 (FIG. 2) to the casing 102. For clarity, the harnesses are not shown in FIGS. 1 and 3-4. The harnesses 106 may be configured to secure the air breathing device 100 behind the head and neck of the wearer. The harness 106, in some embodiments, may be made of soft and flexible material. The harness 106, in other embodiments, may be made of semi soft material to allow one or more accessories to be placed on the harness, as described further below.

Optionally, the air breathing device 100, in some embodiments, may provide one or more electric heating coils 136 to warm up the air before being inhaled by the wearer. The purpose of the electric heating coils 136 are to warm up the inhalation air in cold environments. Warming up the breathing air may prevent the wearer from catching cold or pneumonia during cold seasons. The heating coils 136 may be located between the air intake dampers 113 and the decontamination chamber 110.

The source of power for the electric heating coil 136 may be the on-board rechargeable batteries 109 or through an external power source via USB port 410 (FIG. 4D) mounted on the casing 102. Power through the USB port may be used, for example, and without limitations, when the wearer is sitting in a chair and using the air breathing device 100 over an extended period of time. The air breathing device 100, may include one or more air temperature sensors 131. The air temperature sensors 131 may be configured to measure the temperature of the air being inhaled inside the casing 102 downstream of the electric heating coil 136 and/or the temperature of the outside air prior to reaching the air filter cartridge 112. The processor 140 may receive the air temperature sensors 131 readings and may control the air temperature inside the casing 102.

The air temperature sensors 131 measurements may be used by the processor 140 of the air breathing device 100 to control the temperature of the air being inhaled. For example, the processor may regulate the temperature of the air being inhaled by modulating (i.e., adjusting the temperature up or down) or turning the electric heating coil 136 on or off. The processor 140 may receive the temperature measurements from the temperature sensors 131 and may compare the temperature measurements with a user-selectable threshold. The processor 140 may receive first and second user-selectable thresholds from an external electronic device (e.g., a smartphone, a desktop, a laptop, a tablet, etc.) through one of the transceivers 130.

The processor 140 may turn on the power to the heating coil 136 when the temperature inside the casing 102 is below the first threshold. The processor 140 may turn off the power to the heating coil 136 when the temperature inside the casing 102 is above the second threshold, which is larger than the first threshold.

The temperature of the air inside the casing 102, in some embodiments, may be controlled by an application program running on an external electronic device, such as a smartphone, a laptop, a tablet, a desktop computer, etc. For example, the application program may receive a temperature selection through a user interface and may wirelessly send the temperature selection, through one of the wireless transceivers 130, to the processor 140 of the air breathing device 100 to modulate (i.e., adjust the temperature up or down) or turn the electric heating coil 136 on or off. Some embodiments may provide a temperature selection control (not shown) on the casing 102. The temperature selection control may be a knob. The temperature selection control may be a multi position switch to control the temperature, for example, to low, medium, or high. The processor 140 of the air breathing device 100 may use the knob or the switch selection to control the temperature inside the casing 102 by modulating or turning the electric heating coil 136 on or off.

In the embodiment depicted in FIGS. 1-4D, the air breathing device 100 includes two electric heating coils 136, which are located close to the corresponding air intake ports 137. Other embodiments may include a different number of electric heating coils, which may be placed in other locations inside the casing 102. The electric heating coil 136, in some embodiments, may be removed, for example, to do maintenance, or to reduce the weight and air pressure drop during warm seasons. The electric heating coil 136 may be removed through the access cover 184 that provides access to both the air intake dampers 113 and the electric heating coil 136.

It should be noted that the number and the locations of different components of the air breathing device 100 may be different in different embodiments. As such, the figures only show examples of the number and the location of different components of the air breathing device 100. For instance, the number and the location of the UV light sources 108 may be different in different embodiments. Different embodiments may include one or more air intake ports 137, where each air intake port may include one or more air filter cartridges 112 (either a combined air filter cartridge or separate particulate and carbon filters), and a set of air intake dampers 113. The air intake ports 137 may be located in front and/or on the four sides (left, right, up, or down sides) of the casing 102.

Different embodiments may include one or more air discharge ports 138, where each air discharge port 138 may include a set of air discharge dampers 117. The air discharge ports 138 may be located in front, and/or on the four sides (left, right, up, or down sides) of the casing 102. The depicted embodiment include one UVC light isolation screen 114 for each pair of air intake port 137 and air discharge port 138. In other embodiments, each air intake port 137 and air discharge port 138 may include a separate UVC light isolation screen 114.

Figure 9:
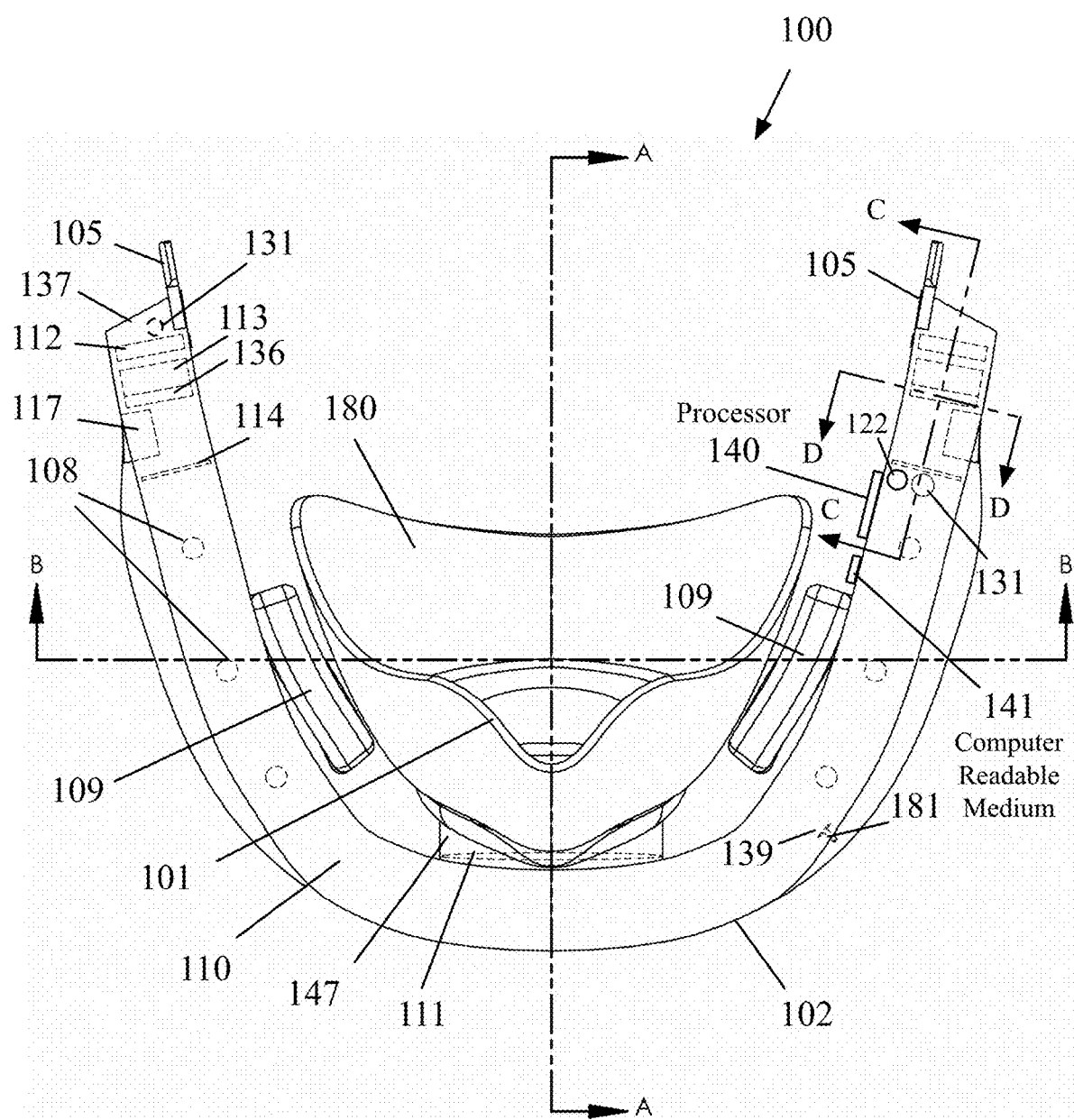
FIG. 9 is a top view of the reusable purified air breathing device of FIG. 1, illustrating different components of the air filtration and sterilization of the air breathing device, according to various aspects of the present disclosure.

FIG. 9 is a top view of the reusable purified air breathing device of FIG. 1, illustrating different components of the air filtration and sterilization of the air breathing device, according to various aspects of the present disclosure. FIG. 9 illustrates different components of the air breathing device 100, such as the facepiece 180, the nose enclosure 101, the harness handles 105, the UV light sources 108, the rechargeable batteries 109, the UVC light isolation screens 111 and 114, the air filter cartridges 112, the dampers 113 and 117, the electric heating coils 136, the air temperature sensors 131, the UV Light on/off switch 122, and the air pressure differential sensor 139. For clarity, some of the UV light sources 108 are not shown and/or not labeled.

As shown in FIG. 9, the UVC light isolation screens 114 are between the corresponding air filter cartridge 112 and the interior of the casing 102, allowing the air filter cartridges 112 to be changed even when the UV light sources 108 are on, without the UV light to leak to the outside of the casing 102.

Figure 10:
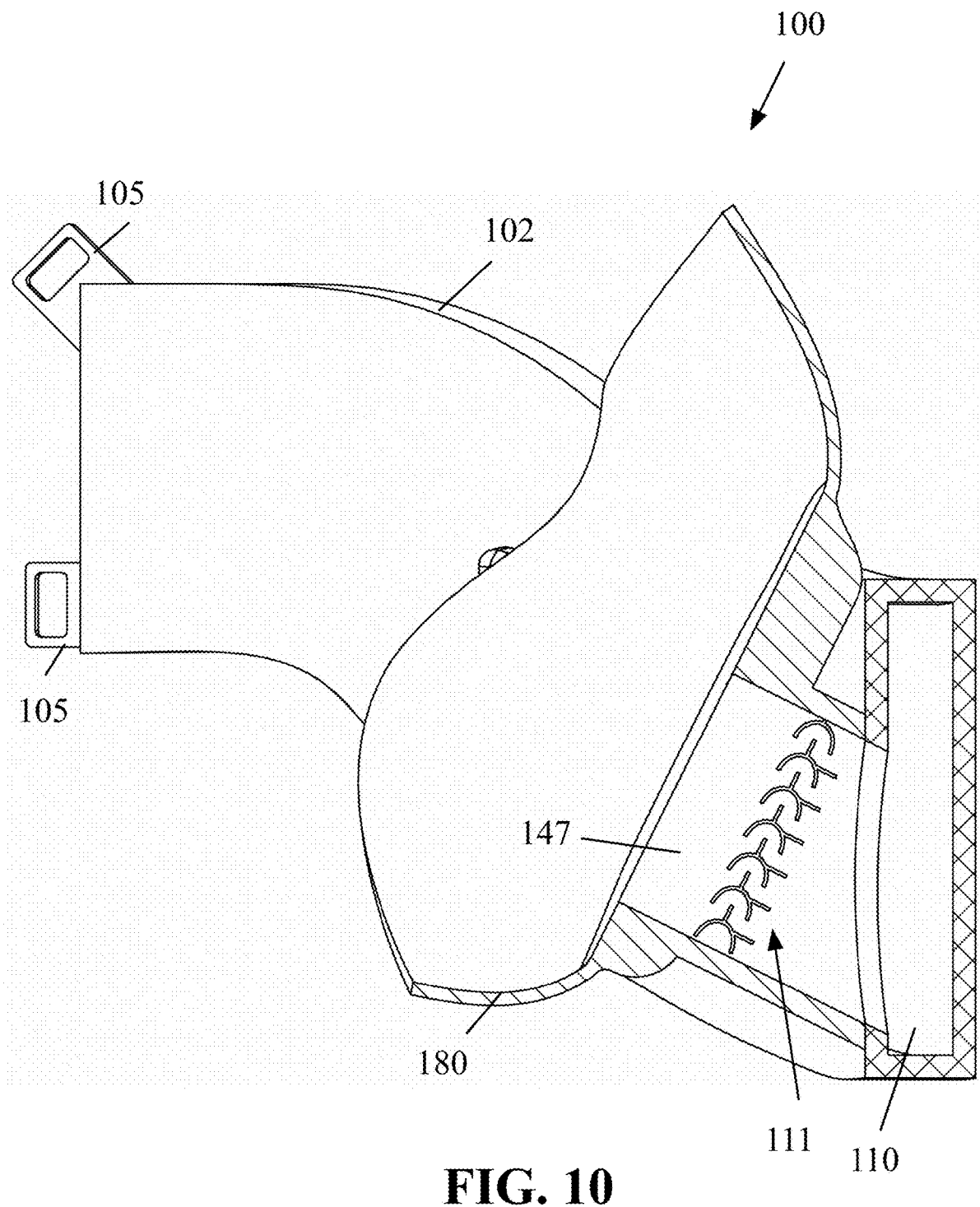
FIG. 10 is a side cross sectional view of the reusable purified breathing air device along the line A-A shown in FIG. 9, according to various aspects of the present disclosure.
Figure 11:
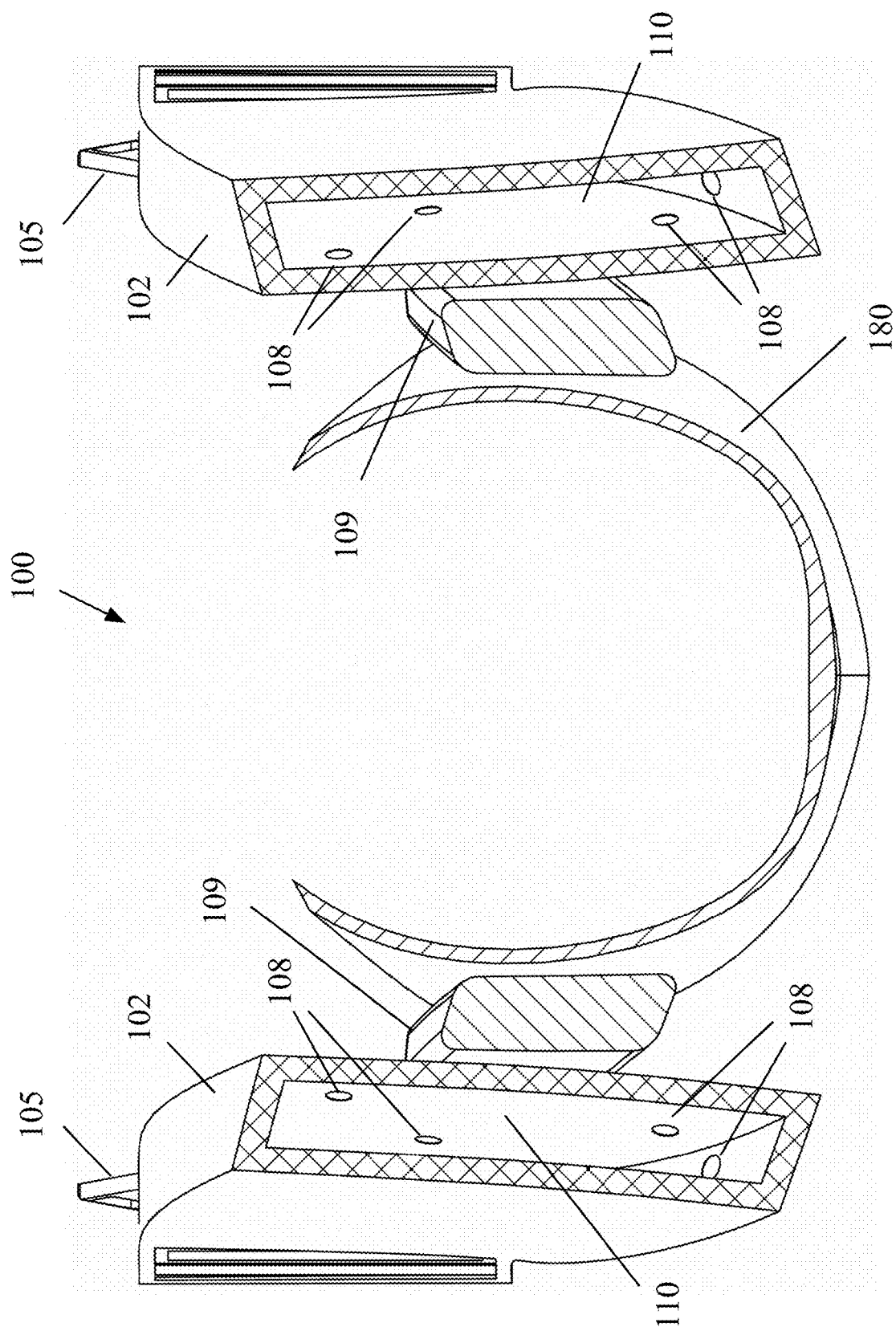
FIG. 11 is a front cross sectional view of the reusable purified air breathing device along the line B-B shown in FIG. 9, according to various aspects of the present disclosure.

FIG. 10 is a side cross sectional view of the reusable purified breathing air device along the line A-A shown in FIG. 9, and FIG. 11 is a front cross sectional view of the reusable purified air breathing device along the line B-B shown in FIG. 9, according to various aspects of the present disclosure. With reference to FIG. 10, the air tube 147 may transfer the air between the decontamination chamber 110 and the wearer's mouth. As shown in FIG. 10, the UVC light isolation screen 111 may be positioned inside the air tube 147 to prevent UV light to leak from the decontamination chamber 110 into the wearer's mouth.

With reference to FIG. 11, the interior surface of the decontamination chamber 110 may reflect UV light. The reflective material includes material such as, for example, and without limitations, aluminum foil, ePTFE, polyethylene film, etc. The reflective surface increases the exposure of the microorganisms to UV rays. Every side in the interior of the decontamination chamber 110 may include UV light sources and the reflective surfaces.

The placement of the UV light sources 108 inside the interior cavity (e.g., inside the decontamination chamber 110), as opposed to placing the UV light sources 108 outside the casing 102 of the air breathing device provides the technical advantage of exposing the microorganisms that have already entered the air breathing device 100 (either from the outside environment or through the wearer's mouth) as well as preventing the wearer and persons near the wearer from being exposed to UV rays. The reflective surface placed inside the interior cavity (e.g., inside the decontamination chamber 110) provides the technical advantage of increasing the exposure of the microorganisms to UV rays.

Figure 13:
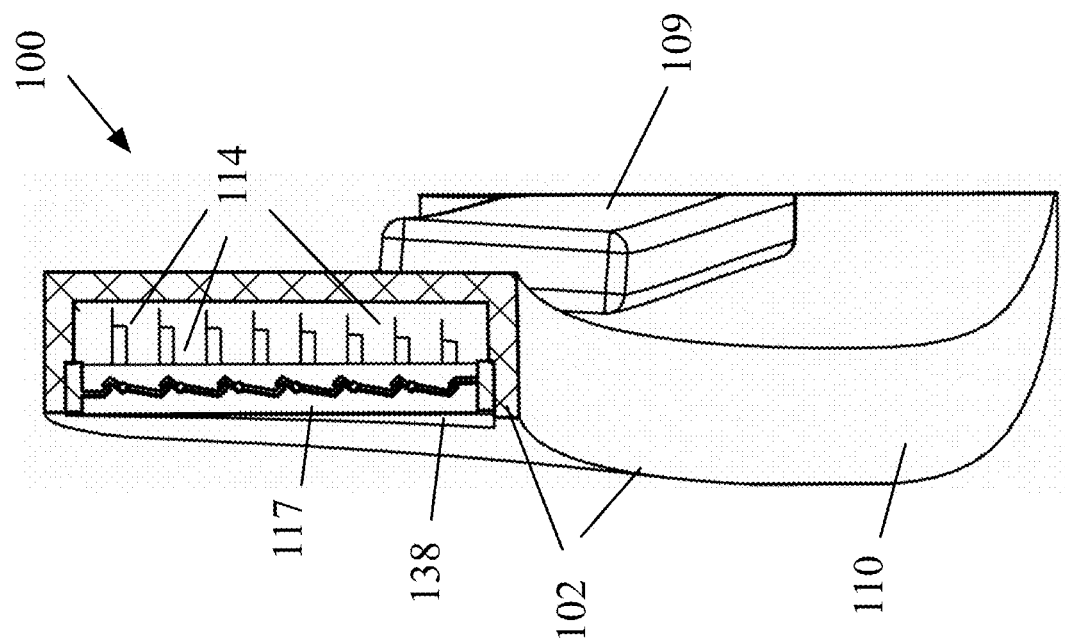
FIG. 13 is a front cross sectional view of the reusable purified air breathing device along the line D-D shown in FIG. 9, according to various aspects of the present disclosure.
Figure 12:
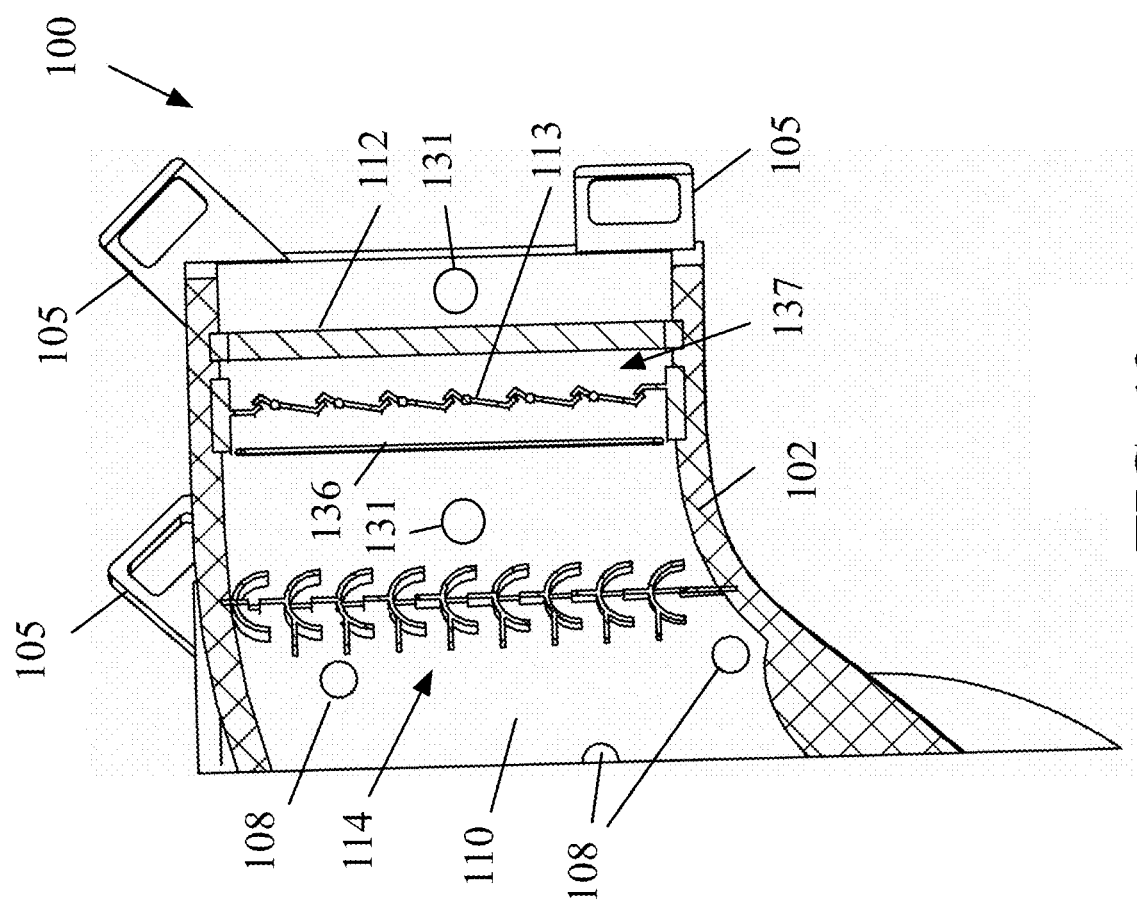
FIG. 12 is a side cross sectional view of the reusable purified breathing air device along the line C-C shown in FIG. 9, according to various aspects of the present disclosure.

FIG. 12 is a side cross sectional view of the reusable purified breathing air device along the line C-C shown in FIG. 9, and FIG. 13 is a front cross sectional view of the reusable purified air breathing device along the line D-D shown in FIG. 9, according to various aspects of the present disclosure. The cross section of FIG. 12 shows the air intake port 137, the air filter cartridge 112, the intake dampers 113, the electric heating coil 136, the air temperature sensors 131, the harness handles 105, some of the UV light sources 108, and the UVC light isolation screen 114.

The cross section of FIG. 13 shows the UVC light isolation screen 114 and the discharge dampers 117. The position of the UVC light isolation screen 114 is such that the UV light sources 108 are separated from the exterior of the casing 102. For example, as shown in FIG. 12, the UVC light isolation screen 114 is between the UV light sources 108 and the air discharge port 138. As shown in FIG. 13, the UVC light isolation screen 114 is positioned such that the exhaled air goes through the UVC light isolation screen 114 before the air is discharged through the discharge dampers 117 to the outside of the casing 102.

II. Alternative Embodiments

The air breathing device of some embodiments may provide connection to different networks, such as, for example, and without limitations, connection to the Internet, connection to cellular networks, a Wi-Fi connection, a Bluetooth connection, etc. The air breathing device, in some embodiments, may function as an Internet of Things (IoT) device.

Figure 14:
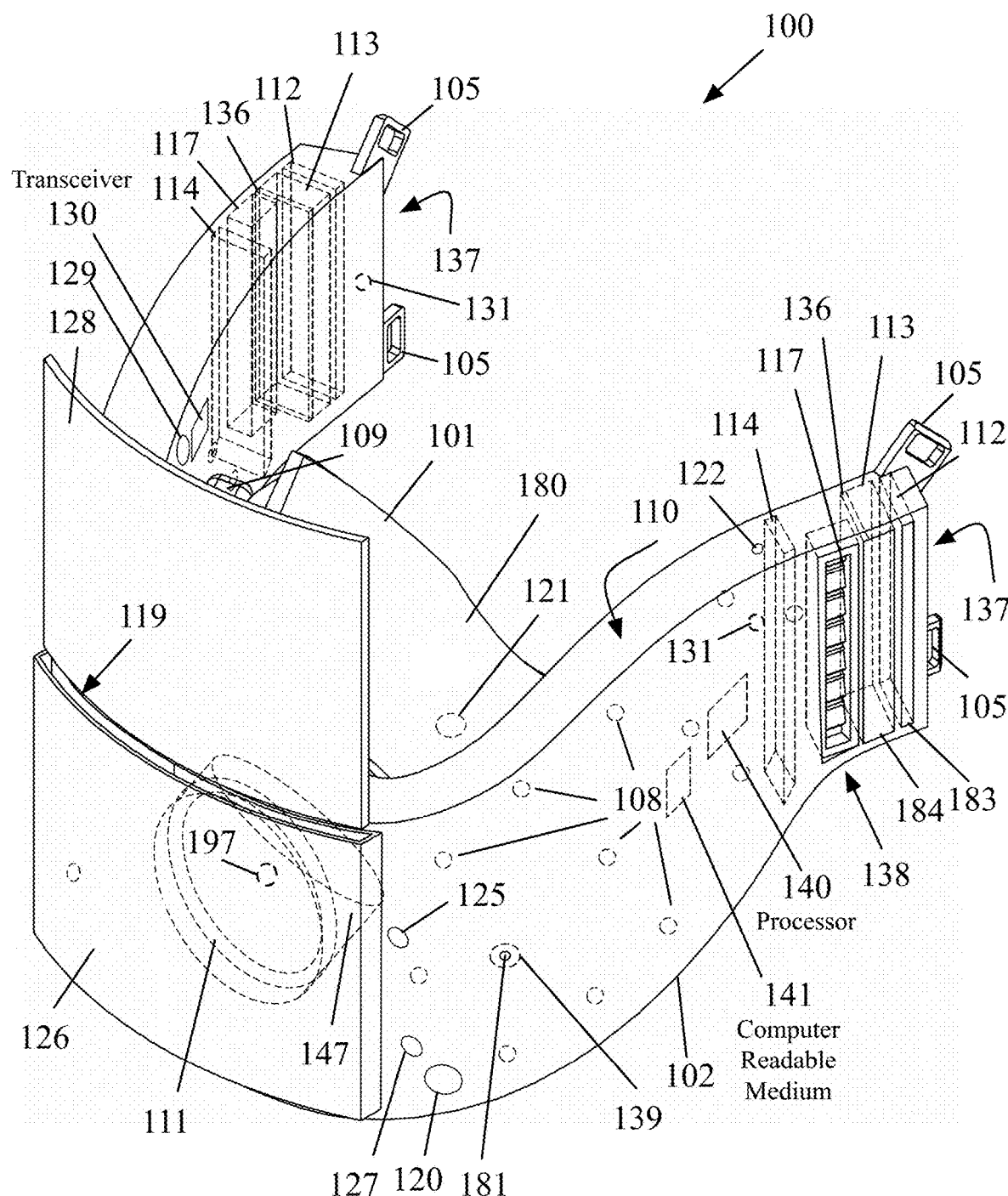
FIG. 14 is a perspective view of a reusable purified air breathing device that provides network connection, one or more cameras, one or more display screens, a global positioning system (GPS) receiver, a microphone, a flashlight, one or more wireless transceivers, and/or one or more speaker(s), according to various aspects of the present disclosure.
Figure 15:
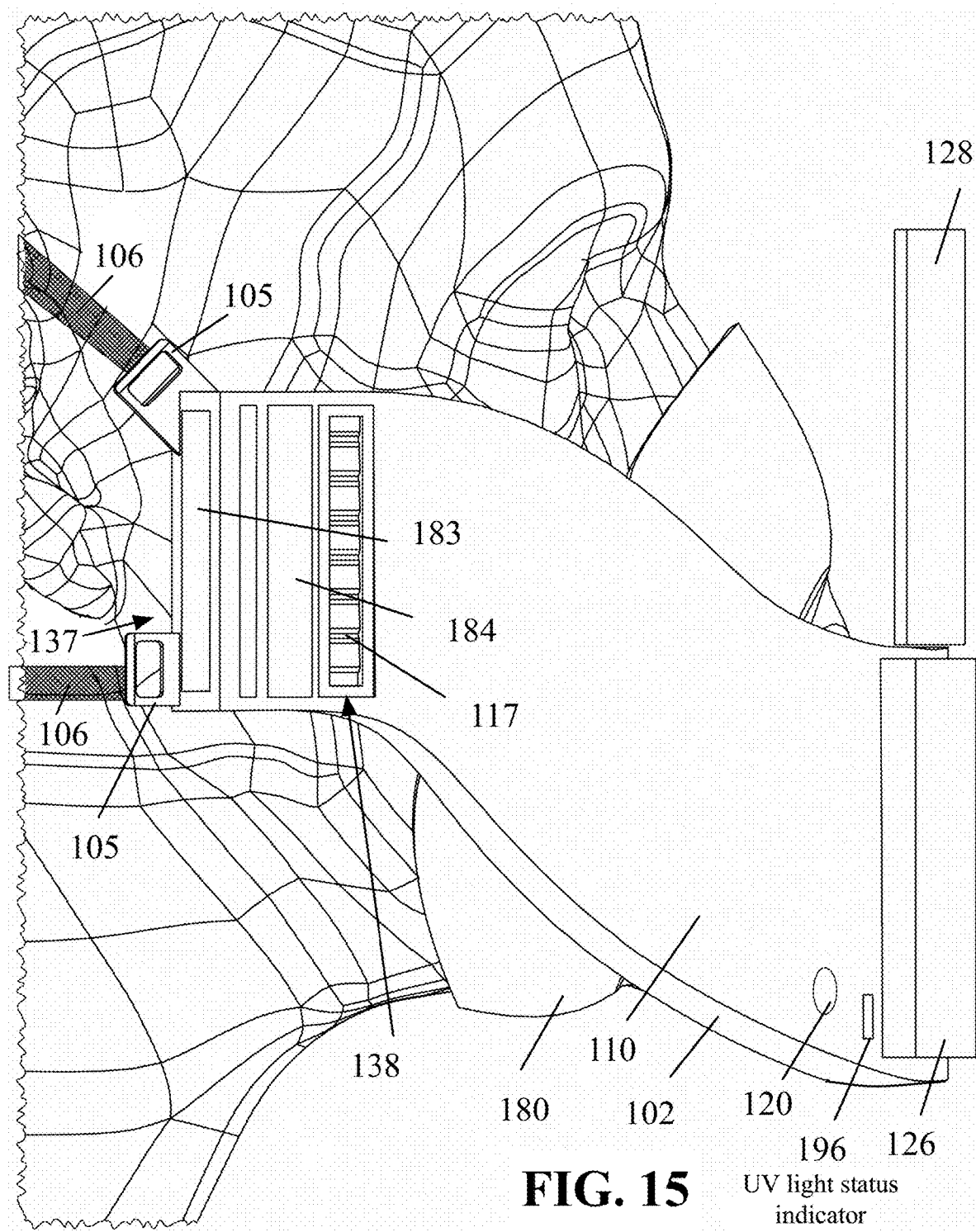
FIG. 15 is a side elevation view.
Figure 16:
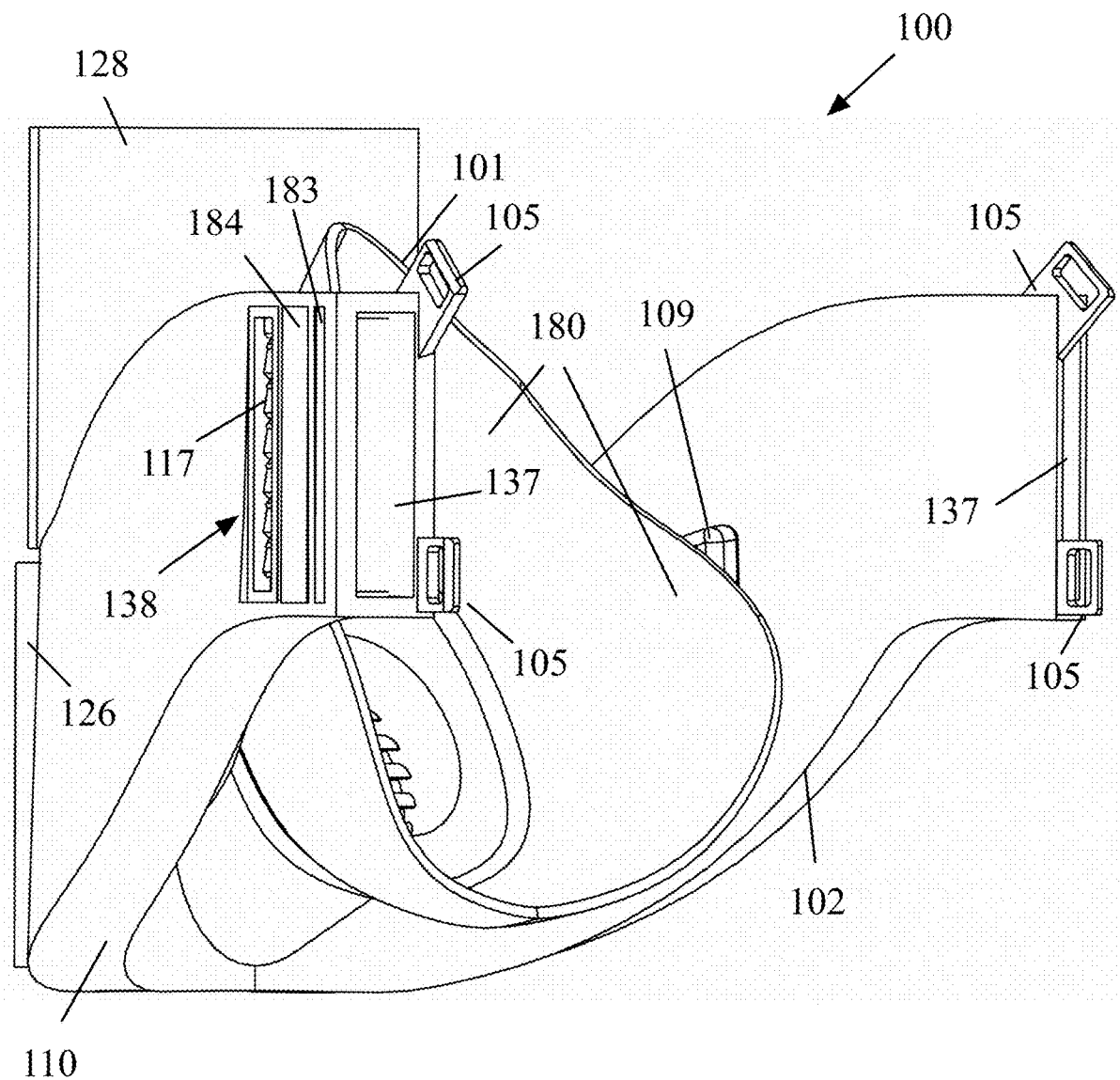
FIG. 16 is a back perspective view.
Figure 17A:
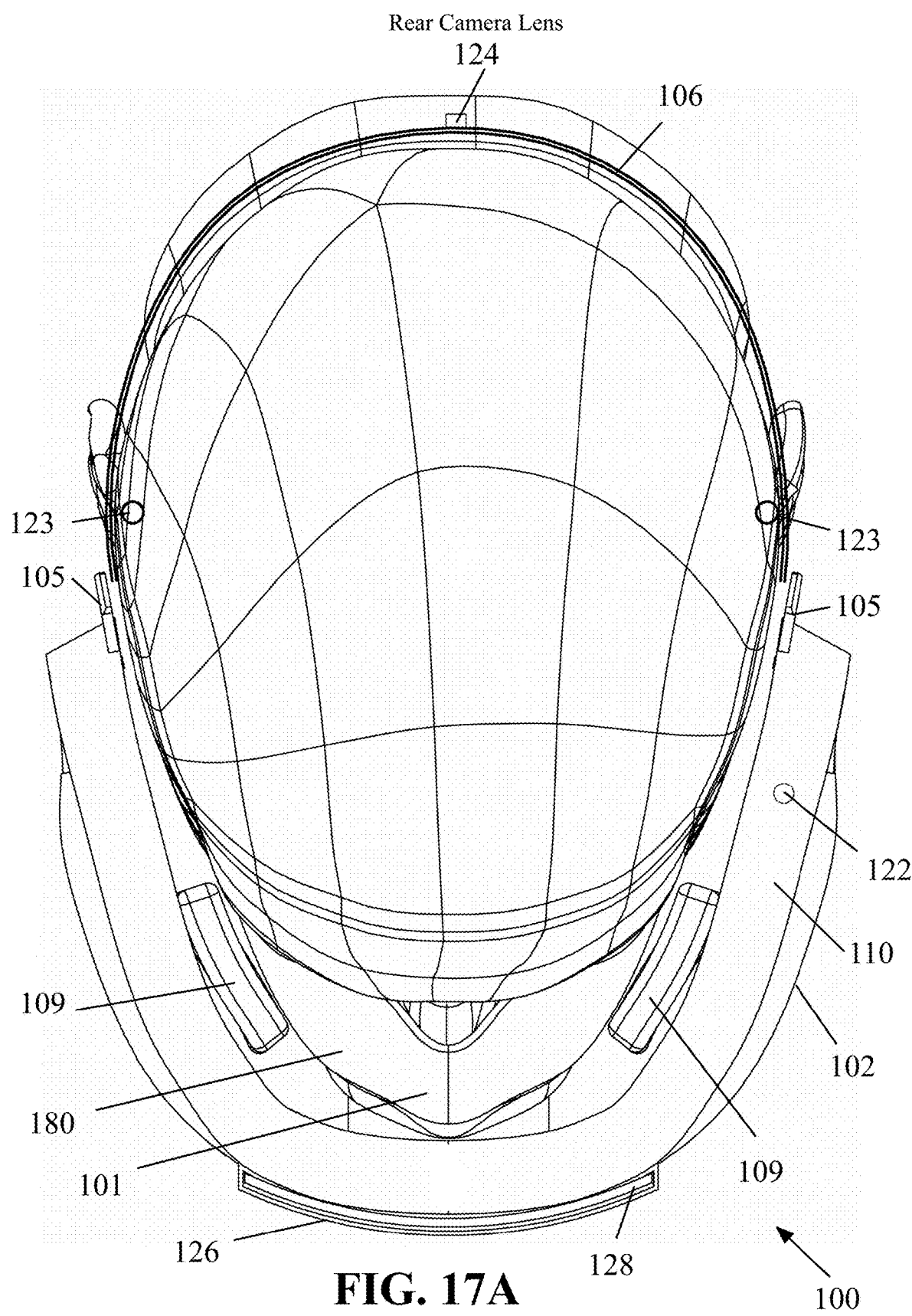
FIG. 17A is a top view.
Figure 17B:
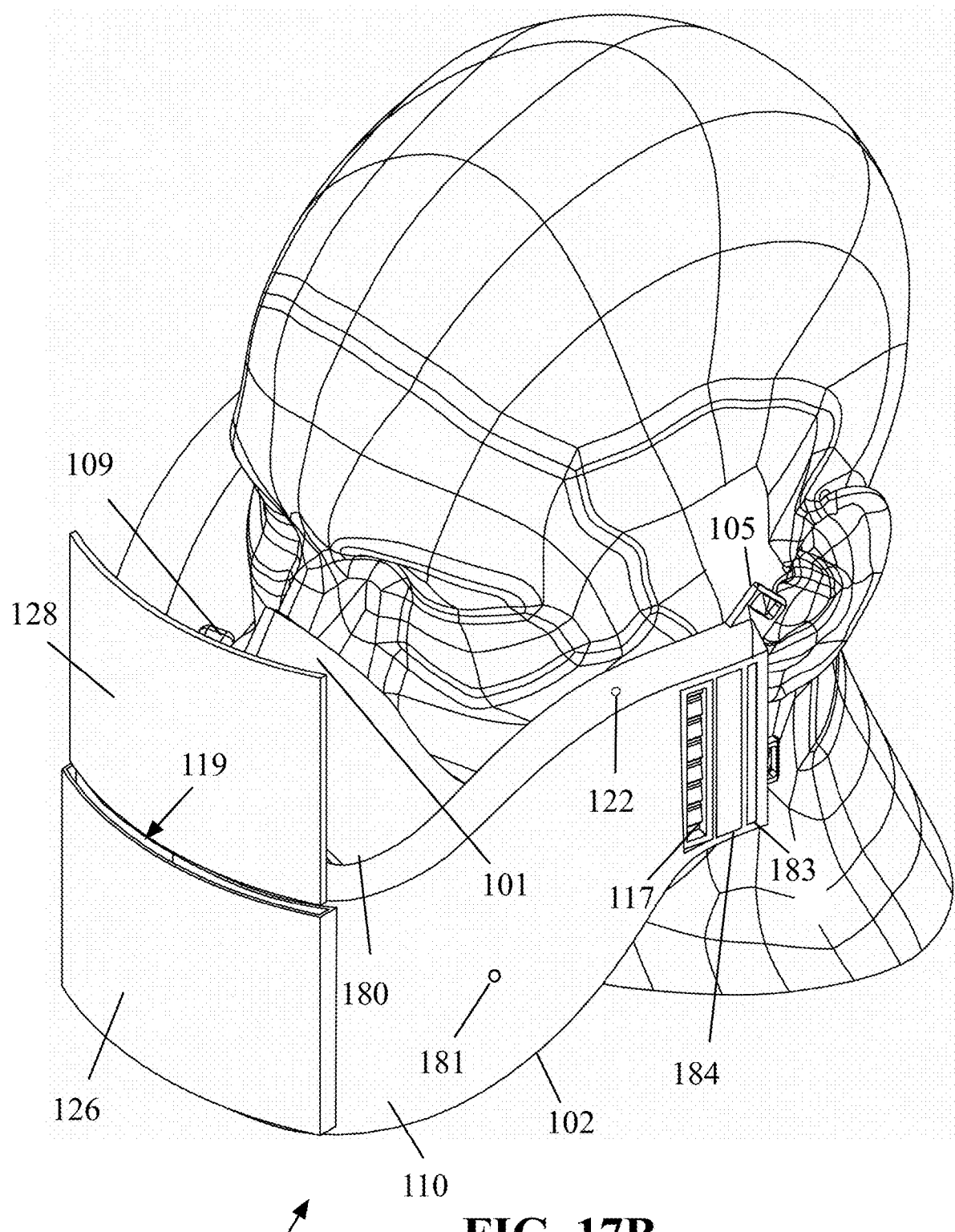
FIG. 17B is a side perspective view.
Figure 17C:
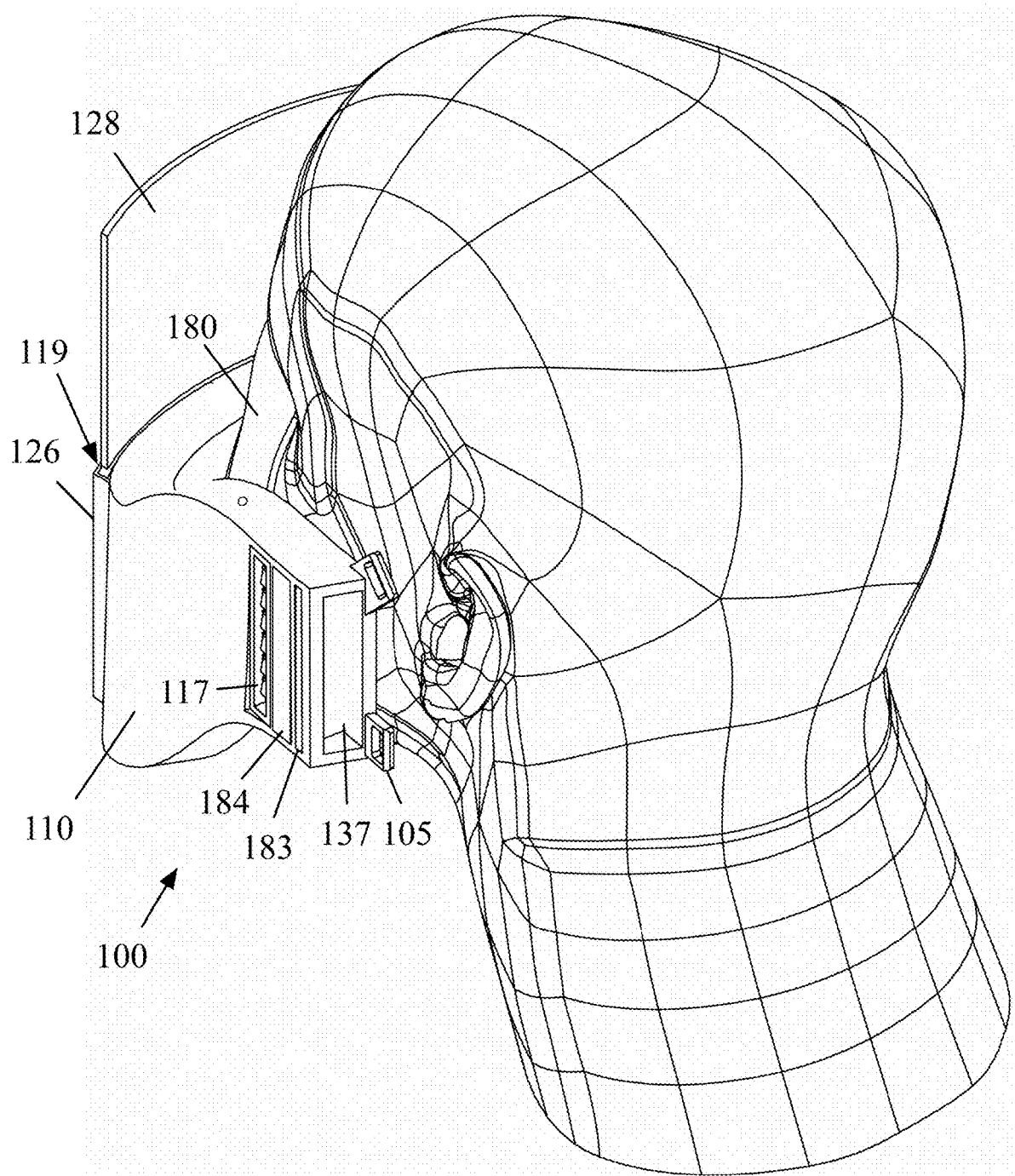
FIG. 17C is a back and side perspective view of the reusable purified air breathing device of FIG. 14.

FIG. 14 is a perspective view of a reusable purified air breathing device that provides network connection, one or more cameras, one or more display screens, a GPS receiver, a microphone, a flashlight, one or more wireless transceivers, and one or more speaker(s), according to various aspects of the present disclosure. FIG. 15 is a side elevation view, and FIG. 16 is a back perspective view, FIG. 17A is a top view, FIG. 17B is a front and side perspective view, and FIG. 17C is a back and side perspective view of the reusable purified air breathing device of FIG. 14. FIGS. 15-17C only show the components of the air breathing device 100 that are visible from the outside of the air breathing device 100.

With reference to FIGS. 14-17C, the air breathing device 100 may include similar components as the air breathing device 100 of FIGS. 1-13. For example, the air breathing device 100 of FIGS. 14-17C may include a nose enclosure 101, a casing 102, several harness handles 105, one or more harnesses (or straps) 106, one or more UV light sources 108, a UV light status indicator 196, one or more rechargeable batteries 109, a decontamination chamber 110, one or more UVC light isolation screens 111 and 114, one or more air filter cartridges 112, several sets of dampers 113 and 117, one or more electric heating coils 136, one or more air temperature sensors 131, a UV Light on/off switch 122, and/or an air pressure differential sensor 139. The air breathing device 100 may include a USB port 410 (FIG. 4D).

The air breathing device 100 of FIGS. 14-17C may include one or more additional components, such as, one or more ear pods or similar audio devices 123, a rear camera lens 124, a fixed display screen 126, a forward camera lens 127, a retractable display screen 128, an opening 119 for the retractable screen, an audio speaker 120, a microphone 121, a flashlight 125, a processor 140, computer readable media 141, one or more wireless transceivers 130, a GPS receiver 129, and/or a camera lens 197 directed to the wearer's mouth.

With reference to FIGS. 14-17C, the air breathing device 100 may include one or more wireless transceivers 130. The wireless transceiver(s) 130 may include a cellular transceiver, a Wi-Fi transceiver, and/or a Bluetooth transceiver to provide connection to one or more networks and/or to one or more external electronic devices. The GPS receiver 129 may be configured to receive the air breathing device's location from one or more satellites. The air breathing device 100 may include an assisted GPS (A-GPS) (not shown) to receive assistance data from a networked server to improve the startup performance of the GPS receiver and/or to save power. The network connections may allow the processor 140 to communicate with one or more external electronic devices and function as an IoT device.

The air breathing device 100, in some embodiments, may include one or more car pods or similar audio devices 123 (FIG. 17A), which may be located on the harness 106 (as shown) or may be located on the casing 102 (not shown). The air breathing device 100, in some embodiments, may include a microphone 121 and one or more audio speakers 120. Since the air breathing device 100 covers the mouth of the wearer, any conversation through the air breathing device 100 may be difficult or hard to understand. To facilitate conversation through the air breathing device 100, the microphone 121 may be installed inside the air breathing device 100, and one or more audio speakers 106 may be installed on the outside of the air breathing device 100. The audio speaker(s) 106, in some embodiments, may play the sounds captured by the microphone 121. The air breathing device 100 may also include one or more flashlights 125 (only one is shown). The flashlight(s) 125, in different embodiments, may be turned on or off by different mechanisms. For example, the flashlight(s) 125 may be turned on or off by turning, pushing, or by using an on/off switch (not shown). The flashlight(s) 125, in some embodiments, may be turned on or off in response to receiving one or more signals from an external electronic device.

The air breathing device 100, in some embodiments, may include a retractable flat or curved display screen 128 to display information to the wearer and a fixed display screen 126 to display information to others. The retractable display screen 128 is shown in FIGS. 14-17C as being extended to the wearer's eye level. The display screen 128 may be retracted in a corresponding opening 119 when the display screen 128 is not being used.

The retractable display screen 128 may enable the wearer to view content through networks, such as, the Internet. For example, the processor 140 may receive content (e.g., text, images, videos, etc.) through the wireless transceiver(s) 130 and may display the content on the display screen 128.

The following are several non-limiting examples of the retractable screen 128 and technologies used to project contents on the retractable screen of some embodiments. The retractable display screen 128, in some embodiments, may be a transparent display (e.g., a head-up display (HUD)) to allow the wearer to see through the screen 128. The retractable display screen 128, in some embodiments, may be Liquid Crystal on Silicon (LCOS), which is a miniaturized reflective active-matrix LCD. The retractable display screen 128, in some embodiments, may include several lenses that point images into the air breathing device 100 wearer's eyes.

The retractable display screen 128, in some embodiments, may include adjustable opacity, which may help adding focus to a video, or aid visibility on a bright day. For example, the retractable display screen 128 may include Polymer Dispersed Liquid Crystal (PDLC), which may include two layers of transparent conductive indium tin oxide (ITO) films with polymer dispersed liquid crystal in between. The opacity may be controlled by a switch or a knob (not shown).

The air breathing device 100, in some embodiments, may include a fixed display screen 126 (e.g., and without limitations, a liquid crystal display (LCD) screen). The air breathing device 100 covers the mouth of wearer, making the communication with other people difficult. The fixed display screen 126 may enhance communication between the wearer and other persons through the camera lens 197 mounted inside the air tube 147 to view the wearer's lips.

Figure 17D:
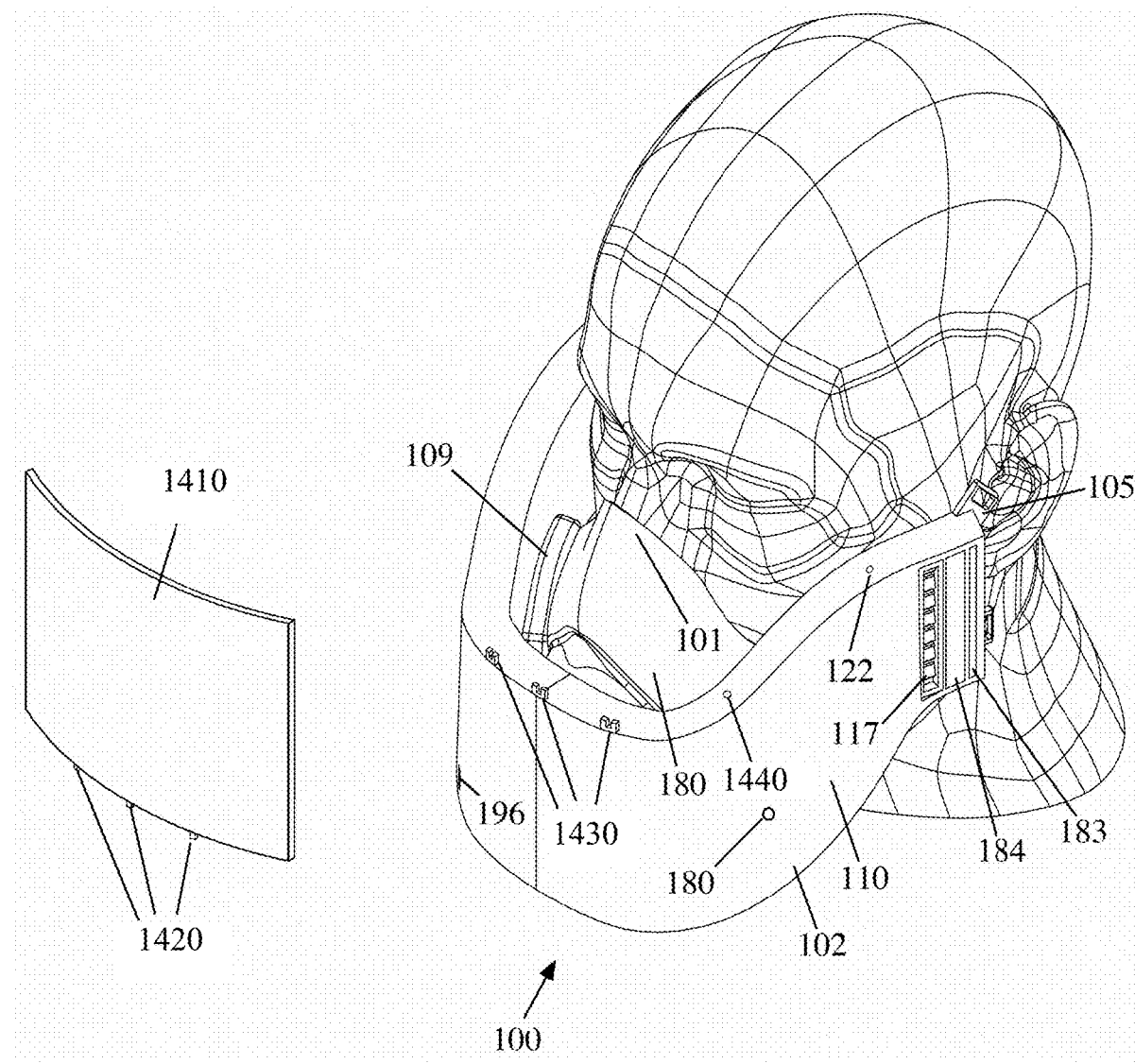
FIG. 17D is a front and side perspective view of an air breathing device with a detachable display screen, according to various aspects of the present disclosure.

The air breathing device 100, in some embodiments, may include a detachable display screen. FIG. 17D is a front and side perspective view of an air breathing device with a detachable display screen, according to various aspects of the present disclosure. The air breathing device 100 of FIG. 17D may include similar components as the air breathing device 100 of FIGS. 14-17C, except the air breathing device 100 of FIG. 17D may include a detachable screen 1410.

The detachable screen 1410 may include one or more connectors 1420 that may connect the detachable screen to one or more connectors 1430 on the casing 102 of the air breathing device 100. The detachable screen 1410 may be connected to the battery (or batteries) 109 of the air breathing device through several wires that may go through the connectors 1420 and 1430. The air breathing device 100 may include a release button 1440 on the casing 102 to release the detachable screen 1410. The processor of the air breathing device may receive content from one or more electronic devices external to the air breathing device, through the wireless transceiver of the air breathing device, and may display the content on the retractable display screen.

The detachable display screen 1410, in some embodiments, may be a transparent display (e.g., a HUD) to allow the wearer to see through the screen 1410. The detachable display screen 1410, in some embodiments, may be LCOS. The detachable display screen 1410, in some embodiments, may include several lenses that point images into the air breathing device 100 wearer's eyes.

The detachable display screen 1410, in some embodiments, may include adjustable opacity, which may help adding focus to a video, or aid visibility on a bright day. For example, the detachable display screen 1410 may include PDLC, which may include two layers of transparent conductive ITO films with polymer dispersed liquid crystal in between. The opacity may be controlled by a switch or a knob (not shown).

In some embodiments, the camera lens 197 may capture videos or images while the person is speaking. The processor 140 may receive the videos and/or images from the camera lens 197 and may display the videos and/or images on the fixed display screen 126. In addition to, or in lieu of using the camera lens 197, the processor 140 may generate images of the wearer's lips on the fixed display screen 126 based on the wearer voice captured by the microphone 121. For example, the microphone 121 may capture the wearer's voice, the processor 140 may convert the voice into simulated lip movements, and the processor 140 may display the simulated lip movements to the fixed display screen 126.

The fixed display screen 126 may be mounted in front of the air breathing device 100. For example, the fixed display screen 126 may be located on the center of the surface of the casing that is opposite to the face of the wearer and may be positioned to be visible by persons facing the wearer's face. The fixed display screen 126 may also be used for displaying other content such as displaying text messages, emojis, augmented reality, multimedia content, etc. For example, the processor 140 may receive the text messages, emojis, augmented reality, multimedia content, etc., from external electronic devices that may communicate with the air breathing device processor 140 through one or more of the transceivers 130. The processor 140 may display the received content on the fixed display screen 126.

The air breathing device 100, in some embodiments, may include a rear facing camera 124 mounted on the harness 106. The rear view captured by the rear facing camera 124 may be observed through the retractable display screen 128. The rear facing camera 124 may be installed on the straps 106, as shown in FIG. 17A.

It should be noted that the air breathing devices of some embodiments may not include the UV light sources 108, may not include the dampers 113, 117, or may include neither the UV light sources 108 nor the dampers 113, 117. These embodiments may include one or more of the other components disclosed herein, such as, for example and without limitations, the air filter cartridge 112, the speaker 120, the microphone 121, the ear pods (or similar audio devices) 123, the rear camera lens 124, the flashlight, 125, the fixed display screen 126, the forward camera lens 127, the retractable display screen 128, and/or the heating coil 134.

The embodiments that do not include the UV light sources 108 may not include the UVC light isolation screens 111, 114, the UVC Light on/off switch 122, and the UV light status indicator 196. The embodiments that do not include motorized dampers 113, 117 may not include the optional motor(s) 600 (FIG. 6), the rotating shaft(s) 610, the linear movement converter(s) 620, and the rod(s) 660. Furthermore, the embodiments that do not include the dampers 113, 117 may not include separate air intake 137 and air discharge 138 ports. For example, some of these embodiments may include the port(s) 137 (but not the port(s) 138) and may use the port(s) 137 for both air intake and air discharge. Some of these embodiments may include the port(s) 138 (but not the port(s) 137) and may use the port(s) 138 for both air intake and air discharge. In these embodiments, the air filter cartridge 112 and the heating coil 136 may be located anywhere between the opening of the port 138 and the air tube 147.

Figure 18:
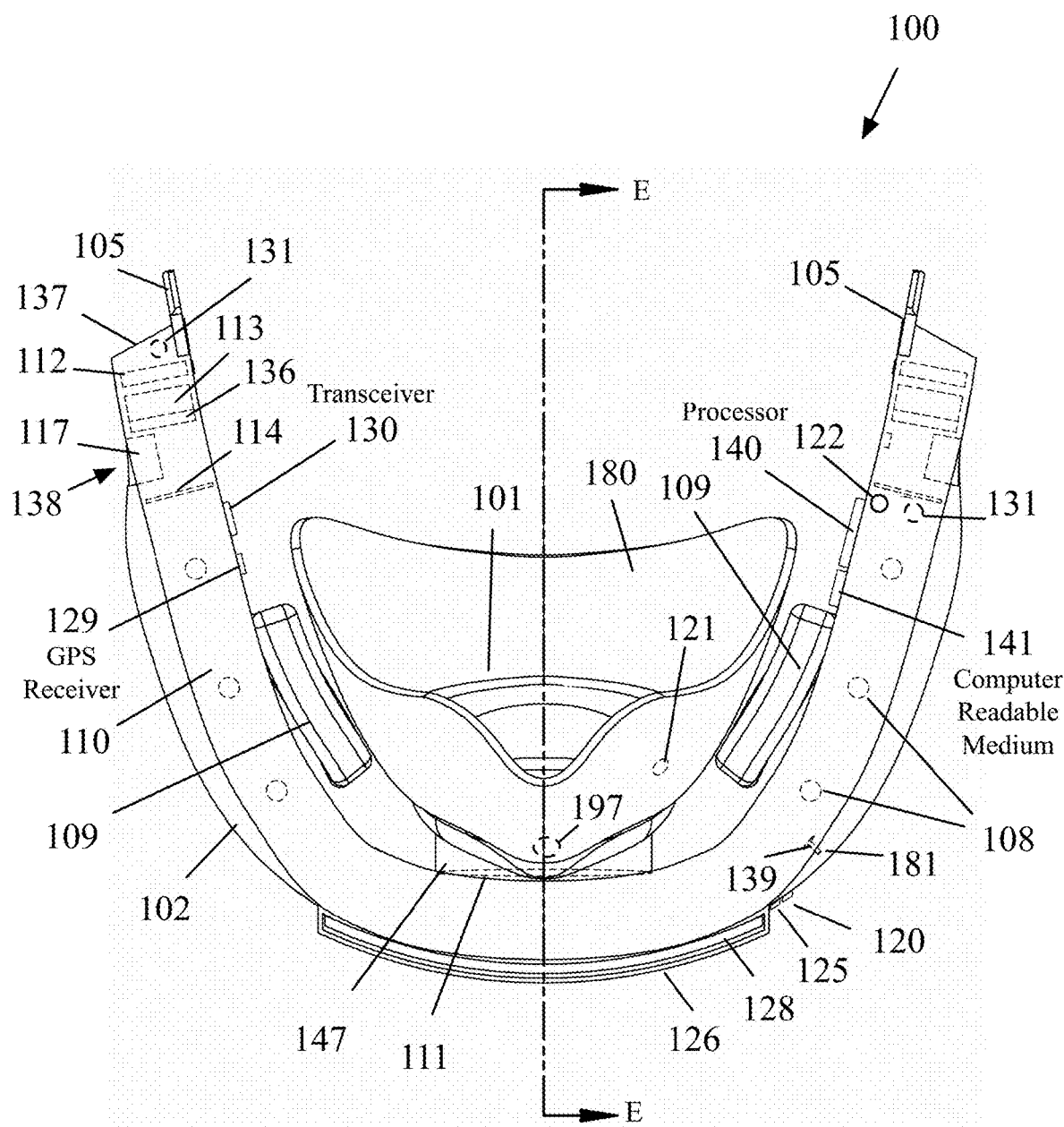
FIG. 18 is a top view of the reusable purified air breathing device of FIG. 14, illustrating different components of the air filtration and sterilization of the air breathing device, according to various aspects of the present disclosure.
Figure 19:
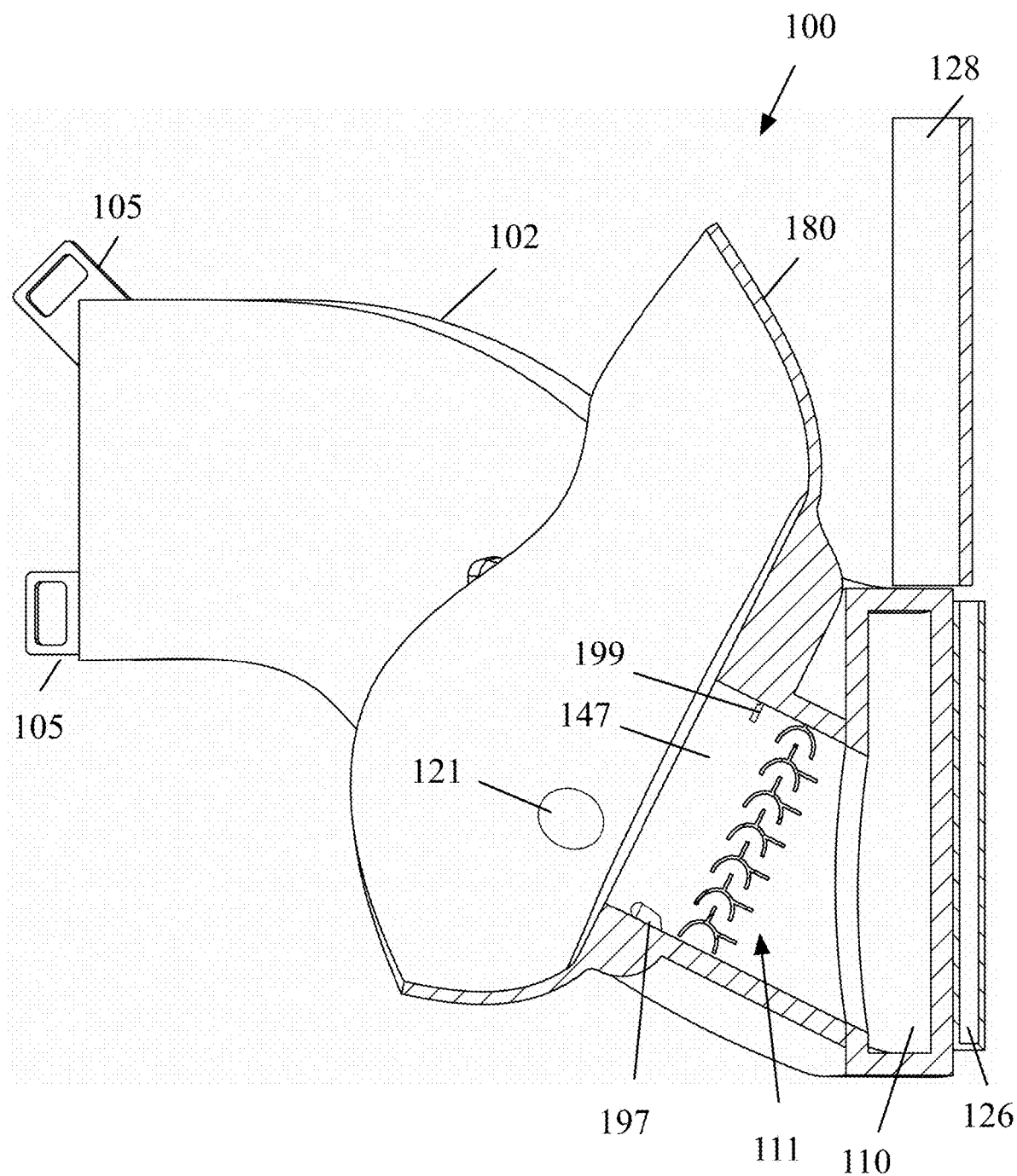
FIG. 19 is a side cross sectional view of the reusable purified breathing air device along the line E-E shown in FIG. 18, according to various aspects of the present disclosure.

FIG. 18 is a top view of the reusable purified air breathing device of FIG. 14, illustrating different components of the air filtration and sterilization of the air breathing device 100, according to various aspects of the present disclosure. FIG. 19 is a side cross sectional view of the reusable purified breathing air device along the line E-E shown in FIG. 18, according to various aspects of the present disclosure.

FIG. 18 shows components similar to the cross sectional view of FIG. 9. In addition, FIG. 18 illustrates the microphone 121, the fixed display screen 126, the retractable screen 128, the GPS receiver 129, the wireless transceiver(s) 130, the processor 140, the computer readable media 141, and the camera lens 197 that is directed to the wearer's mouth. Some of the components shown on FIG. 18 such as the GPS receiver 129, wireless transceiver(s) 130, the processor 140, and the readable media 141 may be located outside or inside of the air breathing device 100 in different embodiments.

FIG. 19 shows components similar to the cross sectional view of FIG. 10. In addition, FIG. 19 illustrates the microphone 121, the fixed display screen 126, the retractable screen 128, the camera lens 197 that is directed to the wearer's mouth, and a light source 199. The light source 199 may be, for example, and without limitations, one or more a LEDs that may illuminate the wearer's mouth of the wearer. The camera 197 may capture the movements of the wearer's lips. The processor 140 of the air breathing device 100 may display the live video captured by the camera 197 on the fixed display 126. Since the wearer's mouth is hidden behind the casing 102, displaying the lips movements on the fixed display screen 126 may help other people to better understand what words that the wearer is conversing.

In should be noted that the external electronic devices that communicate with the air breathing device 100 may include one or more processors and computer readable media. The computer readable media of the external electronic devices may include different types of memory units, such as, read-only-memory, volatile read-and-write memory, and/or non-volatile read-and-write memory. The read-only-memory may store static data and instructions that are needed by the processor. The non-volatile read-and-write memory may store instructions and data even when the power to the non-volatile memory is off. Some embodiments may use a small mass-storage device (such as a magnetic or optical disk and its corresponding disk drive) as the non-volatile read-and-write memory.

The volatile read-and-write memory of the external electronic devices may be random access memory and may be used as system memory. The system memory may store some of the instructions and data that the processor needs at runtime. From these various memory units, the processor of the external electronic devices may retrieve instructions to execute, and data to process, in order to execute and control different electronic components of the external electronic devices and to participate in some of the processes of some embodiments.

In the embodiments of FIGS. 1-19, the air breathing device 100 is a half face air breathing device that covers the nose, the mouth, and the chin of the wearer. In other embodiments, the air breathing device may be a full face air breathing device. In these embodiments, the air breathing device may cover the head and the neck of the wearer and may form a hood, or a helmet, around the wearer's head. The full face air breathing device of some embodiments may not include the retractable screen 128, the opening 119 for the retractable screen, the harness 106 and/or the harness handles 105. In some embodiments, the ear plugs 123 may be installed inside the hood or helmet of the full face air breathing device. In some embodiments, the rear view camera lens 124 may be installed on the outside and back of the hood of the full face air breathing device.

Figure 20:
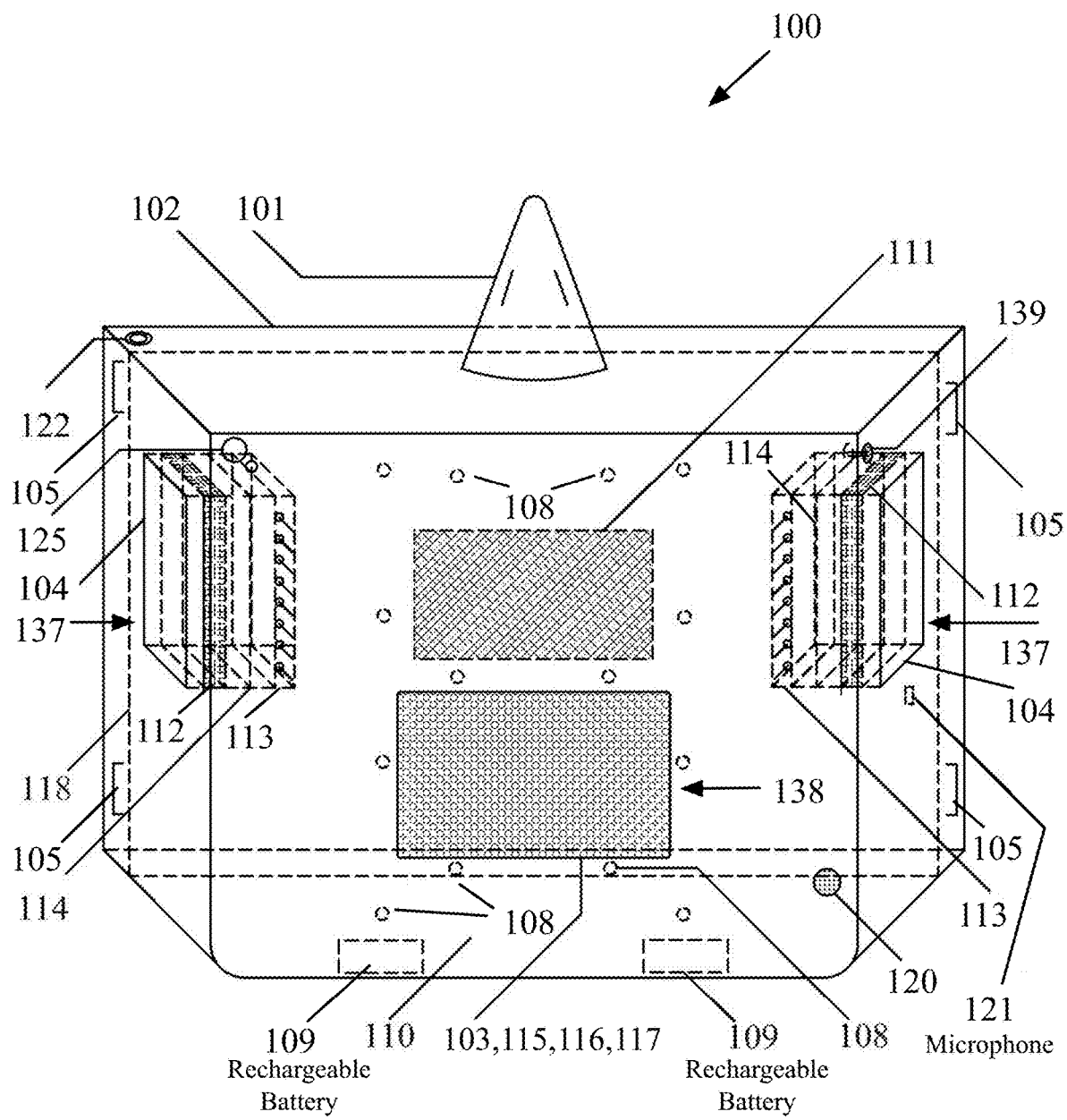
FIG. 20 is a perspective view of a reusable purified air breathing device, according to various aspects of the present disclosure.
Figure 21:
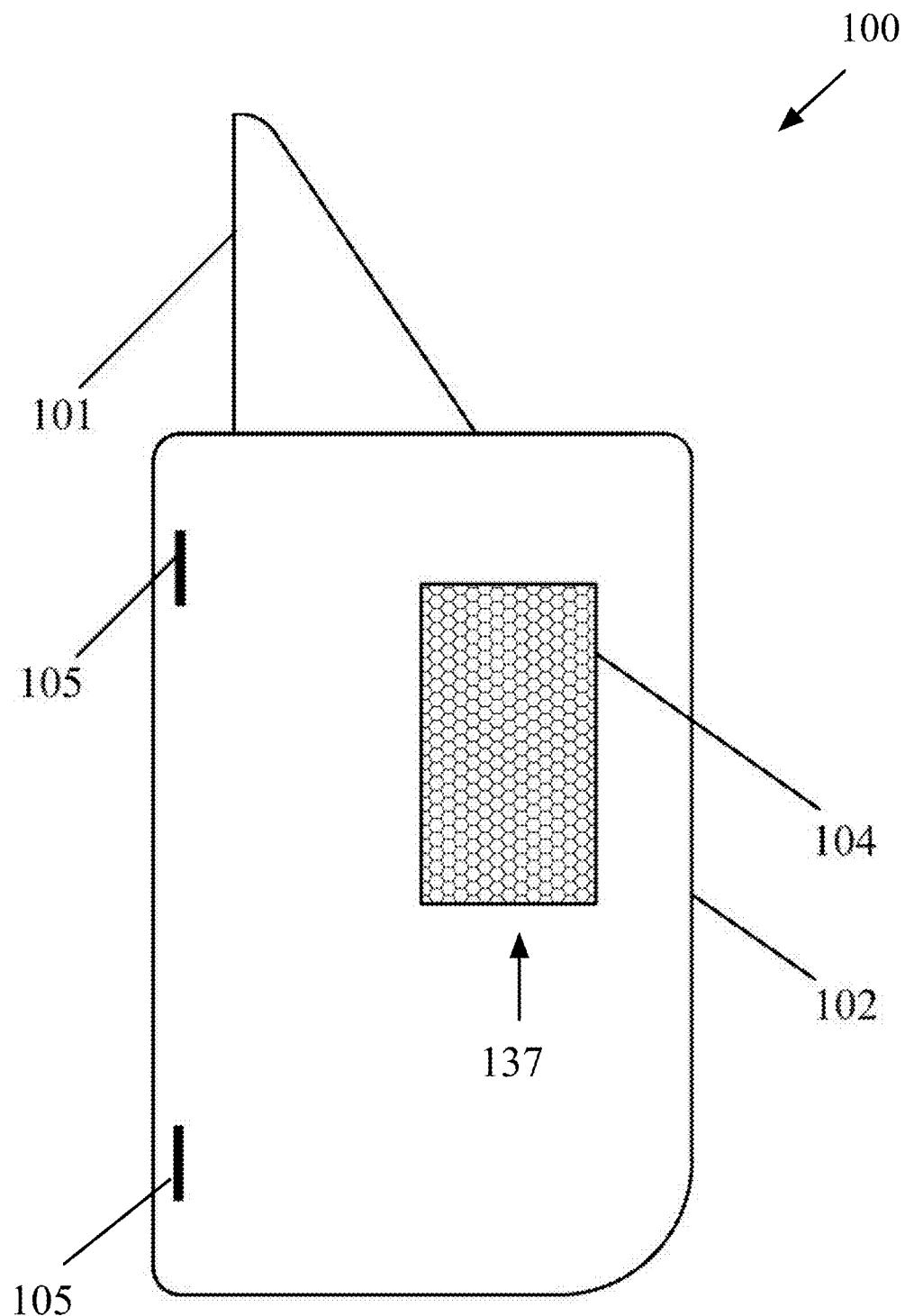
FIG. 21 is a side elevation view.
Figure 22:
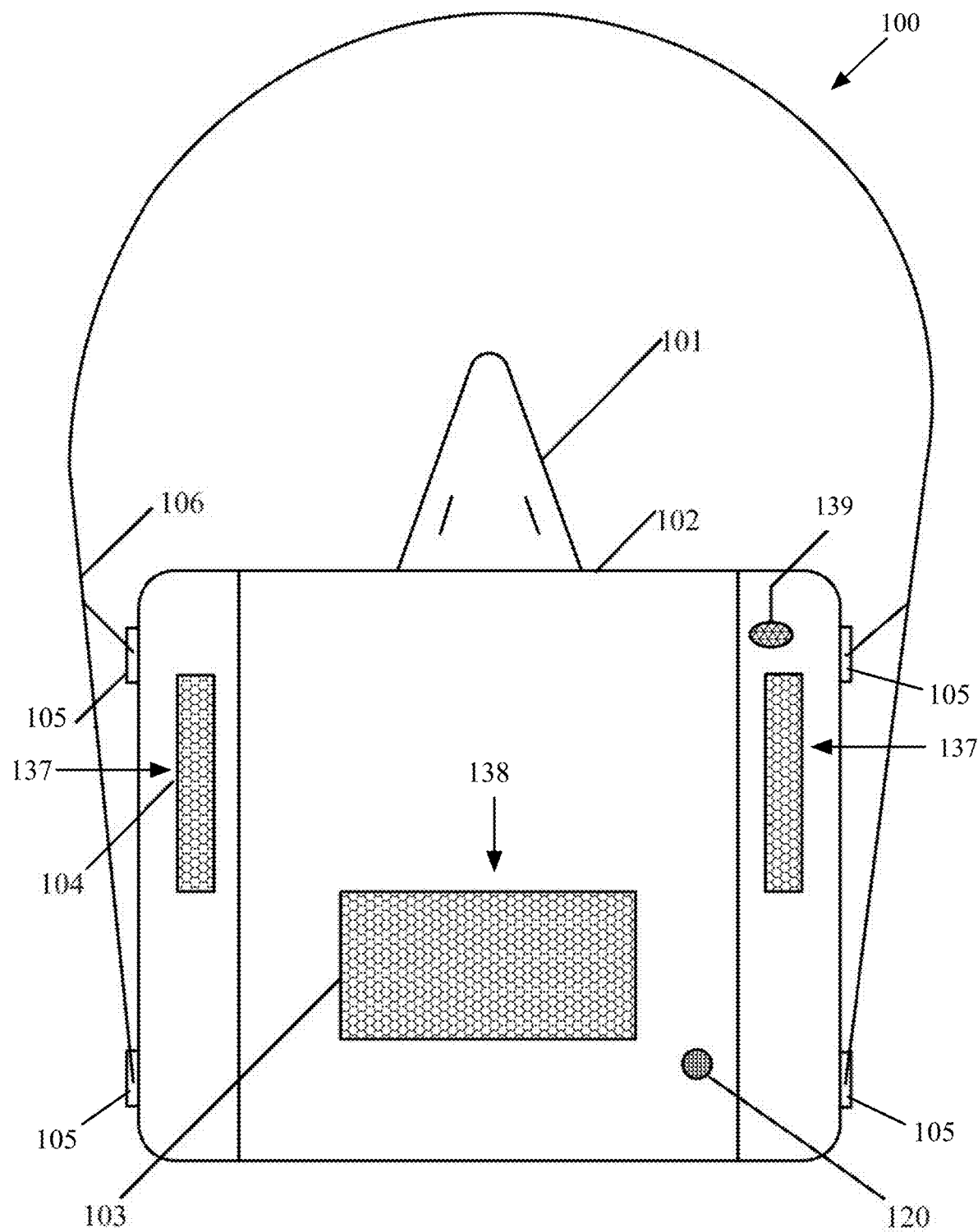
FIG. 22 is a front elevation view.
Figure 23:
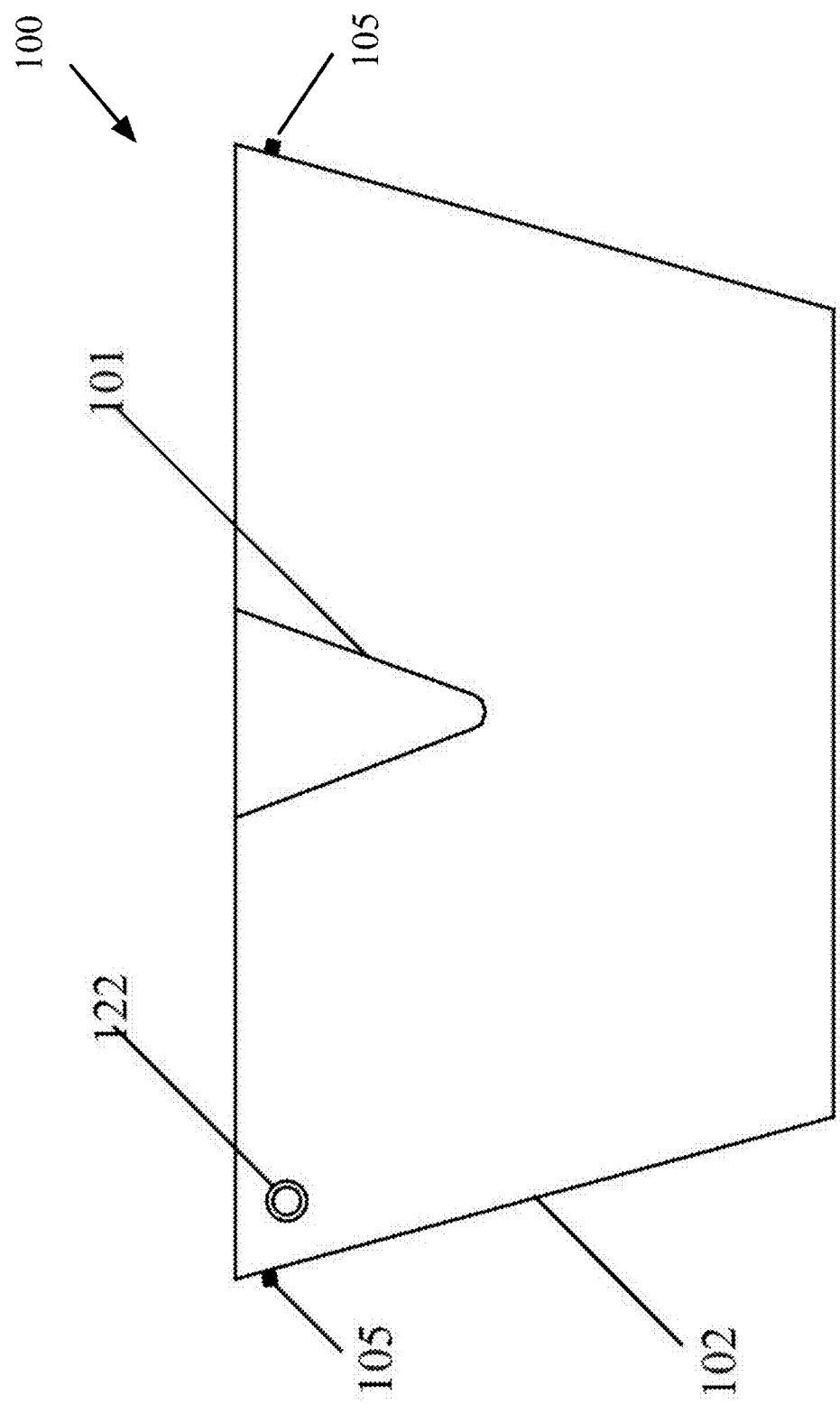
FIG. 23 is a top view of the reusable purified air breathing device of FIG. 20.

The following is another alternative embodiment of the reusable purified air breathing device of the present embodiments. FIG. 20 is a perspective view of a reusable purified air breathing device, according to various aspects of the present disclosure. FIG. 21 is a side elevation view, FIG. 22 is a front elevation view, and FIG. 23 is a top view of the reusable purified air breathing device of FIG. 20. FIGS. 21-23 only show the components of the air breathing device 100 that are visible from the outside of the air breathing device 100.

With reference to FIGS. 20-23, the air breathing device 100 may include a nose enclosure 101, a casing 102, one or more breathing air discharge screens 103, one or more breathing air entry screens 104, several harness handles 105, a harness 106 (FIG. 22), one or more UV light sources 108, one or more rechargeable batteries 109, a decontamination chamber 110, one or more UVC light isolation screens 111 and 114, and 116, one or more air filter cartridges 112, several sets of dampers 113 and 117, one or more discharge air filters 115, one or more isolation elastic membranes 118, one or more audio speakers 120, a microphone 121, a UVC Light on/off switch 122, a flashlight 125, and/or an air pressure differential sensor 139.

With reference to FIGS. 20-23, the air breathing device's casing 102 may be made of a material, such as, for example, and without limitations, hard plastic. The exterior of the casing may be thermally insulated by a layer of insulating material, by injected foam insulation, or by other material and methods. For example, in some embodiments, the body of the casing 102 may include a cavity close to the exterior of the casing 102, and foam insulation may be injected into the cavity during the manufacturing of the casing 102. In some embodiments, the exterior of the casing 102 may include a layer of insulating material. The back side of the air breathing device, close to the face of the wearer may not be insulated.

The nose enclosure 101 may be configured to enclose the nose of a person that wears the air breathing device 100 (this person is referred to herein as the wearer). The air breathing device 100 may include a lining at the edges of the casing 102 where the casing 102 comes into contact with the wearer's face. The lining may be made of soft and flexible material such as, for example, and without limitations, silicone, to make the air breathing device 100 airtight and to protect the wearer's face against the rigid casing material.

The casing 102, the lining, and/or the nose enclosure 101, in some embodiments, may be made in different sizes to match the faces of different persons. For example, and without limitations, the air breathing device 100 may be made in different sizes, such as, extra small, small, medium, large, extra-large, etc. Each size may come with an appropriate size of casing, lining, and/or nose enclosure.

The lining. in some embodiments, may be customized to fit an individual person's face contours. For example, an external computer system at a point of sale, or at an establishment, such as, for example, and without limitations, a hospital, a factory, a military facility, etc., may be used to measure an individual person's face contours. Next, the computer may identify an air breathing device size that best fits the individual person's face. The computer may then select one of many different sizes of linings for the selected air breathing device size to further fit the air breathing device to the person's face.

It should be noted the casing 102 in different embodiments may have different shapes and/or different contours. For example, in FIG. 20, the front and the four sides of the casing 102 are shown as substantially rectangular pieces. In other embodiments, the front and/or the sides of the casing 102 may be curved towards the back (towards the face of the wearer) in order to facilitate the lining to better fit to the contours of a person's face. Accordingly, the present embodiments are not limited to the exemplary shape of the casing 102 shown in FIG. 20.

The air breathing device 100 may include one or more air intake ports 137, each air intake port 137 may be covered by a breathing air entry screen 104. The air breathing device 100 may include one or more air discharge ports 138 (only one air discharge port is shown), each air discharge port 138 may be covered by one or more breathing air discharge screens 103.

Figure 24:
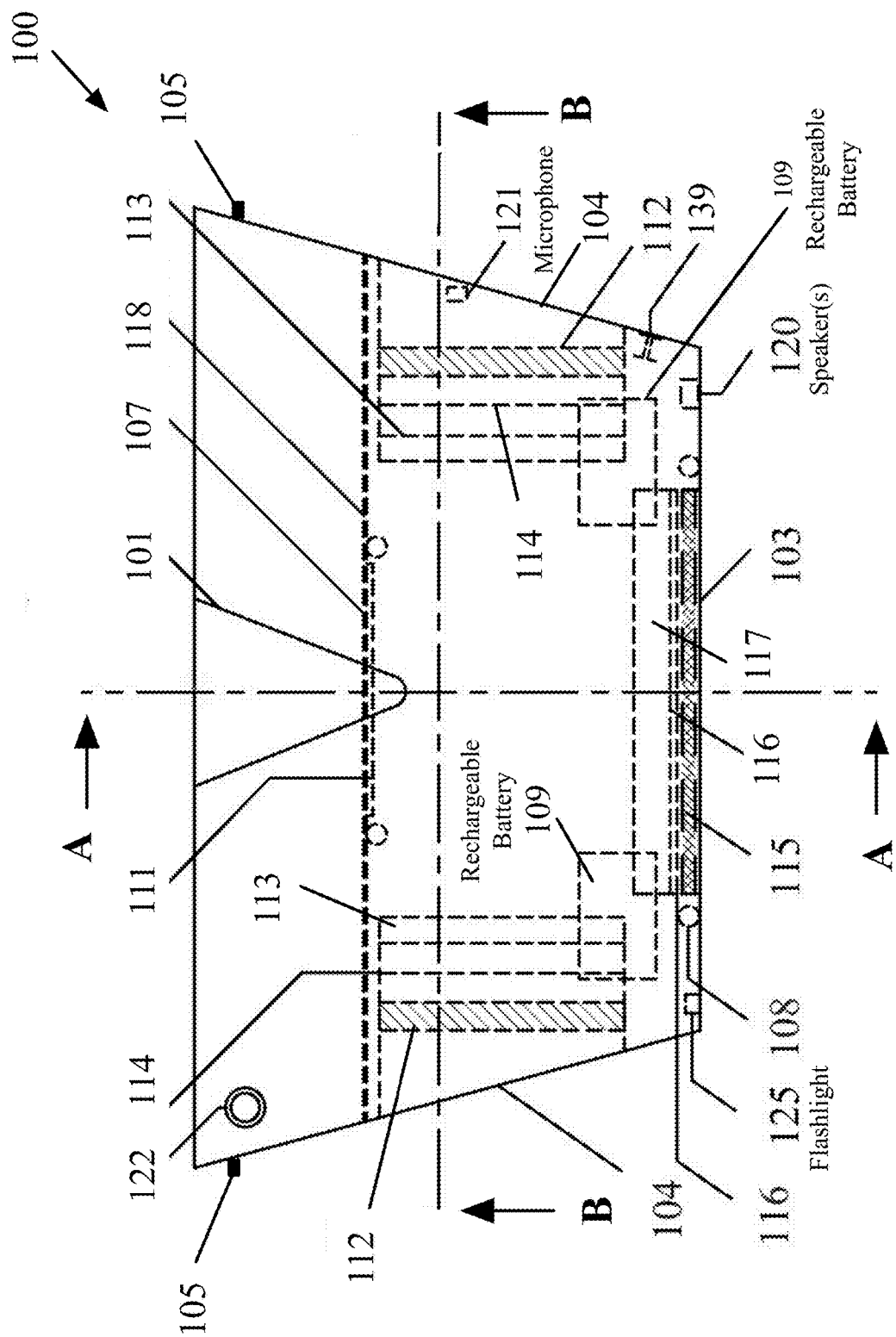
FIG. 24 is a top view of the reusable purified air breathing device of FIG. 20, illustrating the different components of the air filtration and sterilization of the air breathing device, according to various aspects of the present disclosure.
Figure 25:
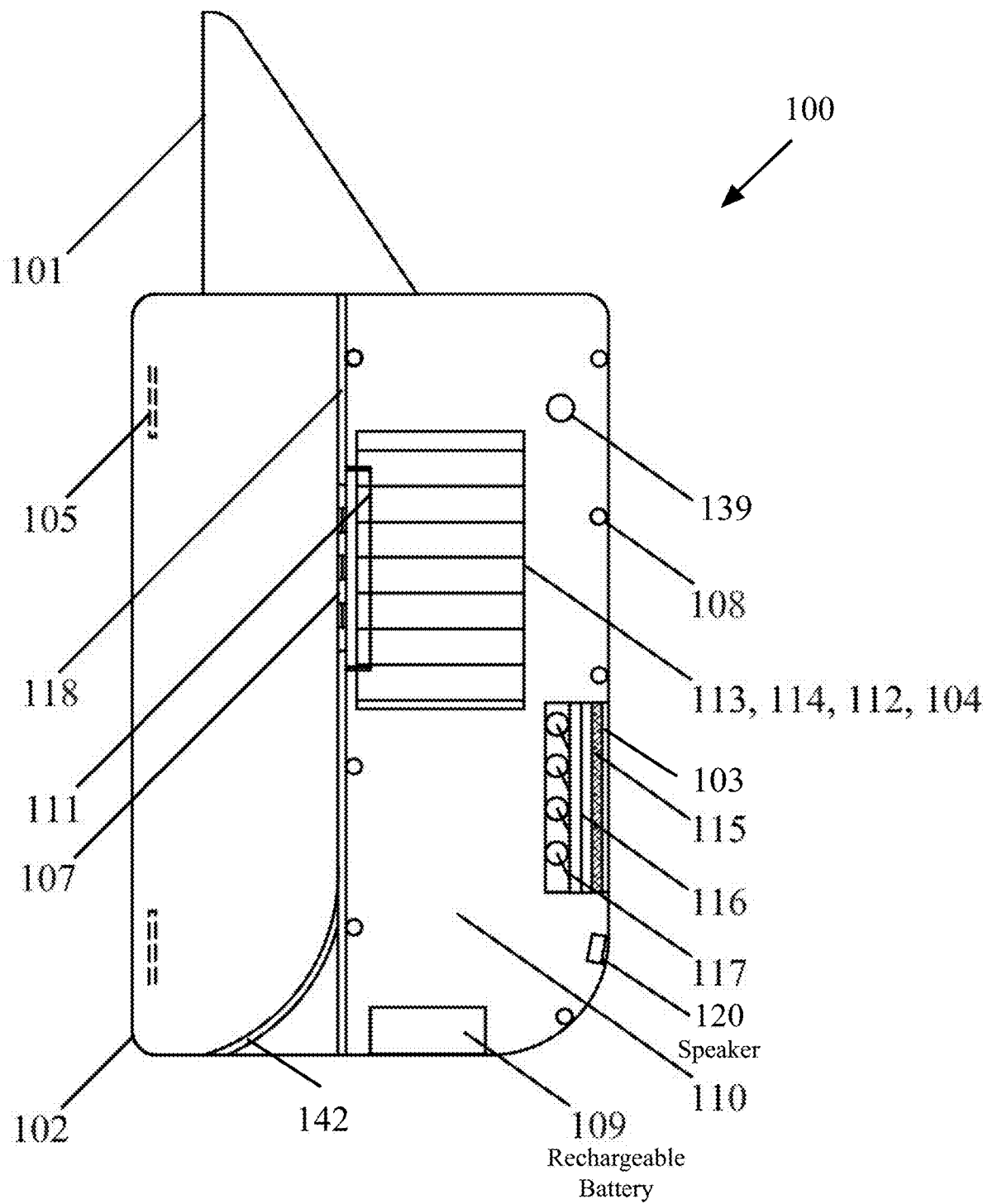
FIG. 25 is a side cross sectional view of the reusable purified breathing air device along the line A-A shown in FIG. 24.

The air breathing device 100 may include several sets of dampers 113 and 117. In the perspective view of FIG. 20, the dampers 117 are located behind the breathing air discharge screen 103. Further details of the dampers 117 are shown in FIGS. 24 and 25. The dampers 113 and 117 are configured to open and close in response to the difference between the air pressure inside of the casing 102 and the air pressure outside of the air breathing device 100. The intake dampers 113 are hinged towards the inside of the casing 102 and the discharge dampers 117 are hinged towards the outside of the casing 102. During air inhalation, the air pressure inside the casing 102 is lower than the outside air pressure. The intake dampers 113, during the inhalation, open up and only allow the air into the air breathing device 100. The discharge dampers 117, during the inhalation process, are in close position and do not allow the air to enter into, or exit from, the air breathing device 100 through the air discharge port 138.

During the air exhalation, the air pressure inside the casing 102 is higher than the outside air pressure. The discharge dampers 117, during the exhalation, open up and only allow the air to leave the air breathing device 100. The intake dampers 113, during the exhalation, are in close position and do not allow the air to enter into, or exit from, the air breathing device 100 through the air intake ports 137.

The dampers 113 and 117 are, therefore, configured, such that the breathing air may only enter into the air breathing device 100 through air intake ports 137, and may leave the air breathing device 100 through the discharge port 138. The dampers 113 and 117 provide the technical advantage of controlling the path of breathing air when the air is being inhaled and exhaled.

Some embodiments may use motorized dampers. In these embodiments, the path of the breathing air is controlled through the use of motorized dampers. The motorized dampers may be controlled based on the measurements made by the air pressure differential sensor 139 located on the casing 102 of the air breathing device 100 with openings to both the inside and the outside of the casing 102. The air pressure differential sensor 139 may be configured to measure the difference between the air pressure inside and outside of the casing 102.

With continued reference to FIGS. 20-23, the air breathing device 100 may include one replaceable air filter cartridge 112 at each air intake port 137. The air filter cartridges 112 may include a particulate filter and a carbon filter combined into one cartridge. The particulate filters may be made of fibrous or porous material, and may be configured to capture (e.g., through electrostatically charged fibers, such as, for example, and without limitations, poly-propylene, or other material) particulates such as dust, pollen, mist, fumes, and smoke. The particulate filters may be configured to filter oil based particles and non-oil based particles.

The carbon filter may be configured to filter gases through a bed of activated carbon (activated charcoal). The carbon filter may remove odors and gaseous pollutants such as volatile organic compounds or ozone. In addition to, or in lieu of, the air filter cartridges 112 that include both particulate and carbon filters, some embodiments may include individual particulate filters and/or individual carbon filters. The discharge port 138 may be equipped with a replaceable particulate filter 115 to protect the discharge dampers 117 from ambient particulates.

The filters of the present embodiments may be configured to suit different applications such as, medical, industrial, and/or personal use. Some of the present embodiments may require the filters to be replaced after a period of time, for example, after several days, several weeks, several months, etc. In some embodiments, the air pressure differential sensor 139 measurements may be used to determine whether the air filters need to be changed. For example, the air filters may need to be changed when the air pressure differential sensor 139 measurements exceed a threshold over a period of time. As described below, some embodiments may include a processor that may provide air filter replacement warnings and/or may control the motorized dampers based on the measurements received from the air pressure differential sensor 139.

Since the prior art respirators rely solely on heavy duty filters to cleanse and disinfect the air, the prior art respirators have high air pressure drops, which makes breathing difficult for the wearers. The breathing air devices of the present embodiments use the UVC light to disinfect the air and kill and/or disable harmful microorganisms and do not rely on heavy duty air filters to disinfect the air. The breathing air devices of the present embodiments provide the technical advantage of using air filters with relatively low air pressure drop, in conjunction with the cleansing action of the UVC light rays, that make it easier for the wearers to breath than the prior art respirators.

With continued reference to FIGS. 20-23, the air breathing device 100 may include one or more UV light sources 108 (shown as small round circles in FIG. 20). For clarity, only some of the UV light sources are labeled and/or shown in FIG. 20. The UV rays have sterilization and disinfection effects by destroying the molecular structure of DNA and RNA in microorganisms, such as viruses, bacteria, and fungi, resulting in growth cell death and/or regenerative cell death. The UV rays are divided into A, B, C, and D bands, and the microorganisms disinfection effect is most effective in the C band (UVC) with a wavelength of 200-280 nm (nanometer), which may destroy microorganisms' DNA. The UVC light and the air filter cartridges 112 and 115 may create a decontamination chamber 110 inside the casing 102 of the air breathing device 100.

In some embodiments, the interior surface of the air breathing device's casing 102 may be embedded with one or more of the UV light sources 108 that may expose both incoming and leaving air (in and out of the air breathing device) to UVC light to sterilize and disinfect the air to avoid the spread of deceases. As described below, the air breathing device 100 is configured to totally encapsulate the UV rays, such that the skin, mouth, or eyes of the wearer are not exposed to UV rays, and the UV rays may not leave the casing 102 and enter into the surrounding area.

The UV light sources 108 may be powered by one or more on-board rechargeable batteries (e.g., and without limitations, lithium ion batteries) 109, and/or powered through an external source via a USB port mounted on the casing 102. Power through the USB port may be used, for example, and without limitations, when the wearer is sitting in an airplane chair or in an office chair over an extended period of time.

The UV light sources 108 may be turned on or off by a UV Light on/off switch 122. For example, in an environment where there is little or no danger of microorganism exposure, the UV light sources 108 may be turned off and the air breathing device 100 may be used to protect the wearer from dust, fumes, noxious gases, etc., that may be generated during various tasks.

The air breathing device 100 may include several screens and/or membranes to confine the UV rays inside the casing 102, to prevent the UV rays from reaching the wearer, and to prevent the UV rays from entering the surrounding area. The air breathing device 100 may include one or more UVC light isolation screens 111, 114, and 116, and/or one or more isolation elastic membranes 118. The isolation elastic membrane 118 may be configured to isolate the UV light in the interior of the casing 102 and prevent the UV light to leak out of the back side of the casing 102 towards the face of the wearer. The isolation elastic membranes 118, in some embodiments, may be made of semi soft material in order to enable some of the UV light sources 108 to be mounted on the isolation elastic membranes 118. For comfort of the wearer, the isolation elastic membrane 118 may be configured such that there is a small gap between the membrane 118 and the face of the wearer.

The UVC light isolation screen 111 may be configured to prevent the mouth of the wearer from being exposed to the UV light. The air breathing device 100 may include one or more slot openings 107 (shown in FIGS. 24-26) that may be configured to bring air through an opening in the isolation elastic membrane 118 into the wearer's mouth. The UVC light isolation screen 111 may be positioned between the slot openings 107 and the interior of the casing 102 to prevent the UV light to leak into the wearer's mouth. Further details of the slot openings 107, the UVC light isolation screen 111, and the isolation elastic membranes 118 are described below with reference to FIG. 25.

The UVC light isolation screens 114 may be configured to prevent the UV light from leaking to the outside of the casing 102 through the air intake ports 137. The UVC light isolation screen 116 may be configured to prevent the UV light from leaking to the outside of the casing 102 through the air discharge port 138. In the perspective view of FIG. 20, the breathing air discharge screen 103, the discharge air filter 115, the UVC light isolation screen 116, and the dampers 117 are shown to, respectively, cover each other. The casing 102, the isolation elastic membrane 118, the UVC light isolation screens 111, 114, and 116 completely confine the UV rays inside the casing 102 and prevent the UV rays from reaching the wearer and from entering the surrounding area.

The air breathing device 100 may include a harness 106 (FIG. 22). For clarity, the harness is not shown in FIGS. 20-21 and 23. The harness 106 may be configured to secure the air breathing device 100 behind the head and neck of the wearer. Although the harness 106 is shown as having one band, the harness 106, in some embodiments, may be made of more than one band. The harness 106, in some embodiments, may be made of soft and flexible material. The harness 106, in other embodiments, may be made of semi soft material to allow one or more accessories to be placed on the harness, as described below. The harness 106 may be connected to the casing 102 by one or more harness handles 105.

The air breathing device 100, in some embodiments, may include a microphone 121 and one or more audio speakers 120. Since the air breathing device 100 covers the mouth of the wearer, any conversation through the air breathing device 100 may be difficult or hard to understand. To facilitate conversation through the air breathing device 100, the microphone 121 may be installed inside the air breathing device 100, and one or more audio speakers 106 may be installed on the outside of the air breathing device 100. The air breathing device 100 may also include one or more flashlights 125 (only one is shown). The flashlight(s) 125, in different embodiments, may be turned on or off by different mechanisms. For example, the flashlight(s) 125 may be turned on or off by turning, pushing, or by using an on/off switch (not shown).

It should be noted that the number and the locations of different components of the air breathing device 100 may be different in different embodiments. As such, FIG. 20-32 only show examples of the number and the location of different components of the air breathing device 100. For instance, the number and the location of the UV light sources 108 may be different in different embodiments. Different embodiments may include one or more air intake ports 137, where each air intake port may include a breathing air entry screen 104, one or more air filter cartridges 112 (either a combined air cartridge or separate particulate and carbon filters), a UVC light isolation screen 114, and a set of air intake dampers 113. The air intake ports 137 may be located in front, and/or on the four sides (left, right, up, or down sides) of the casing 102.

Different embodiments may include one or more air discharge ports 138, where each air discharge port 138 may include a breathing air discharge screen 103, one or more air filter cartridges 115 (either a combined air cartridge or separate particulate and/or carbon filters), a UVC light isolation screen 116, a set of air discharge dampers 117. The air discharge ports 138 may be located in front, and/or on the four sides (left, right, up, or down sides) of the casing 102.

FIG. 24 is a top view of the reusable purified air breathing device of FIG. 20, illustrating different components of the air filtration and sterilization of the air breathing device, according to various aspects of the present disclosure. FIG. 24 illustrates different components of the air breathing device 100, such as the nose enclosure 101, the breathing air discharge screens 103, the breathing air entry screens 104, the harness handles 105, the slot openings 107, the UV light sources 108, the rechargeable batteries 109, the UVC light isolation screens 114, and 116, the air filter cartridges 112, the dampers 113 and 117, the discharge air filter cartridge 115, the isolation elastic membranes 118, the microphone 121, the UV Light on/off switch 122, and the air pressure differential sensor 139. For clarity, some of the UV light sources 108 are not shown and/or not labeled.

As shown in FIG. 24, the isolation screens 114 (each shown as a narrow line) are between the corresponding air filter cartridges 112 and the interior of the casing 102, allowing the air filter cartridges 112 to be changed even when the UV light sources 108 are on, without the UV light to leak to the outside of the casing 102. The isolation screen 116 is between the air filter cartridge 115 and the interior of the casing 102, allowing the air filter cartridge 115 to be changed even when the UV light sources 108 are on, without the UV light to leak to the outside of the casing 102.

Figure 26:
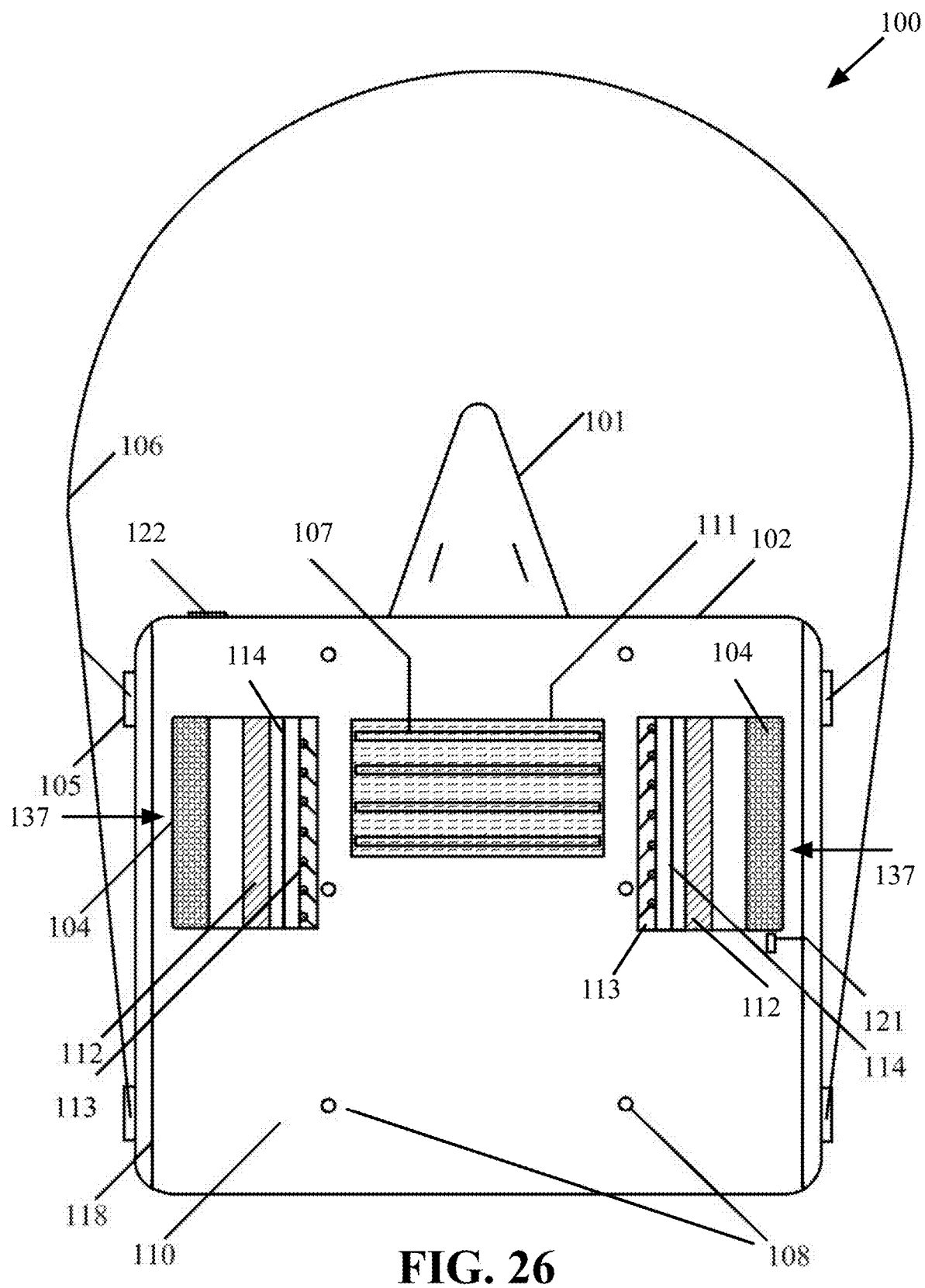
FIG. 26 is a front cross sectional view of the reusable purified air breathing device along the line B-B shown in FIG. 24, according to various aspects of the present disclosure.

FIG. 25 is a side cross sectional view of the reusable purified breathing air device along the line A-A shown in FIG. 24, and FIG. 26 is a front cross sectional view of the reusable purified air breathing device along the line B-B shown in FIG. 24, according to various aspects of the present disclosure. With reference to FIG. 25, the slot openings 107 may be located on the isolation elastic membrane 118, where the wearer may inhale and exhale the air through the slot openings 107. As shown in FIG. 25, the UVC light isolation screen 111 may be positioned between the slot openings 107 and the interior of the casing 102 to prevent the UV light to leak into the wearer's mouth. The air discharge port 138 may include the breathing air discharge screen 103, the discharge air filter cartridge 115, the UVC light isolation screen 116, and the discharge dampers 117. The chin support plate 142 may be made of soft material and may be configured to support the wearer's chin.

With reference to FIG. 26, each air intake port 137 may include a breathing air entry screens 104, an air filter cartridge 112, a UVC light isolation screen 114, and a set of intake dampers 113. The UVC light isolation screen 111 may be positioned between the slot openings 107 and the interior of the casing 102. One or more UV light sources 108 (shown by small circles) may be installed on the isolation elastic membrane 118 facing towards the interior of the casing 102. For clarity, some of the UV light sources 108 are not shown and/or not labeled in FIGS. 25 and 26.

In addition to, or in lieu of, some of the features, such as the flashlight 125, the speaker(s) 120, the microphone 121, etc., described above with reference to FIGS. 20-26, the air breathing device of some embodiments may provide connection to different networks, such as, for example, and without limitations, connection to the Internet, connection to cellular networks, a Wi-Fi connection, a Bluetooth connection, etc. The air breathing device, in some embodiments, may provide an air heating mechanism to warm up the air before being inhaled by the wearer. The air breathing device, in some embodiments, may function as an Internet of Things (IoT) device.

Figure 27:
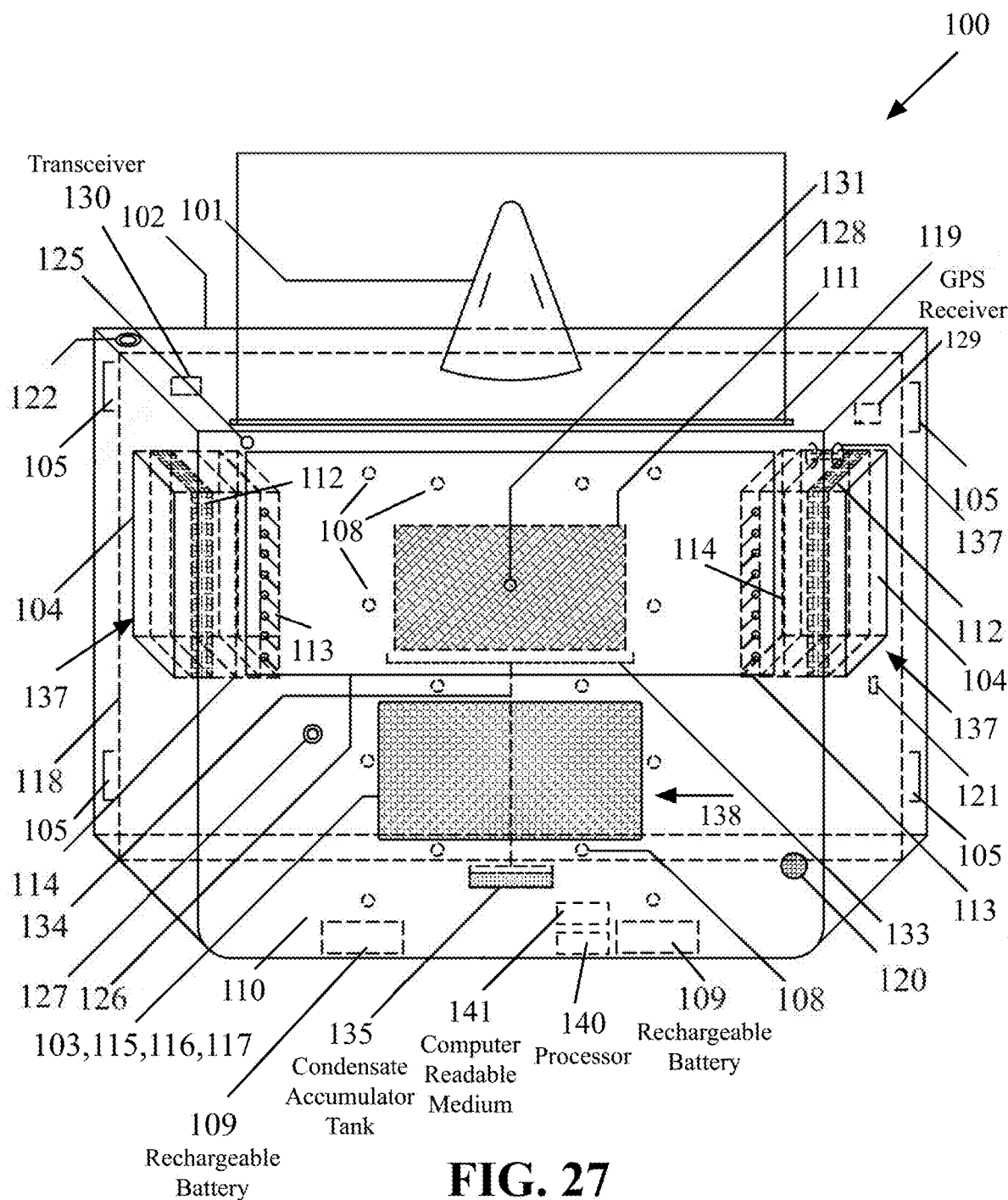
FIG. 27 is a perspective view of a reusable purified air breathing device that provides network connection, one or more cameras, one or more display screens, a GPS receiver, a cellular signal receiver, one or more Wi-Fi and/or Bluetooth receivers, and/or an air heating module, according to various aspects of the present disclosure.
Figure 28:
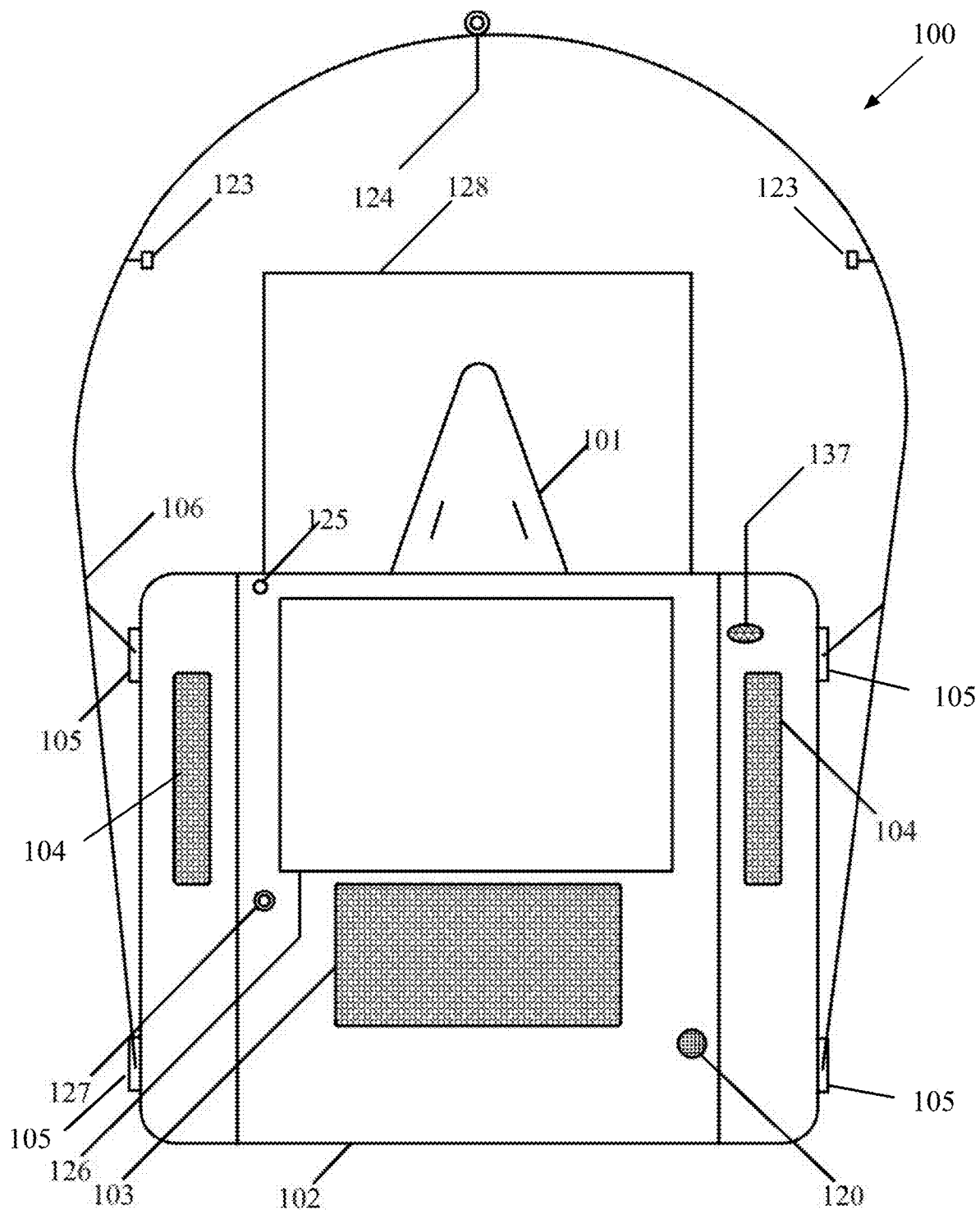
FIG. 28 is a front elevation view.
Figure 29:
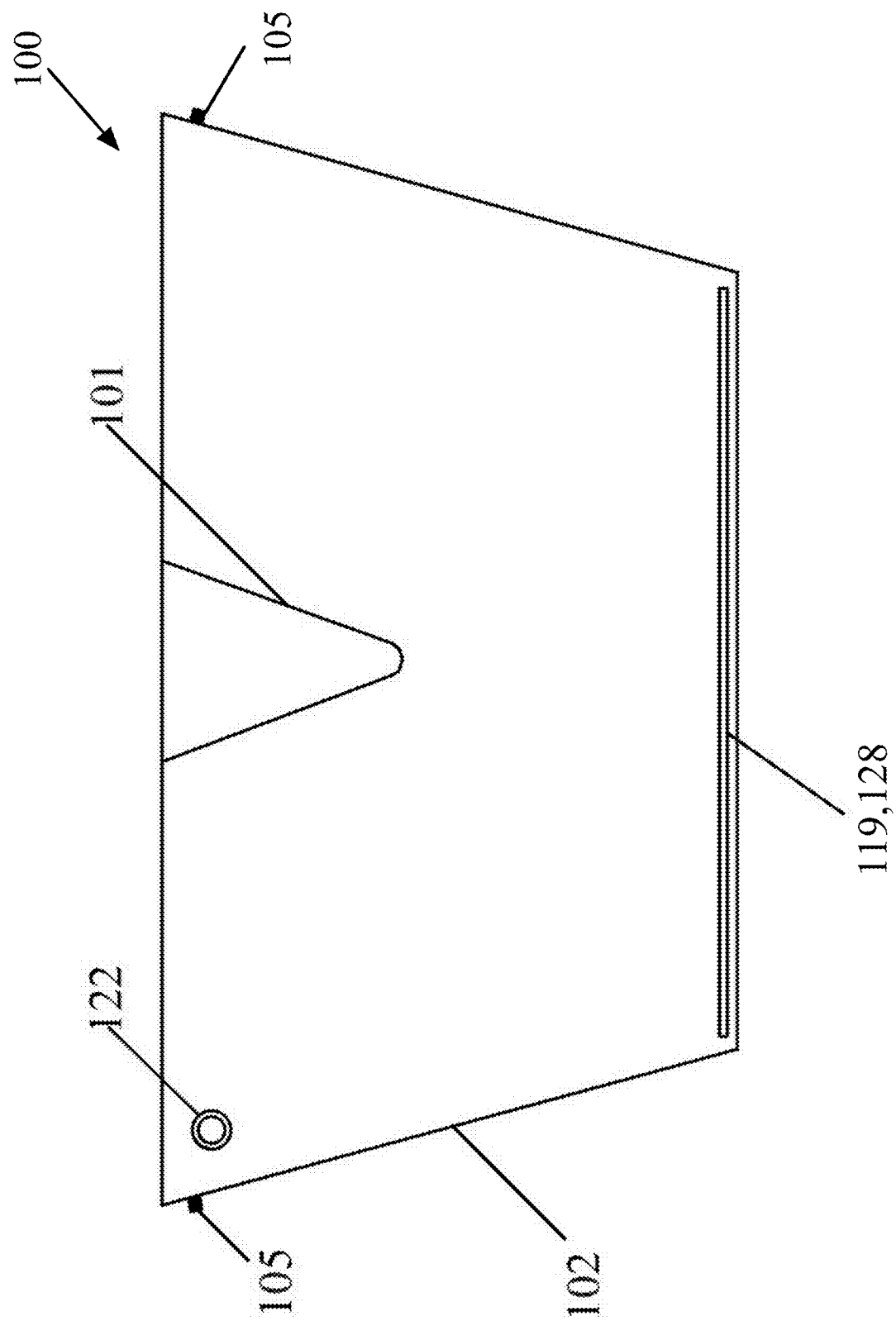
FIG. 29 is a top view, of the reusable purified air breathing device of FIG. 27.
Figure 30:
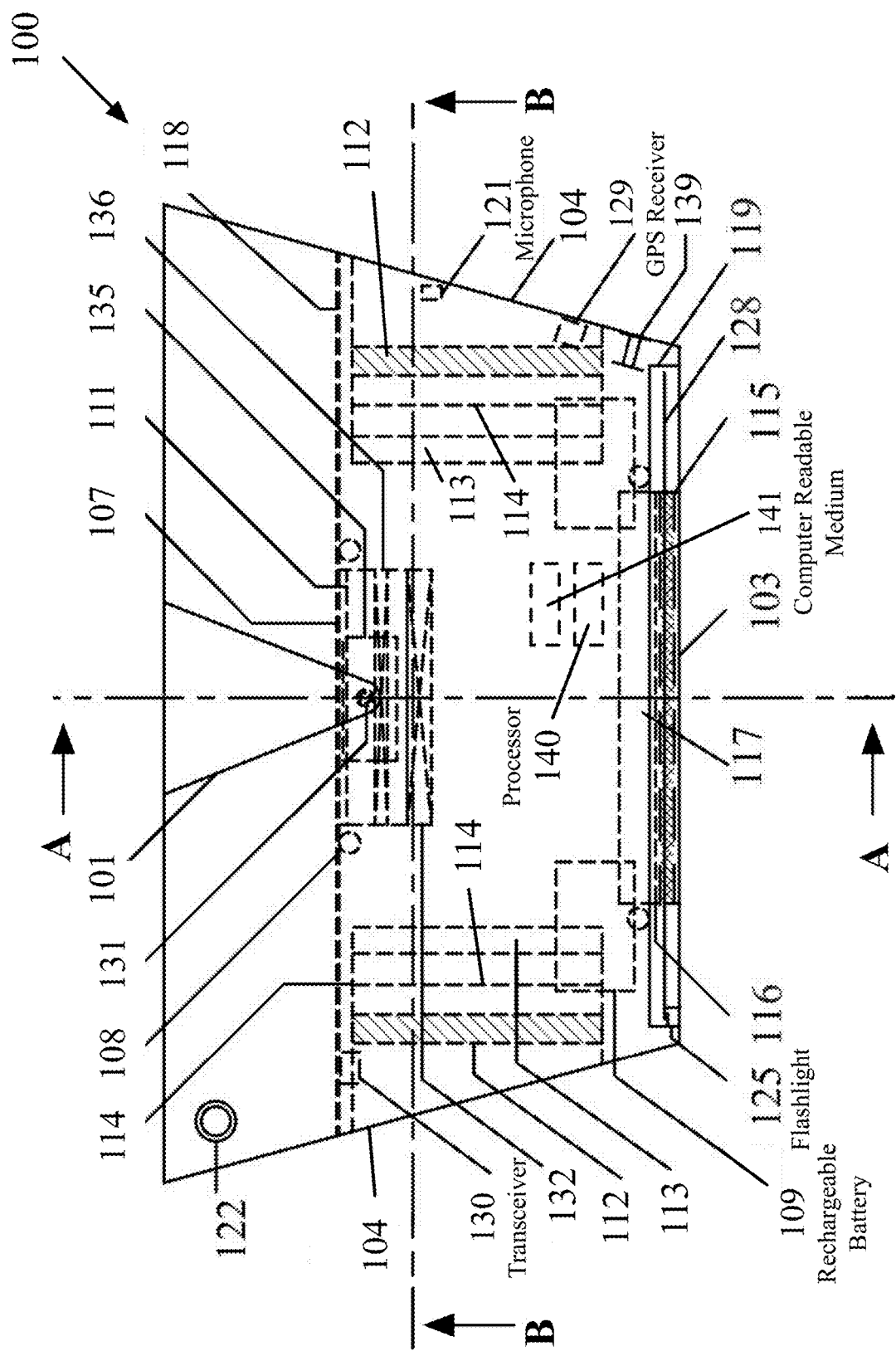
FIG. 30 is a top view of the reusable purified air breathing device of FIG. 27 illustrating further components of the air breathing device, according to various aspects of the present disclosure.

FIG. 27 is a perspective view of a reusable purified air breathing device that provides network connection, one or more cameras, one or more display screens, a GPS receiver, a cellular signal receiver, one or more Wi-Fi and/or Bluetooth receivers, and/or an air heating module, according to various aspects of the present disclosure. FIG. 28 is a front elevation view, and FIG. 29 is a top view, of the reusable purified air breathing device of FIG. 27. FIG. 30 is a top view of the reusable purified air breathing device of FIG. 27 illustrating further components of the air breathing device, according to various aspects of the present disclosure. The side elevation view of FIG. 27 is similar to the side elevation view shown in FIG. 21. FIGS. 28 and 29 only show the components of the air breathing device 100 that are visible from the outside of the air breathing device 100.

With reference to FIGS. 27-30, the air breathing device 100 may include similar components as the air breathing device 100 of FIGS. 20-26. For example, the air breathing device 100 of FIGS. 27-30 may include a nose enclosure 101, a casing 102, one or more breathing air discharge screens 103, one or more breathing air entry screens 104, several harness handles 105, a harness 106, one or more slot openings 107, one or more UV light sources 108, one or more rechargeable batteries 109, a decontamination chamber 110, one or more UVC light isolation screens 111, 114, and 116, one or more air filter cartridges 112, several sets of dampers 113 and 117, one or more discharge air filters 115, one or more isolation elastic membranes 118, an audio speaker 120, a microphone 121, a UV Light on/off switch 122, a flashlight 125, and/or an air pressure differential sensor 139.

The air breathing device 100 of FIGS. 27-30 may include one or more optional components, such as, a heat recovery sponge 132, one or more electric heating coils 136, a condensate drain pan 133, a condensate pipe 134, a removable condensate accumulator tank 135, one or more ear pods or similar audio devices 123, an air temperature sensor 131, a rear camera lens 124, a display screen 126, a camera lens 127, a retractable screen 128, an opening 119 for the retractable screen, a processor 140, computer readable media 141, a cellular signal receiver 130, one or more Wi-Fi and/or Bluetooth receivers (not shown), and/or a GPS receiver 129.

The air breathing device 100, in some embodiments (for example in any embodiments described herein with reference to FIGS. 20-32), may include the processor 140 and the computer readable media 141. The computer readable media 141 may include different types of memory units, such as, read-only-memory, volatile read-and-write memory, and/or non-volatile read-and-write memory. The read-only-memory may store static data and instructions that are needed by the processor 140. The non-volatile read-and-write memory may store instructions and data even when the power to the non-volatile memory is off. Some embodiments may use a small mass-storage device (such as a magnetic or optical disk and its corresponding disk drive) as the non-volatile read-and-write memory.

The volatile read-and-write memory device may be random access memory and may be used as system memory. The system memory may store some of the instructions and data that the processor needs at runtime. In some embodiments, the processes of the present embodiments may be stored in the system memory, the non-volatile memory, and/or the read-only memory. From these various memory units, the processor 140 may retrieve instructions to execute, and data to process, in order to execute and control different electronic components of the air breathing device 100 and to perform the processes of some embodiments.

With reference to FIGS. 27 and 30, the air breathing device 100, in some embodiments, may include a heating mechanism to warm the breathing air. For example, in cold environments, the air breathing device 100 may be equipped with a heating module which may include a heat recovery sponge 132, and/or one or more electric heating coils 136, and an air temperature sensor 131.

The heat recovery sponge 132 may capture the heat through the air exhalation process where the warm and moist breathing air comes out of the wearer's lungs. The heat recovery sponge 132 may use the captured heat to warm up the incoming air before entering the wearer's lungs. Warming up the breathing air may prevent the wearer from catching cold or pneumonia during cold seasons. The heat recovery sponge 132 may be made of a highly conductive material, such as, for example, and without limitations, copper.

The discharged air coming out of people's lung is humid. When the discharged air is exposed to cold surface of the heat recovery sponge 132, the air may form condensation which need to be removed. The embodiments that include the heat recovery sponge 132 may include a condensate drain pan 133 underneath the heat recovery sponge 132 to collect condensate from the heat recovery sponge 132. The bottom of the condensate drain pan 133 may be sloped toward the center of the condensate drain pan 133 in order prevent the condensate from spilling out of the pan 133. The condensation may be routed towards the removable condensate accumulator tank 135 via the connecting condensate pipe 134.

In addition to, or in lieu of, the heating sponge 132, some embodiments, may include the electric heating coil 136 to warm up the inhalation air in cold environments. The source of power for the electric heating coil 136 may be the on-board rechargeable batteries 109 or through an external power source via USB port (not shown) mounted on the casing 102. Power through the USB port may be used, for example, and without limitations, when the wearer is sitting in a chair over an extended period of time. The air temperature sensor 131 may be configured to measure the temperature of the air being inhaled inside the casing 102 downstream of the electric heating coil. The air temperature sensor 131 measurements may be used by the processor 140 to control the temperature of the air being inhaled. For example, the processor 140 may regulate the temperature of the air being inhaled by modulating or turning the electric heating coil 136 on or off.

In the embodiment depicted in FIGS. 27-30, the air breathing device 100 includes one electric heating coil 136, which is located close to the slot openings 107. Other embodiments may include one or more electric heating coils, which may be placed in other locations inside the casing 102. For instance, some embodiments may include two electric heating coils 136 and each electric heating coil 136 may be located at one of the air intake ports 137 downstream of the corresponding air filter 112. For example, and without limitations, each electric heating coil 136 may be located at one of the air intake ports 137 between the air filter 112 and the set of dampers 113.

With reference to FIGS. 27-30, the air breathing device 100 may include a cellular signal receiver 130 and/or one or more Wi-Fi and/or Bluetooth receivers (not shown) to provide connection to one or more networks. The GPS receiver 129 may be configured to receive the air breathing device's location from one or more satellites. The air breathing device 100 may include an assisted GPS (A-GPS) (not shown) to receive assistance data from a networked server to improve the startup performance of the GPS receiver and/or to save power. The network connections may allow the processor 140 to communicate with one or more external electronic devices and function as an IoT device.

The air breathing device 100, in some embodiments, may include a moveable flat or curved display screen 128. The display screen 128 is shown in FIGS. 27 and 28 as being extended to the wearer's eye level. The display screen 128 may be retracted in a corresponding opening 119 when the display screen 128 is not being used. The display screen 128 may enable the wearer to display content through networks, such as, the Internet.

The air breathing device 100, in some embodiments, may include one or more car pods or similar audio devices 123, which may be located on the harness 106. The air breathing device 100, in some embodiments, may include a display screen 126 (e.g., and without limitations, a liquid crystal display (LCD) screen). The air breathing device 100 covers the mouth of wearer, making the communication with other people difficult. The display screen 126 may enhance communication between the wearer and other persons. The display screen 126 may be mounted in front of the air breathing device 100. The wearer may use the display screen 126 for messaging or signaling to other persons. The air breathing device 100, in some embodiments, may include a rear facing camera 124 mounted on the harness 106. The rear view captured by the rear facing camera 124 may be observed through the display screen 128.

Figure 31:
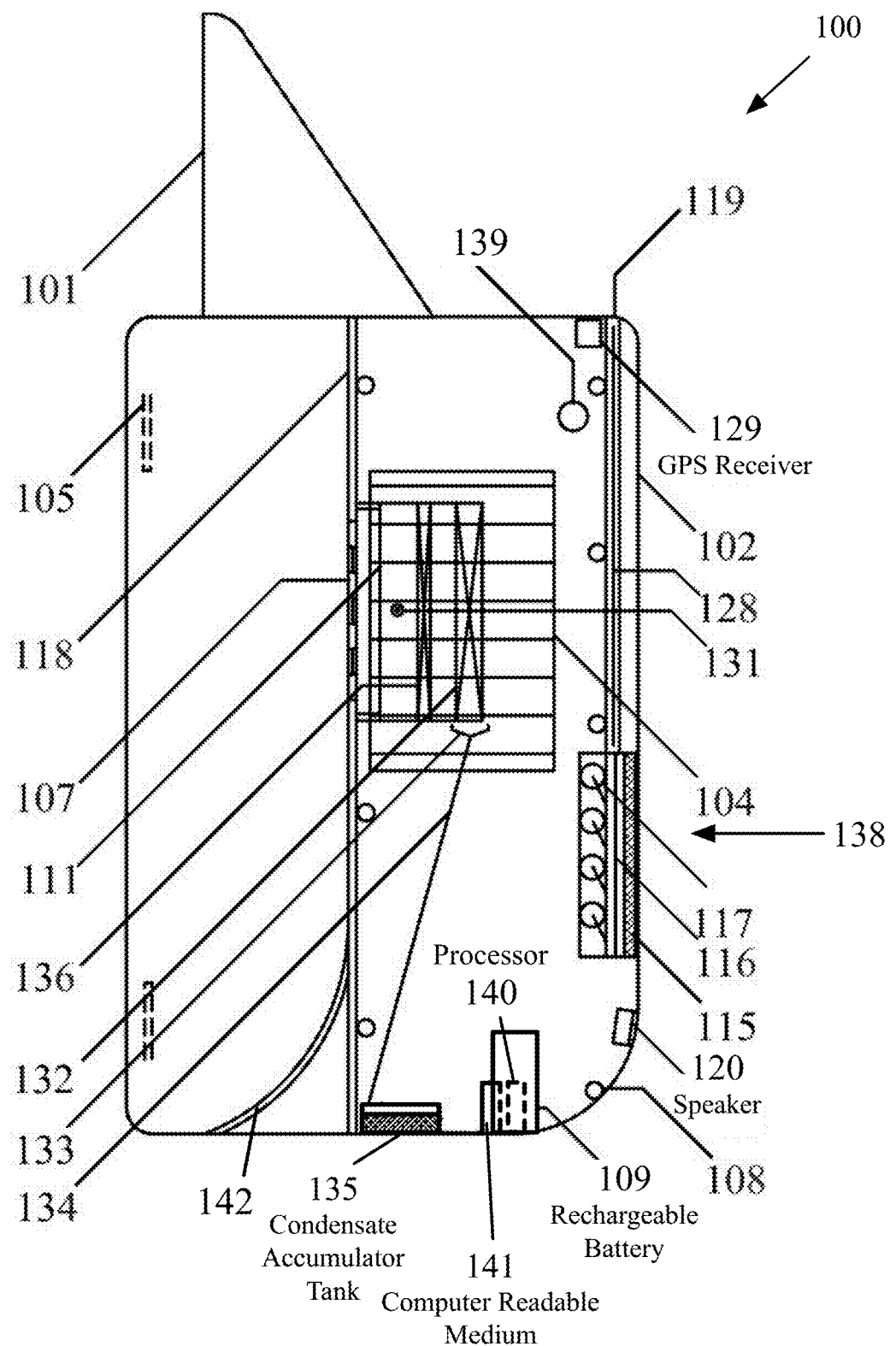
FIG. 31 is a side cross sectional view of the reusable purified breathing air device along the line A-A shown in FIG. 30.
Figure 32:
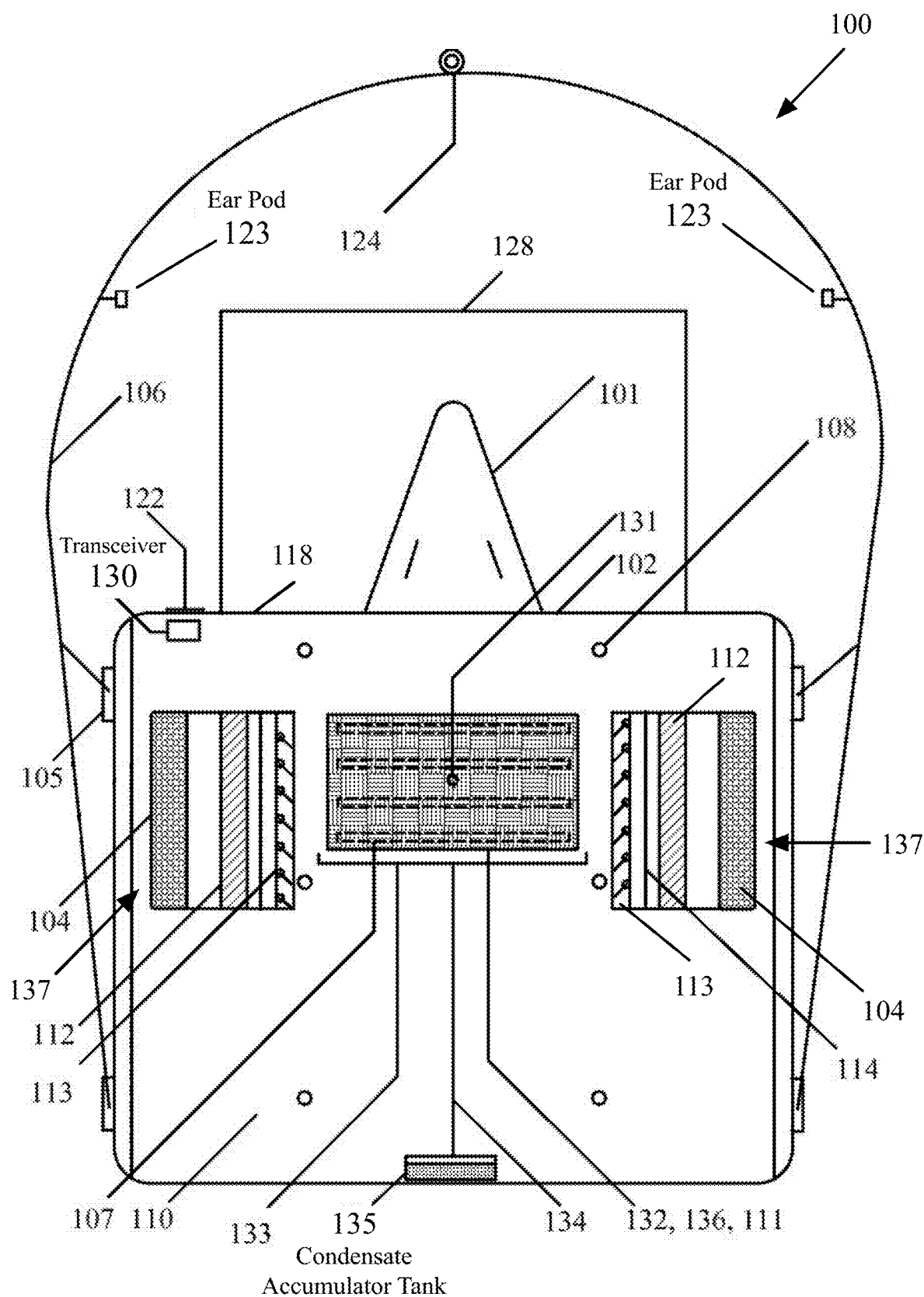
FIG. 32 is a front cross sectional view of the reusable purified air breathing device along the line B-B shown in FIG. 30, according to various aspects of the present disclosure.

FIG. 31 is a side cross sectional view of the reusable purified breathing air device along the line A-A shown in FIG. 30, and FIG. 32 is a front cross sectional view of the reusable purified air breathing device along the line B-B shown in FIG. 30, according to various aspects of the present disclosure.

FIG. 31 shows components similar to the cross sectional view of FIG. 25. In addition, FIG. 31 illustrates the heat recovery sponge 132, the electric heating coil 136, the air temperature sensor 131, the condensate drain pan 133, the condensate pipe 134, the removable condensate accumulator tank 135, the retractable screen 128, the opening 119 for the retractable screen, and the GPS receiver 129.

FIG. 32 shows components similar to the cross sectional view of FIG. 26. In addition, FIG. 32 illustrates the heat recovery sponge 132, the electric heating coil 136, the air temperature sensor 131, the condensate drain pan 133, the condensate pipe 134, the removable condensate accumulator tank 135, the retractable screen 128, the cellular signal receiver 130, the GPS receiver 129, and/or the ear pods 123.

In the embodiments of FIGS. 20-32, the air breathing device 100 is a half face air breathing device that covers the nose, the mouth, and the chin of the wearer. In other embodiments, the air breathing device may be a full face air breathing device. In these embodiments, the air breathing device may cover the head and the neck of the wearer and may form a hood, or a helmet, around the wearer's head. The full face air breathing device of some embodiments may not include the retractable screen 128, the opening 119 for the retractable screen, the harness 106 and/or the harness handles 105. In some embodiments, the ear plugs 123 may be installed inside the hood of the full face air breathing device. In some embodiments, the rear view camera lens 124 may be installed on the outside of the hood of the full face air breathing device.

As discussed above, the air breathing device 100 of the present embodiments may include one or more air intake ports 137 and one or more air discharge ports 138, and the air intake port(s) 137 and the air discharge port(s) may be positioned on different locations on the casing 102. For example, the embodiment shown in FIGS. 1-4D and FIGS. 14-19 includes two air intake ports 137 and two air discharge ports 138. An example of the air breathing device 100 of the present embodiments of the present embodiments with one air intake port 137 and one air discharge port 138 is shown in FIGS. 33-35.

Figure 33:
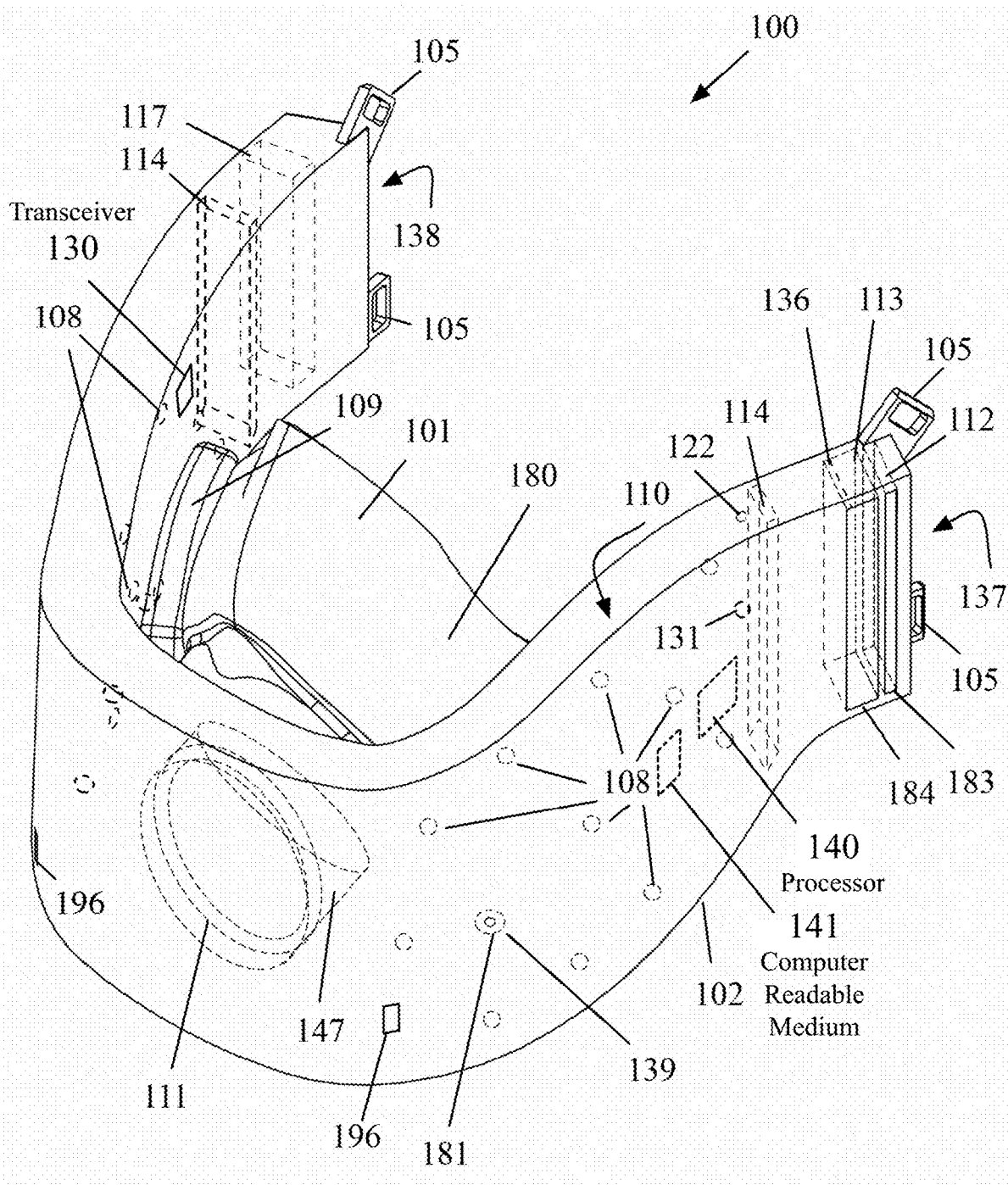
FIG. 33 is a perspective view of a reusable purified air breathing device 100 that includes only one air intake port and only one air discharge port, according to various aspects of the present disclosure.

FIG. 33 is a perspective view of a reusable purified air breathing device 100 that includes only one air intake port and only one air discharge port, according to various aspects of the present disclosure. FIG. 34 is a back and side perspective view of the air breathing device 100 of FIG. 33, showing the air intake port according to various aspects of the present disclosure. FIG. 35 is a back and side perspective view of the air breathing device 100 of FIG. 33, showing the air discharge port according to various aspects of the present disclosure. It should be noted that, although the air intake port is shown near the wearer's left ear, and air discharge port is shown near the wearer's right ear, the location of the air intake port and the air discharge port may be different in other embodiments.

Figure 34:
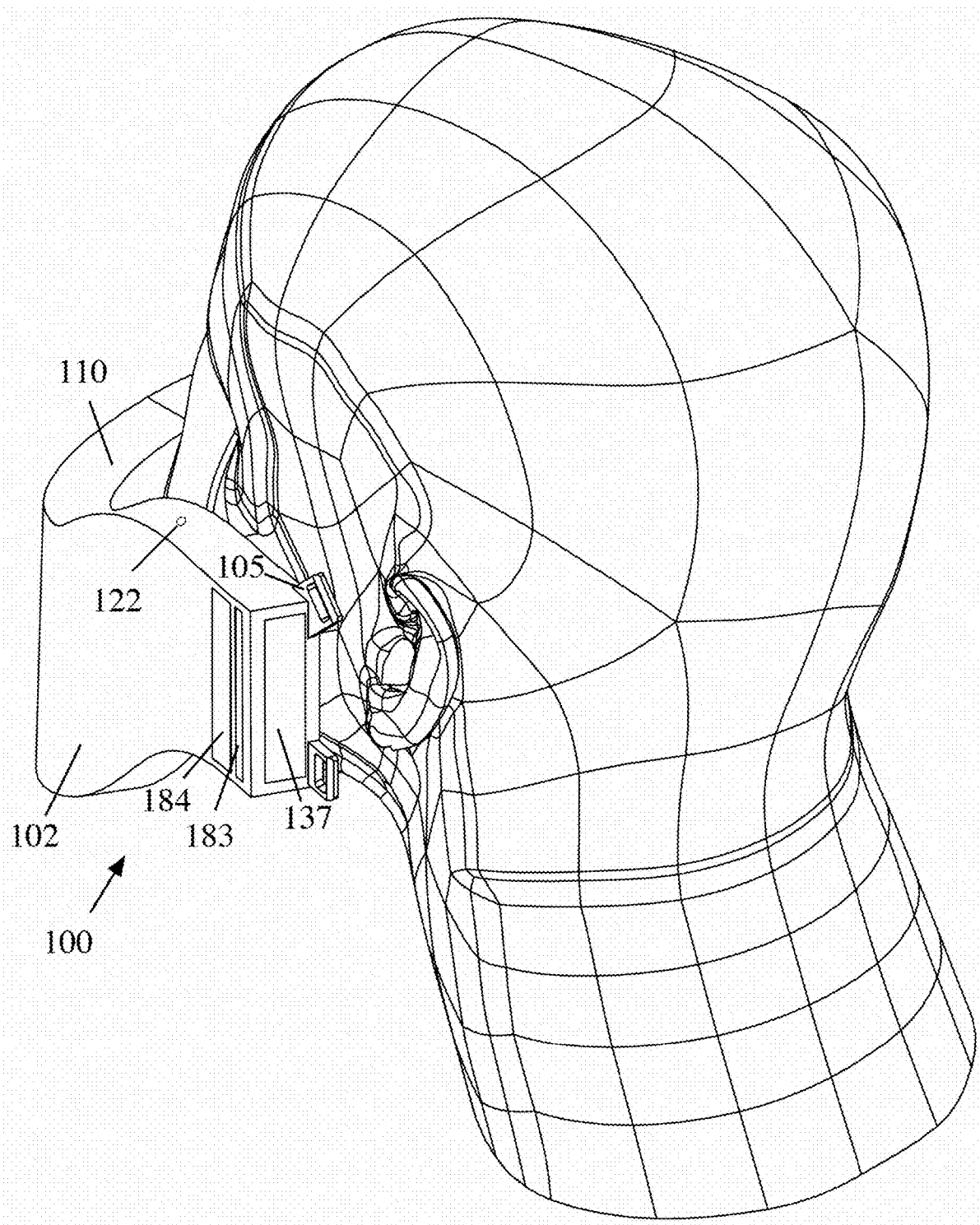
FIG. 34 is a back and side perspective view of the air breathing device of FIG. 33, showing the air intake port according to various aspects of the present disclosure.
Figure 35:
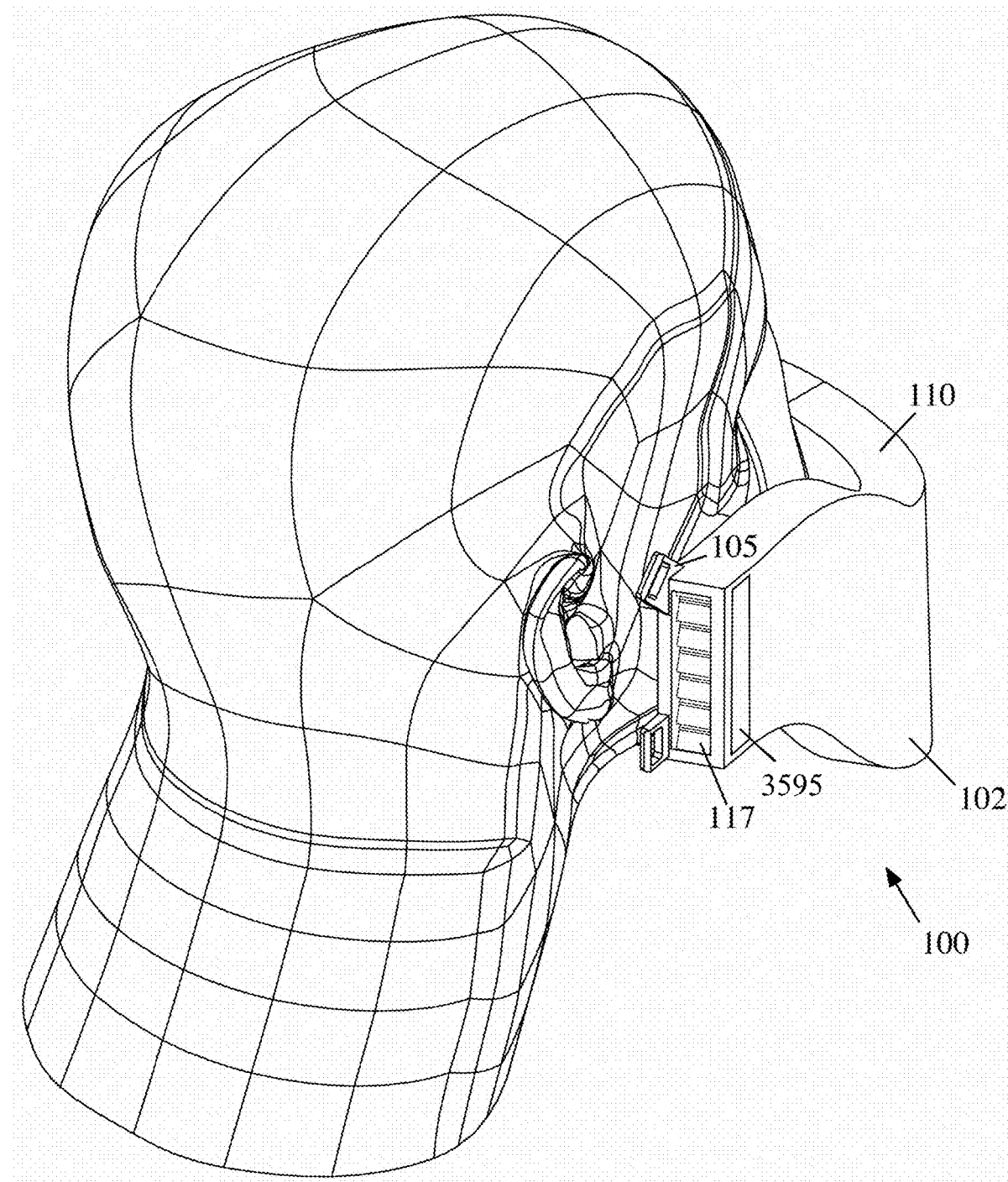
FIG. 35 is a back and side perspective view of the air breathing device of FIG. 33, showing the air discharge port according to various aspects of the present disclosure.

FIGS. 34-35 only show the components of the air breathing device 100 that are visible from the outside of the air breathing device 100. The air breathing device 100 of FIGS. 33-35 may include similar components as the air breathing device 100 of FIGS. 1-4D and 14-19, except that the air breathing device 100 of FIGS. 33-35 includes only one air intake port 137 and only one air discharge port 138. For example, the air breathing device 100 of FIGS. 33-35 may include a nose enclosure 101, a casing 102, several harness handles 105, one or more harnesses (or straps) 106, one or more UV light sources 108, a UV light status indicator 196, one or more rechargeable batteries 109, a decontamination chamber 110, one or more UVC light isolation screens 111 and 114, one or more air filter cartridges 112, one or more electric heating coils 136, one or more air temperature sensors 131, a UV Light on/off switch 122, an air pressure differential sensor 139, a USB port 410, one or more ear pods or similar audio devices 123, a rear camera lens 124, a fixed display screen 126, a forward camera lens 127, a retractable display screen 128, an opening 119 for the retractable screen, an audio speaker 120, a microphone 121, a flashlight 125, a processor 140, computer readable media 141, one or more wireless transceivers 130, a GPS receiver 129, and/or a camera lens 197 directed to the wearer's mouth. Some of the components of FIGS. 1-4D and FIGS. 14-19 may not be shown in FIGS. 33-35 for clarity. The embodiments that include a retractable screen may include an opening (e.g., similar to the opening 119 of FIGS. 14 and 36) on the casing 102 for the retractable screen.

With reference to FIGS. 33-35, when the wearer inhales air, the outside air enters through the air intake port 137, travels through the decontamination chamber 110 and enters the air tube 147 to reach the wearer's mouth. During the inhale, the discharge damper 117 near the air discharge port 138 is close, and the intake damper 113 near the air intake port 137 is open, allowing air to enter the air breathing device 100 only from the air intake port 137.

When the wearer exhales air, the exhaled air enters the air tube 147, then transfers to and travels through the decontamination chamber 110, and exits the air breathing device 100 via the air discharge port 138. During the exhale, air intake damper 113 near the air intake port 137 is close, and the air discharge damper 117 near the air discharge port 138 is open, allowing air to exit the air breathing device 100 only from the air discharge port 138. The air breathing device 100 of FIGS. 33-35 may include a motor that may receive signals from the processor 140 to open and close the air intake damper 113 (e.g., as described above with reference to FIGS. 5A-5C, 6, 7A-7D, and 8A-8C). The air breathing device 100 of FIGS. 33-35 may include a motor that may receive signals from the processor 140 to open and close the air discharge damper 117 (e.g., as described above with reference to FIGS. 5A-5C, 6, 7A-7D, and 8A-8C). As described above, the quantity and power of UVC LED lights 108 used in the decontamination chamber 110, in both intake and discharge sides, may be increased to achieve the desired inactivation rate of microorganisms.

With reference to FIGS. 33-34, the air breathing device 100 may include a replaceable air filter cartridge 112 at the air intake port 137, which may be similar to the air filter cartridge 112 described above with reference to FIGS. 1-4E. The air filter cartridge 112 may be accessed (e.g., for replacement) through the air filter cartridge cover 183. The optional electric heating coil 136, in some embodiments, may be removed, for example, to do maintenance, or to reduce the weight and air pressure drop during warm seasons. The intake dampers 113 may be accessed (e.g., for service or replacement) by removing the access cover 184 that provides access to both the air intake dampers 113 and the optional electric heating coil 136.

With reference to FIG. 35, the discharge dampers 117, in some embodiments, may be accessed (e.g., for service or replacement) through the access cover 3395. In other embodiments, the discharge dampers 117 may be accessed through the discharge port 138, as described above with reference to FIGS. 1-4D. It should be noted that the air breathing device 100 of FIGS. 33-35 may also include a replaceable air filter cartridge 112 at the air discharge port 138 to filter the air breathed by the person wearing the air breathing device 100 to prevent air breathed by the person from contaminating the air outside of the air breathing device.

Figure 36:
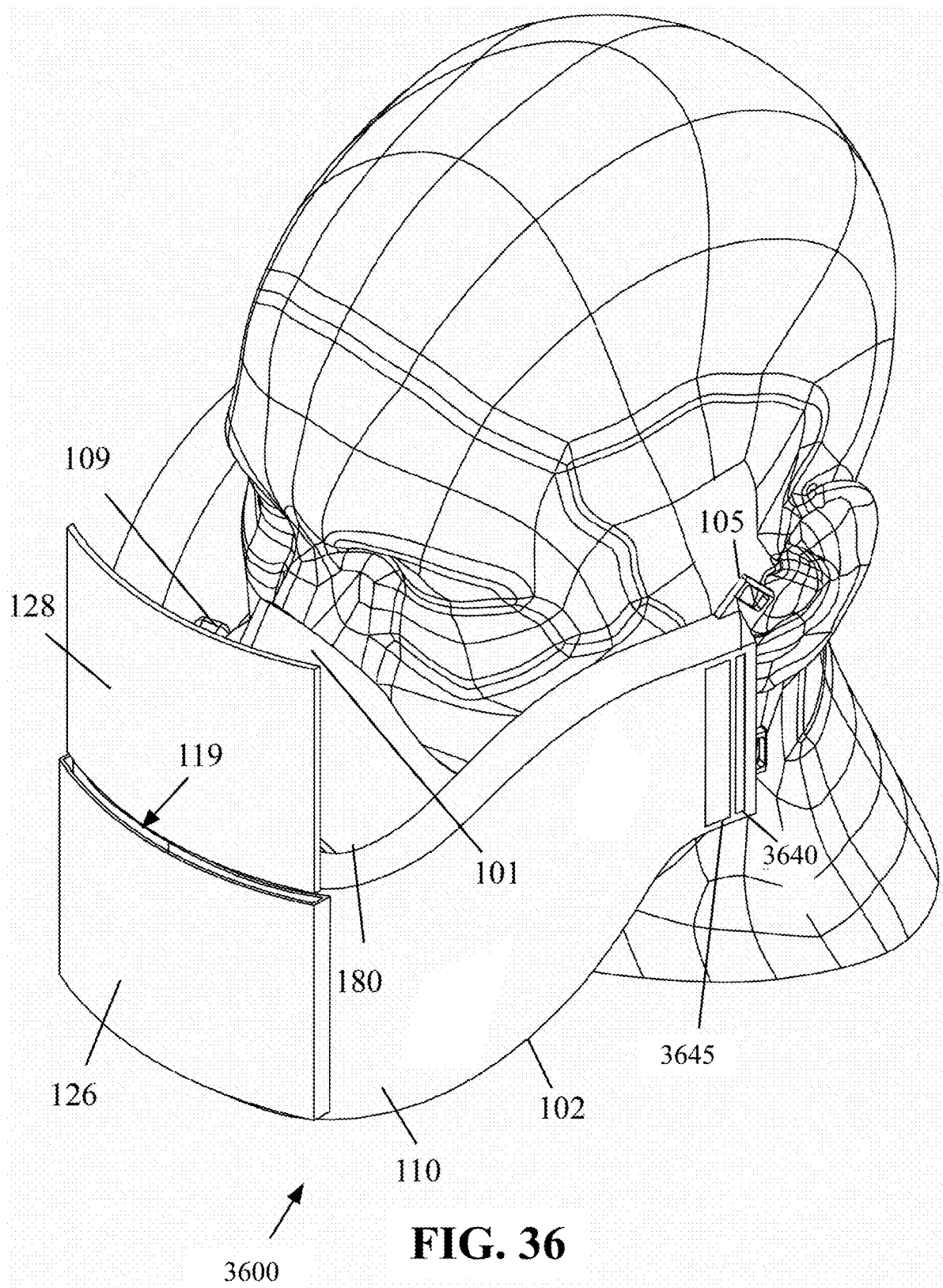
FIG. 36 is a front and side perspective view of an air breathing device with a display screen, according to various aspects of the present disclosure.
Figure 37:
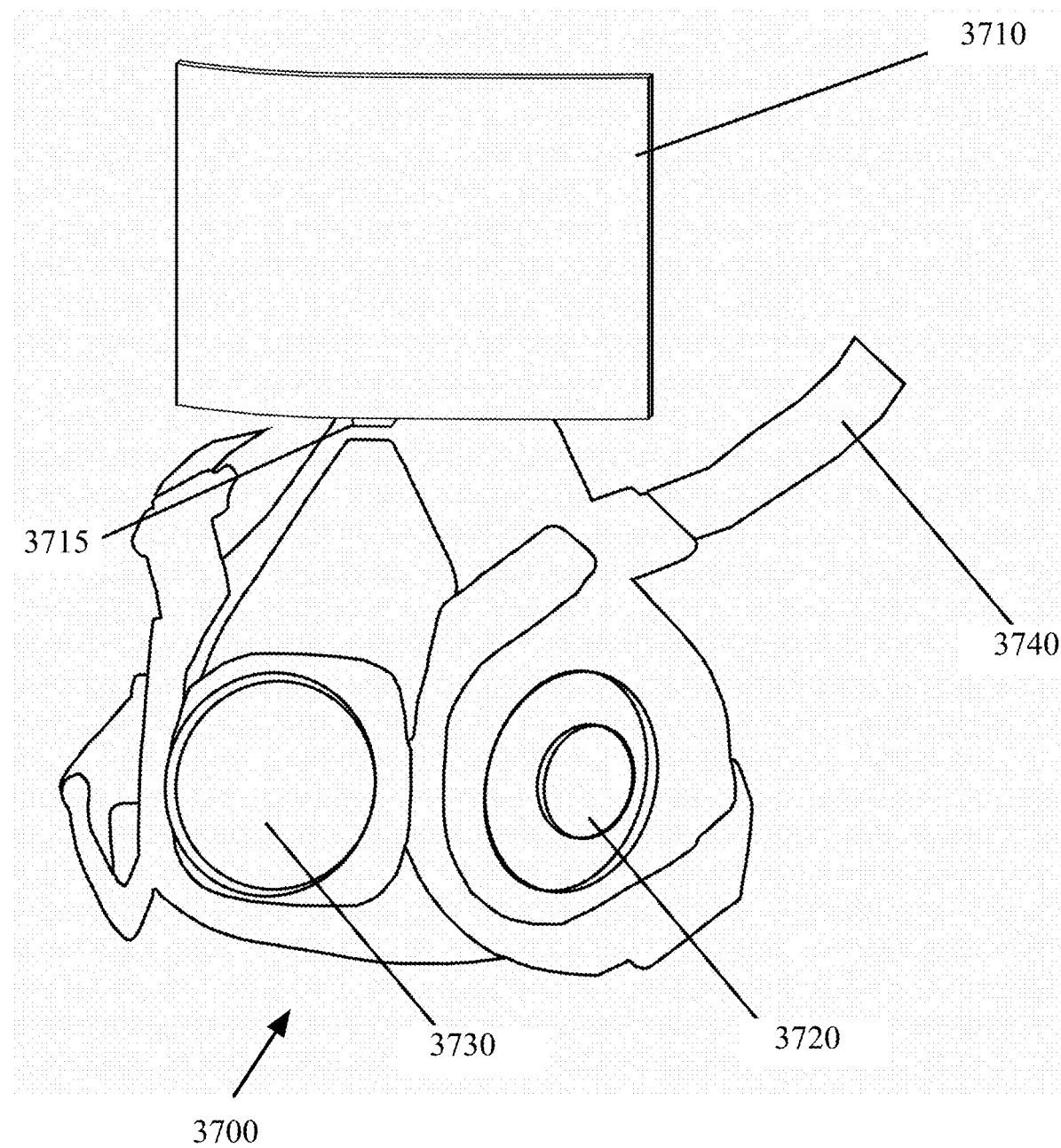
FIG. 37 is a front elevation view of an air breathing device with a display screen, according to various aspects of the present disclosure.

The display screens, for example, the display screens 126, 128, and 1410 of the present embodiments may be used on any other type of air breathing devices and masks (e.g., air breathing devices and masks that do not include dampers, heaters, UV lights, etc., that are unique to the air breathing devices of the present embodiments). FIG. 36 is a front and side perspective view of an air breathing device with a display screen, according to various aspects of the present disclosure. FIG. 37 is a front elevation view of an air breathing device with a display screen, according to various aspects of the present disclosure.

FIG. 36 shows an air breathing device 3600 that includes a single port 3640 for air intake and air discharge, a fixed display screen 126, a retractable display screen 128, and an opening 119 for the retractable screen. In other embodiments, the air breathing device 3600 only include the fixed display screen 126, may only include the retractable display screen 128, may only include a fixed display screen 126 and a detachable screen 1410 (e.g., similar to the air breathing device 100 of FIG. 17D), or may only include a detachable screen 1410. The fixed display screen 126, the retractable display screen 128, and the detachable screen 1410 may be similar to the corresponding components of FIGS. 17A-17D. The power of the display screens 126, 128, and 1410 may be supplied by one or more onboard batteries 109, which may be similar to the one or more onboard batteries 109 of the breathing device 100 of FIGS. 17A-17D.

The single port 3640 for air intake and air discharge may include a valve (not shown) that may be used to open the port 3640 during air intake or discharge. The valve may be accessed (e.g., for repair or replacement) through the cover 3645.

FIG. 37 shows another example of an air breathing device 3700 that includes a display screen 3710. The display screen 3710, in the depicted embodiment, may be a fixed or a detachable screen. The display screen 3710 may be connected to the air breathing device 3700 with one or more connectors 3715. In other embodiments, the display screen 3710 may be retractable, for example, as shown in FIG. 36.

The air breathing device 3700 may include an air intake opening 3720, which may be used to connect an air filter to the air breathing device 3700. The air breathing device 3700 may include an air discharge opening 3730 to discharge air from the air breathing device. The air breathing device 3700 may include one or more harnesses (or straps) 3740 that may be configured to secure the air breathing device 3700 behind the head and neck of the wearer.

Figure 38:
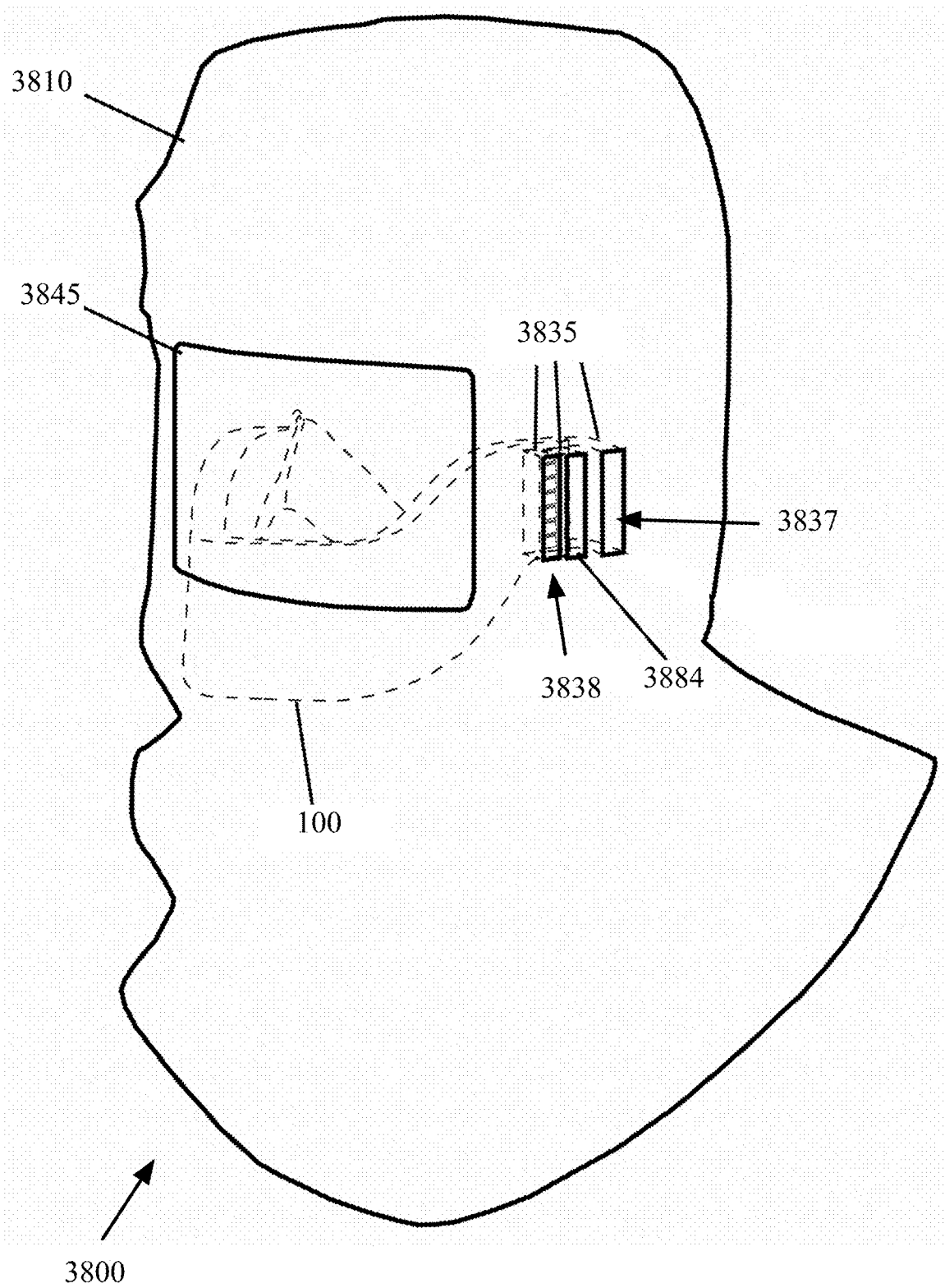
FIG. 38 is a front and side perspective view of an air breathing device with a flexible full head cover, according to various aspects of the present disclosure.
Figure 39:
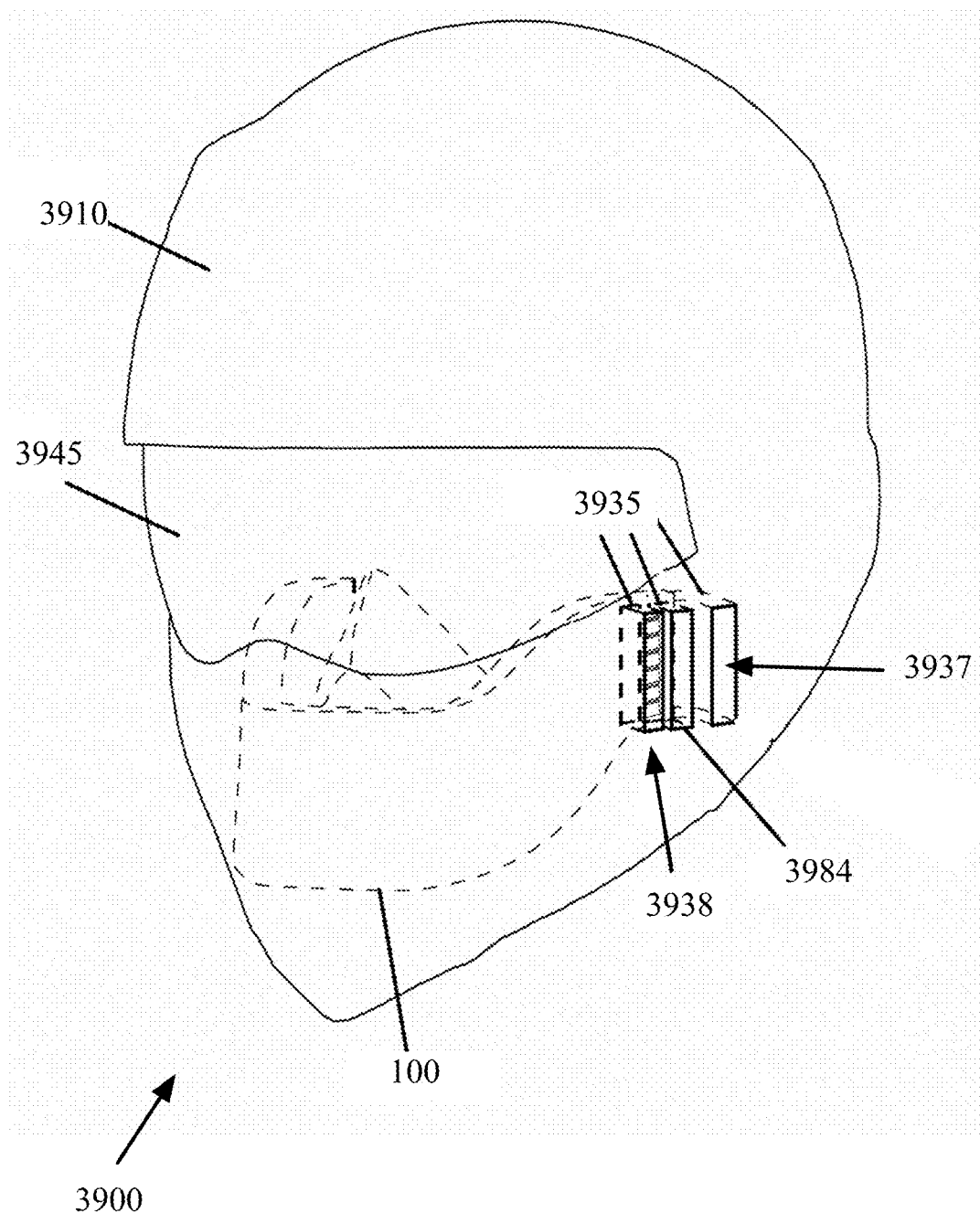
FIG. 39 is a front and side perspective view of an air breathing device with a rigid full head cover, according to various aspects of the present disclosure.
Figure 40:
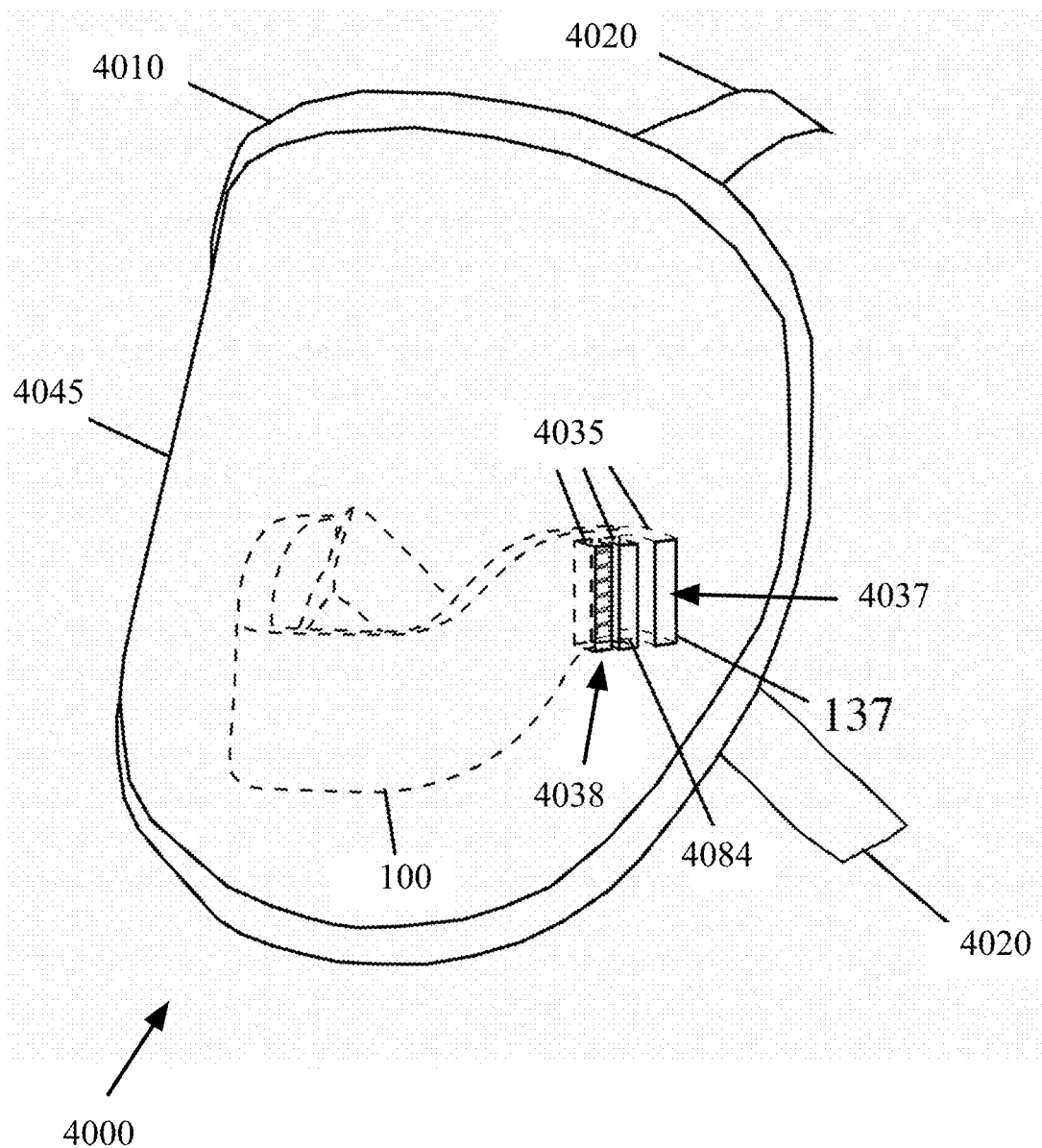
FIG. 40 is a front and side perspective view of an air breathing device with a full face cover, according to various aspects of the present disclosure.

Some embodiments may provide an air breathing device that includes a full head cover that may be used to protect the head, neck, and face skin of the wearer against dust, sparks, and hazardous material. Some embodiments may provide an air breathing device that includes a full face cover that may be used to protect the face of the wearer against dust and sparks. FIG. 38 is a front and side perspective view of an air breathing device 3800 with a flexible full head cover, according to various aspects of the present disclosure. FIG. 39 is a front and side perspective view of an air breathing device 3900 with a rigid full head cover, according to various aspects of the present disclosure. FIG. 40 is a front and side perspective view of an air breathing device 4000 with a full face cover, according to various aspects of the present disclosure.

With reference to FIG. 38, the full head air breathing device 3800 may include a full head cover 3810 (e.g., a helmet) that may be configured to protect the head, neck, and face of the wearer against dust, sparks, and hazardous material. The full head cover 3810 may be made of flexible material, for example, similar to a hazmat (hazardous material) suit material, such as Polytetrafluoroethylene (PTFE), synthetic flashspun high-density polyethylene fibers, etc. The full head cover 3810 may also include a pressurization fan (not shown) to slightly increase the air pressure inside the full head cover 3810, eliminating infiltration of contaminated outside air to the full head cover 3810.

The full head air breathing device 3800 may include an air breathing device 100, which may be similar to the air breathing device 100 of FIGS. 1-4D and 14-19. Similar to the air breathing device 100 of FIGS. 1-4D and 14-19, the air breathing device 100 of FIG. 3800 may include several harness handles 105 (not shown) and one or more of harnesses 106 (not shown) that may be configured to secure the air breathing device 100 behind the head and neck of the wearer. The full head air breathing device 3800 may include one or more air intake ports 3837 (only one is shown in the perspective view of FIG. 38) and one or more air discharge ports 3838 (only one is shown in the perspective view of FIG. 38).

The full head air breathing device 3800 may include one or more air ducts 3835 (only one is shown in the perspective view of FIG. 38). Each air duct 3835 may connect an air intake port 3837 of the full head air breathing device 3800 to a corresponding air intake port 137 (e.g., the air input port 137 of FIG. 1) of the air breathing device 100. Each air duct 3835 may connect an air discharge port 3838 of the full head air breathing device 3800 to a corresponding air discharge port 138 (e.g., the air input port 138 of FIG. 1) of the air breathing device 100.

The full head air breathing device 3800 may include a transparent view screen 3845 that may be covered with a transparent material, such as glass. The full head air breathing device 3800 may include an access cover 3884 that may provide access to the access cover 184 (e.g., the access cover 184 of FIG. 1) of the air breathing device 100.

With reference to FIG. 39, the full head air breathing device 3900 may include a full head cover 3910 (e.g., a helmet) that may be configured to protect the head, neck, and face of the wearer against dust, sparks, impacts, and hazardous material. The full head cover 3910 may be made of hard (or rigid) material, for example, heavy Polyvinyl chloride (PVC), rubber, etc. The full head cover 3910 may also include a pressurization fan (not shown) to slightly increase the air pressure inside the full head cover 3910, eliminating infiltration of contaminated outside air to the full head cover 3910.

The full head air breathing device 3900 may include an air breathing device 100, which may be similar to the air breathing device 100 of FIGS. 1-4D and 14-19. Similar to the air breathing device 100 of FIGS. 1-4D and 14-19, the air breathing device 100 of FIG. 3900 may include several harness handles 105 (not shown) and one or more of harnesses 106 (not shown) that may be configured to secure the air breathing device 100 behind the head and neck of the wearer. The full head air breathing device 3900 may include one or more air intake ports 3937 (only one is shown in the perspective view of FIG. 39) and one or more air discharge ports 3938 (only one is shown in the perspective view of FIG. 39).

The full head air breathing device 3900 may include one or more air ducts 3895 (only one is shown in the perspective view of FIG. 39). Each air duct 3935 may connect an air intake port 3937 of the full head air breathing device 3900 to a corresponding air intake port 137 (e.g., the air input port 137 of FIG. 1) of the air breathing device 100. Each air duct 3935 may connect an air discharge port 3938 of the full head air breathing device 3900 to a corresponding air discharge port 138 (e.g., the air input port 138 of FIG. 1) of the air breathing device 100.

The full head air breathing device 3900 may include a transparent view screen 3945 that may be covered with a transparent material, such as glass. The full head air breathing device 3900 may include an access cover 3984 that may provide access to the access cover 184 (e.g., the access cover 184 of FIG. 1) of the air breathing device 100.

With reference to FIG. 40, the full face air breathing device 4000 may include a full face cover 3910 that may be configured to protect the face of the wearer against dust and sparks. The full head cover 4010 may include a transparent view screen 4045 that may be covered with a transparent material, such as glass. The full head cover 4010 may include one or more harnesses (or straps) 4020 that may be configured to secure the full face air breathing device 4000 behind the head and neck of the wearer.

The full face air breathing device 4000 may include an air breathing device 100, which may be similar to the air breathing device 100 of FIGS. 1-4D and 14-19. Similar to the air breathing device 100 of FIGS. 1-4D and 14-19, the air breathing device 100 of FIG. 4000 may include several harness handles 105 (not shown) and one or more of harnesses 106 (not shown) that may be configured to secure the air breathing device 100 behind the head and neck of the wearer. The full face air breathing device 4000 may include one or more air intake ports 4037 (only one is shown in the perspective view of FIG. 40) and one or more air discharge ports 4039 (only one is shown in the perspective view of FIG. 40).

The full face air breathing device 4000 may include one or more air ducts 4095 (only one is shown in the perspective view of FIG. 40). Each air duct 4035 may connect an air intake port 4037 of the full face air breathing device 4000 to a corresponding air intake port 137 (e.g., the air input port 137 of FIG. 1) of the air breathing device 100. Each air duct 4035 may connect an air discharge port 3938 of the full face air breathing device 4000 to a corresponding air discharge port 138 (e.g., the air input port 138 of FIG. 1) of the air breathing device 100. The face head air breathing device 4000 may include an access cover 4084 that may provide access to the access cover 184 (e.g., the access cover 184 of FIG. 1) of the air breathing device 100.

In a first aspect, an air breathing device is provided. The air breathing device comprises a casing. The air breathing device comprises an air passage cavity encompassed by the casing. The air breathing device comprises a set of one or more air intake ports, each air intake port connecting the air passage cavity to an outside of the casing through an air intake damper, each air intake damper comprising a set of one or more blades and a corresponding set of one or more hinges, each air intake damper blade configured to rotate in a first direction around the corresponding hinge in response to an air pressure inside of the air passage cavity being less than an air pressure outside of the casing to open the air intake damper, and each air intake damper blade configured to rotate in a second direction around the corresponding hinge in response to an air pressure inside of the air passage cavity being more than an air pressure outside of the casing to close the air intake damper. The air breathing device comprises a set of one or more air discharge ports, each air discharge port connecting the air passage cavity to the outside of the casing through an air discharge damper, each air discharge damper comprising a set of one or more blades and a corresponding set of one or more hinges, each air discharge damper blade configured to rotate in a third direction around the corresponding hinge in response to an air pressure inside of the air passage cavity being more than an air pressure outside of the casing to open the air discharge damper, and each air discharge damper blade configured to rotate in a fourth direction around the corresponding hinge in response to an air pressure inside of the air passage cavity being less than an air pressure outside of the casing to close the air discharge damper. The air breathing device comprises an air tube connecting the air passage cavity to a mouth of a person wearing the air breathing device. The air breathing device comprises a set of one or more ultraviolet (UV) light sources inside the air passage cavity. The air breathing device comprises a first set of one or more UV light screens located inside the air tube, the first set of one or more UV light screens separating the air passage cavity from the person's mouth. The air breathing device comprises a second set of one or more of UV light screens, each UV light screen in the second set of UV light screens separating the air passage cavity from one air intake port and one air discharge port.

In an embodiment of the first aspect, the UV light sources are configured to generate UV rays with a wavelength ranging between 200 nanometers to 280 nanometers.

In another embodiment of the first aspect, at least a portion of an interior surface of the air passage cavity comprises a material that is reflective to UV rays.

An embodiment of the first aspect further comprises a switch to turn the set of UV light sources on or off.

Another embodiment of the first aspect further comprises a replaceable air filter located inside the casing at each air intake port.

Another embodiment of the first aspect further comprises a perforated screen at each air intake port; and a perforated screen at each air discharge port.

Another embodiment of the first aspect further comprises a retractable display screen; a set of one or more wireless transceivers; and a processor configured to: receive content, through the set of wireless transceivers, from one or more electronic devices external to the air breathing device; and display the content on the retractable display screen.

In another embodiment of the first aspect, the retractable display screen is configured to display content to the person wearing the air breathing device.

In another embodiment of the first aspect, the retractable display screen is one of a HUD, a LCOS, and a plurality of lenses configured to point images into eyes of the person wearing the air breathing device.

Another embodiment of the first aspect further comprises a set of one or more batteries configured to provide power to the processor, the set of UV light sources, the retractable display screen, and the set of wireless transceivers.

Another embodiment of the first aspect further comprises a USB port mounted on the casing, the USB port configured to connect to an external power source and provide power to the processor, the retractable screen, the set of UV light sources, and the set of wireless transceivers.

In another embodiment of the first aspect, the air breathing device comprises a fixed display screen located on the casing and positioned to be viewable by persons facing the person wearing the air breathing device. The air breathing device comprises a processor configured to receive media content and display the media content on the fixed display screen.

Another embodiment of the first aspect further comprises a camera lens directed to the mouth of the person wearing the air breathing device. The camera lens is configured to capture media content comprising one of a plurality of images and a set of one or more videos. The processor is configured to display the captured content on the fixed display screen.

Another embodiment of the first aspect further comprises a microphone configured to capture sounds spoken by the wearer of the air breathing device. The processor is configured to convert the captured sounds into simulated lip movements and display the simulated lip movements on the fixed display screen.

Another embodiment of the first aspect further comprises a flashlight and a switch to turn the flashlight on or off.

Another embodiment of the first aspect further comprises a microphone configured to capture sounds spoken by the wearer of the air breathing device and a set of one or more speakers configured to play the sounds captured by the microphone.

In another embodiment of the first aspect, the air breathing device comprises a set of one or more heating coils located between the air intake dampers and the air passage cavity. The air breathing device comprises a set of one or more temperature sensors configured to measure the air temperature inside the casing. The air breathing device comprises a set of one or more transceivers. The air breathing device comprises a processor configured to: receive temperature measurements from the set of temperature sensors; receive first and second temperature thresholds from an external electronic device communicatively coupled to the processor through one of the transceivers in the set of transceivers, where the second threshold is larger than the first threshold; turn on power to the set of heating coils when the temperature measurements are below the first threshold; and turn off the power to the heating coils when the temperature measurements are above the second threshold.

Another embodiment of the first aspect further comprises a USB port mounted on the casing, the USB port configured to connect to an external power source and provide power to the set of heating coils, the set of transceivers, the processor, and the set of UV light sources.

Another embodiment of the first aspect further comprises a processor; a plurality of motors, each motor corresponding to an air intake damper or an air discharge damper, each motor configured to receive one or more signals and in response to receiving the signals open or close the corresponding damper; and an air pressure differential sensor configured to measure a difference between the air pressure inside of the air passage cavity and the air pressure outside of the casing; wherein the processor is configured to: receive the air pressure differential readings from the air pressure differential sensor; in response to determining that the air pressure inside of the air passage cavity exceeds the air pressure outside of the casing by a first threshold send one or more signals to the motors corresponding to the air intake dampers to close the air intake dampers, and send one or more signals to the motors corresponding to the air discharge dampers to open the air discharge dampers; and in response to determining that the air pressure outside of the casing exceeds the air pressure inside of the air passage cavity by a second threshold send one or more signals to the motors corresponding to the air intake dampers to open the air intake dampers, and send one or more signals to the motors corresponding to the air discharge dampers to close the air discharge dampers.

In a second aspect, an air breathing device is provided. The air breathing device comprises a casing. The air breathing device comprises an air passage cavity encompassed by the casing. The air breathing device comprises a set of one or more air intake ports, each air intake port connecting the air passage cavity to an outside of the casing through an air intake damper, each air intake damper comprising a set of one or more blades and a corresponding set of one or more hinges, each air intake damper blade configured to rotate in a first direction around the corresponding hinge in response to an air pressure inside of the air passage cavity being less than an air pressure outside of the casing to open the air intake damper, and each air intake damper blade configured to rotate in a second direction around the corresponding hinge in response to an air pressure inside of the air passage cavity being more than an air pressure outside of the casing to close the air intake damper. The air breathing device comprises a set of one or more air discharge ports, each air discharge port connecting the air passage cavity to the outside of the casing through an air discharge damper, each air discharge damper comprising a set of one or more blades and a corresponding set of one or more hinges, each air discharge damper blade configured to rotate in a third direction around the corresponding hinge in response to an air pressure inside of the air passage cavity being more than an air pressure outside of the casing to open the air discharge damper, and each air discharge damper blade configured to rotate in a fourth direction around the corresponding hinge in response to an air pressure inside of the air passage cavity being less than an air pressure outside of the casing to close the air discharge damper. The air breathing device comprises an air tube connecting the air passage cavity to a mouth of a person wearing the air breathing device.

An embodiment of the second aspect further comprises a processor; a plurality of motors, each motor corresponding to an air intake damper or an air discharge damper, each motor configured to receive one or more signals and in response to receiving the signals open or close the corresponding damper; and an air pressure differential sensor configured to measure a difference between the air pressure inside of the air passage cavity and the air pressure outside of the casing; wherein the processor is configured to: receive the air pressure differential readings from the air pressure differential sensor; in response to determining that the air pressure inside of the air passage cavity exceeds the air pressure outside of the casing by a first threshold send one or more signals to the motors corresponding to the air intake dampers to close the air intake dampers, and send one or more signals to the motors corresponding to the air discharge dampers to open the air discharge dampers; and in response to determining that the air pressure outside of the casing exceeds the air pressure inside of the air passage cavity by a second threshold send one or more signals to the motors corresponding to the air intake dampers to open the air intake dampers, and send one or more signals to the motors corresponding to the air discharge dampers to close the air discharge dampers.

Another embodiment of the second aspect further comprises a set of one or more batteries configured to provide power to the processor and the plurality of motors.

Another embodiment of the second aspect further comprises a retractable display screen; a set of one or more wireless transceivers; and a processor configured to: receive content, through the set of wireless transceivers, from one or more electronic devices external to the air breathing device; and display the content on the retractable display screen.

In an embodiment of the second aspect, the retractable display screen is configured to display content to the person wearing the air breathing device.

In another embodiment of the second aspect, the retractable display screen is one of a HUD, a LCOS, and a plurality of lenses configured to point images into eyes of the person wearing the air breathing device.

Another embodiment of the second aspect further comprises a set of one or more batteries configured to provide power to the processor, the retractable screen, and the set of wireless transceivers.

Another embodiment of the second aspect further comprises a USB port mounted on the casing, the USB port configured to connect to an external power source and provide power to the processor, the retractable screen, and the set of transceivers.

In another embodiment of the second aspect, the air breathing device comprises a fixed display screen located on the casing and positioned to be viewable by persons facing the person wearing the air breathing device. The air breathing device comprises a processor configured to receive media content and display the media content on the fixed display screen.

Another embodiment of the second aspect further comprises a camera lens directed to the mouth of the person wearing the air breathing device. The camera lens is configured to capture media content comprising one of a plurality of images and a set of one or more videos. The processor is configured to display the captured content on the fixed display screen.

Another embodiment of the second aspect further comprises a microphone configured to capture sounds spoken by the wearer of the air breathing device. The processor is configured to convert the captured sounds into simulated lip movements and display the simulated lip movements on the fixed display screen.

Another embodiment of the second aspect further comprises a flashlight and a switch to turn the flashlight on or off.

Another embodiment of the second aspect further comprises a microphone configured to capture sounds spoken by the wearer of the air breathing device and a set of one or more speakers configured to play the sounds captured by the microphone.

Another embodiment of the second aspect further comprises a replaceable air filter located inside the casing at each air intake port.

In another embodiment of the second aspect, the air breathing device comprises a set of one or more heating coils located between the air intake dampers and the air passage cavity. The air breathing device comprises a set of one or more temperature sensors configured to measure the air temperature inside the casing. The air breathing device comprises a set of one or more transceivers. The air breathing device comprises a processor configured to: receive temperature measurements from the set of temperature sensors; receive first and second temperature thresholds from an external electronic device communicatively coupled to the processor through one of the transceivers in the set of transceivers, where the second threshold is larger than the first threshold; turn on power to the set of heating coils when the temperature measurements are below the first threshold; and turn off the power to the heating coils when the temperature measurements are above the second threshold.

Another embodiment of the second aspect further comprises a USB) port mounted on the casing, the USB port configured to connect to an external power source and provide power to the set of heating coils, the processor, and the set of transceivers.

In a third aspect, an air breathing device is provided. The air breathing device comprises a casing. The air breathing device comprises an air passage cavity encompassed by the casing. The air breathing device comprises a set of one or more air intake ports. The air breathing device comprises a set of one or more air discharge ports. The air breathing device comprises an air tube connecting the air passage cavity to a mouth of a person wearing the air breathing device. The air breathing device comprises a set of one or more ultraviolet (UV) light sources inside the air passage cavity. The air breathing device comprises a first set of one or more UV light screens separating the air passage cavity from the person's mouth. The air breathing device comprises a second set of one or more UV light screens, each UV light screen in the second set of UV light screens separating the air passage cavity from one air intake port and one air discharge port.

In an embodiment of the third aspect, the UV light sources are configured to generate UV rays with a wavelength ranging between 200 nanometers to 280 nanometers.

An embodiment of the third aspect further comprises a set of one or more batteries configured to provide power to the set of UV light sources.

In a fourth aspect, an air breathing device is provided. The air breathing device comprises a casing. The air breathing device comprises an air passage cavity encompassed by the casing. The air breathing device comprises a set of one or more air intake ports. The air breathing device comprises a set of one or more air discharge ports. The air breathing device comprises an air tube connecting the air passage cavity to a mouth of a person wearing the air breathing device. The air breathing device comprises a retractable display screen. The air breathing device comprises a set of one or more wireless transceivers. The air breathing device comprises a processor configured to: receive content, through the set of wireless transceivers, from one or more electronic devices external to the air breathing device; and display the content on the retractable display screen.

In an embodiment of the fourth aspect, the retractable display screen is configured to display content to the person wearing the air breathing device.

In another embodiment of the fourth aspect, the retractable display screen is one of a HUD, a LCOS, and a plurality of lenses configured to point images into eyes of the person wearing the air breathing device.

An embodiment of the fourth aspect further comprises a set of one or more batteries configured to provide power to the processor, the retractable display screen, and the set of wireless transceivers.

In a fifth aspect, an air breathing device is provided. The air breathing device comprises a casing. The air breathing device comprises an air passage cavity encompassed by the casing. The air breathing device comprises a set of one or more air intake ports. The air breathing device comprises a set of one or more air discharge ports. The air breathing device comprises an air tube connecting the air passage cavity to a mouth of a person wearing the air breathing device. The air breathing device comprises a fixed display screen located on the casing and positioned to be viewable by persons facing the person wearing the air breathing device. The air breathing device comprises a processor configured to receive media content and display the media content on the fixed display screen.

An embodiment of the fifth aspect further comprises a camera lens directed to the mouth of the person wearing the air breathing device. The camera lens is configured to capture media content comprising one of a plurality of images and a set of one or more videos. The processor is configured to display the captured content on the fixed display screen.

Another embodiment of the fifth aspect further comprises a microphone configured to capture sounds spoken by the wearer of the air breathing device. The processor is configured to convert the captured sounds into simulated lip movements and display the simulated lip movements on the fixed display screen.

Another embodiment of the fifth aspect further comprises a set of one or more batteries configured to provide power to the processor, the fixed display screen, and the microphone.

In a sixth aspect, an air breathing device is provided. The air breathing device includes a casing, an air passage cavity encompassed by the casing. The air breathing device includes an air intake port that connects the air passage cavity to the outside of the casing through a corresponding air intake damper. The air intake damper includes several air intake damper blades and several air intake damper hinges. Each of the air intake damper blade is configured to rotate in a first direction around a corresponding hinge of the several of air intake damper hinges in response to the air pressure inside of the air passage cavity being less than the air pressure outside of the casing to open the air intake damper. Each air intake damper blade is configured to rotate in a second direction around the corresponding hinge of the several air intake damper hinges in response to the air pressure inside of the air passage cavity being more than the air pressure outside of the casing to close the air intake damper. The air breathing device includes an air discharge port that connects the air passage cavity to the outside of the casing through a corresponding air discharge damper that includes several air discharge blades and several air discharge hinges. Each air discharge damper blade is configured to rotate in a third direction around a corresponding hinge of the several air discharge damper hinges in response to the air pressure inside of the air passage cavity being more than the air pressure outside of the casing to open the air discharge damper. Each air discharge damper blade is configured to rotate in a fourth direction around the corresponding hinge of the several air discharge damper hinges in response to the air pressure inside of the air passage cavity being less than the air pressure outside of the casing to close the air discharge damper. The air breathing device includes an air tube that is configured to connect the air passage cavity to the mouth of a person wearing the air breathing device. The air breathing device includes several UV light sources inside the air passage cavity. The air breathing device includes a first UV light screen located inside the air tube. The first UV light screen is configured to separate the air passage cavity from the mouth of the person. The air breathing device includes a second UV light screen that separates the air passage cavity from the air intake port. The air breathing device includes a third UV light screen that separates the air passage cavity from air discharge port.

In an embodiment of the sixth aspect, the UV light sources are configured to generate UV rays with a wavelength ranging between 200 nanometers to 280 nanometers.

In another embodiment of the sixth aspect, at least a portion of the interior surface of the air passage cavity includes a material that is reflective to UV rays.

An embodiment of the sixth aspect further includes a switch to turn the UV light sources on or off.

Another embodiment of the sixth aspect further includes a replaceable air filter. The replaceable air filter is one of a carbon filter or a nanofiber air filter. The replaceable air filter is located inside the casing at the air intake port.

Another embodiment of the sixth aspect further includes a perforated screen at the air intake port and a perforated screen at the air discharge port.

Another embodiment of the sixth aspect further includes a retractable display screen, a wireless transceiver, and a processor. The processor is configured to receive content, through the wireless transceiver, from one or more electronic devices external to the air breathing device and display the content on the retractable display screen.

In another embodiment of the sixth aspect, the retractable display screen is configured to display content to the person wearing the air breathing device.

In another embodiment of the sixth aspect, the retractable display screen is one of a HUD, a LCOS, or several lenses that are configured to point images into eyes of the person wearing the air breathing device.

Another embodiment of the sixth aspect further includes one or more batteries configured to provide power to the processor, the retractable display screen, and the wireless transceiver.

Another embodiment of the sixth aspect further includes, a fixed display screen located on the casing and positioned to be viewable by persons facing the person wearing the air breathing device and a processor. The processor is configured to receive media content and display the media content on the fixed display screen.

Another embodiment of the sixth aspect further includes a camera lens that is configured to be directed to the mouth of the person wearing the air breathing device. The camera lens is configured to capture media content that includes images of the mouth of the person or a video of the mouth of the person. The processor is configured to display the captured content on the fixed display screen.

Another embodiment of the sixth aspect further includes a microphone that is configured to capture sounds spoken by the wearer of the air breathing device. The processor is configured to convert the captured sounds into simulated lip movements and display the simulated lip movements on the fixed display screen.

Another embodiment of the sixth aspect further includes a flashlight and a switch to turn the flashlight on or off.

Another embodiment of the sixth aspect further includes a microphone that is configured to capture sounds spoken by the wearer of the air breathing device and one or more speaker configured to play the sounds captured by the microphone.

Another embodiment of the sixth aspect further includes a heating coil located between the air intake damper and the air passage cavity, a temperature sensor that is configured to measure the air temperature inside the casing, a transceiver, and a processor. The processor is configured to receive temperature measurements from the temperature sensor, receive first and second temperature thresholds from an external electronic device communicatively coupled to the processor through the transceiver, where the second threshold is larger than the first threshold. The processor is configured to turn on power to the heating coil when the temperature measurements are below the first threshold and turn off the power to the heating coil when the temperature measurements are above the second the threshold.

Another embodiment of the sixth aspect further includes a USB port mounted on the casing. The USB port is configured to connect to an external power source and provide power to the heating coil, the transceiver, the processor, and the UV light sources.

Another embodiment of the sixth aspect further includes a processor, first and second motors, and an air pressure differential sensor. The first motor corresponds to the air intake damper and second motor corresponds to the air discharge damper. The first and second motors are configured to receive one or more signals and in response to receiving the signals open or close the corresponding damper. The air pressure differential sensor is configured to measure a difference between the air pressure inside of the air passage cavity and the air pressure outside of the casing. The processor is configured to receive the air pressure differential readings from the air pressure differential sensor, in response to determining that the air pressure inside of the air passage cavity exceeds the air pressure outside of the casing by a first threshold, send one or more signals to the first motor to close the air intake damper, and send one or more signals to the second motor to open the air discharge damper. The processor is configured to, in response to determining that the air pressure outside of the casing exceeds the air pressure inside of the air passage cavity by a second threshold, send one or more signals to the first motor to open the air intake damper, and send one or more signals to the second motor to close the air discharge damper.

In another embodiment of the sixth aspect, the air intake damper is a gravity damper configured to open when the air pressure inside of the air passage cavity is less than the air pressure outside of the casing and close when the air pressure inside of the air passage cavity is more than the air pressure outside of the casing. The air discharge damper is a gravity damper configured to close when the air pressure inside of the air passage cavity is less than the air pressure outside of the casing and open when the air pressure inside of the air passage cavity is more than the air pressure outside of the casing.

Another embodiment of the sixth aspect further includes a detachable display screen located on the casing, a wireless transceiver, and a processor. The processor is configured to receive content, through the wireless transceiver, from one or more electronic devices external to the air breathing device and display the content on the retractable display screen.

In a seventh aspect, an air breathing device is provided. The air breathing device includes a casing and an air passage cavity encompassed by the casing. The air breathing device includes an air intake port that connects the air passage cavity to the outside of the casing through a corresponding air intake damper that includes several air intake damper blades and several air intake damper hinges. Each air intake damper blade is configured to rotate in a first direction around a corresponding hinge of the several air intake damper hinges in response to the air pressure inside of the air passage cavity being less than the air pressure outside of the casing to open the air intake damper. Each air intake damper blade is configured to rotate in a second direction around the corresponding hinge of the several air intake damper hinges in response to the air pressure inside of the air passage cavity being more than the air pressure outside of the casing to close the air intake damper. The air breathing device includes an air discharge port that connects the air passage cavity to the outside of the casing through a corresponding air discharge damper that includes several air discharge blades and several air discharge hinges. Each air discharge damper blade is configured to rotate in a third direction around a corresponding hinge of the several air discharge damper hinges in response to the air pressure inside of the air passage cavity being more than the air pressure outside of the casing to open the air discharge damper. Each air discharge damper blade is configured to rotate in a fourth direction around the corresponding hinge of the several air discharge damper hinges in response to the air pressure inside of the air passage cavity being less than the air pressure outside of the casing to close the air discharge damper. The air breathing device includes an air tube that is configured to connect the air passage cavity to the mouth of a person wearing the air breathing device.

An embodiment of the seventh aspect further includes a processor, first and second motors, and an air pressure differential sensor. The first motor corresponds to the air intake damper and the second motor corresponds to the air discharge damper. The first and second motors are configured to receive one or more signals and in response to receiving the signals open or close the corresponding damper. The air pressure differential sensor is configured to measure a difference between the air pressure inside of the air passage cavity and the air pressure outside of the casing. The processor is configured to receive the air pressure differential readings from the air pressure differential sensor, in response to determining that the air pressure inside of the air passage cavity exceeds the air pressure outside of the casing by a first threshold, send one or more signals to the first motor to close the air intake damper, and send one or more signals to the second motor to open the air discharge damper. The processor is configured to, in response to determining that the air pressure outside of the casing exceeds the air pressure inside of the air passage cavity by a second threshold, send one or more signals to the first motor to open the air intake damper, and send one or more signals to the second motor to close the air discharge damper.

Another embodiment of the seventh aspect further includes a retractable display screen, a wireless transceiver, and a processor. The processor is configured to receive content, through the wireless transceiver, from one or more electronic devices external to the air breathing device and display the content on the retractable display screen.

In an embodiment of the seventh aspect, the retractable display screen is one of HUD, a LCOS, and several lenses that are configured to point images into eyes of the person wearing the air breathing device.

Another embodiment of the seventh aspect further includes one or more batteries configured to provide power to the processor, the retractable display screen, and the wireless transceiver.

Another embodiment of the seventh aspect further includes a fixed display screen and a processor. The fixed display screen is located on the casing and positioned to be viewable by persons facing the person wearing the air breathing device. The processor is configured to receive media content and display the media content on the fixed display screen.

Another embodiment of the seventh aspect further includes a camera lens configured to be directed to the mouth of the person wearing the air breathing device. The camera lens is configured to capture media content that includes images of the mouth of the person or a video of the mouth of the person. The processor is configured to display the captured content on the fixed display screen.

Another embodiment of the seventh aspect further includes a microphone that is configured to capture sounds spoken by the wearer of the air breathing device. The processor is configured to convert the captured sounds into simulated lip movements and display the simulated lip movements on the fixed display screen.

Another embodiment of the seventh aspect further includes a flashlight and a switch to turn the flashlight on or off.

Another embodiment of the seventh aspect further includes a microphone that is configured to capture sounds spoken by the wearer of the air breathing device and one or more speakers that are configured to play the sounds captured by the microphone.

Another embodiment of the seventh aspect further includes a replaceable air filter that includes a carbon filter or a nanofiber air filter, located inside the casing at the air intake port.

Another embodiment of the seventh aspect further includes a heating coil located between the air intake damper and the air passage cavity, a temperature sensor configured to measure the air temperature inside the casing, a transceiver, and a processor. The processor is configured to receive temperature measurements from the temperature sensor, receive first and second temperature thresholds from an external electronic device that is communicatively coupled to the processor through the transceiver, where the second threshold is larger than the first threshold. The processor is configured to turn on power to the heating coil when the temperature measurements are below the first threshold and turn off the power to the heating coil when the temperature measurements are above the second the threshold.

Another embodiment of the seventh aspect further includes a USB port mounted on the casing. The USB port is configured to connect to an external power source and provide power to the heating coil, the processor, and the transceiver.

In another embodiment of the seventh aspect, the air intake damper is a gravity damper configured to open when the air pressure inside of the air passage cavity is less than the air pressure outside of the casing and close when the air pressure inside of the air passage cavity is more than the air pressure outside of the casing. The air discharge damper is a gravity damper configured to close when the air pressure inside of the air passage cavity is less than the air pressure outside of the casing and open when the air pressure inside of the air passage cavity is more than the air pressure outside of the casing.

Another embodiment of the seventh aspect further includes a detachable display screen located on the casing, a wireless transceiver, and a processor. The processor is configured to receive content, through the wireless transceiver, from one or more electronic devices external to the air breathing device and display the content on the retractable display screen.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure.

What is claimed is:

1. A half-face air breathing device, comprising:
    an air intake port;
    an air discharge port;
    a retractable display screen;
    a casing;
    a facepiece connected to the casing, the facepiece is configured to form an airtight seal against a face of a person wearing the half-face air breathing device to engage a mouth and a nose of the person wearing the half-face air breathing device in a sealing manner, the facepiece is configured to allow fluid communication between the nose and the mouth with the air intake port and the air discharge port, the casing comprising a harness handle configured to be attached to a head strap for securing the half-face air breathing device to a head of the person wearing the half-face air breathing device,
    the casing comprising a screen housing for housing the retractable display screen,
        wherein the screen housing comprises a front face and an upper elongated opening,
        wherein the upper elongated opening is configured to allow the retractable display screen to retract through, and be stored within, an interior of the screen housing when the retractable display screen is not being used, wherein the retractable display screen in a retracted position, is configured to be hidden behind the front face of the screen housing, wherein the upper elongated opening is configured to allow the retractable display screen to extend through when the retractable display screen is in use, and wherein the retractable display screen in a fully extended position is configured to be positioned in front of both eyes of the person wearing the half-face air breathing device and to be above the upper elongated opening relative to a vertical height of the person wearing the half-face air breathing device, a wireless receiver; and a processor configured to:
  receive content, through the wireless receiver, from one or more electronic devices external to the half-face air breathing device; and
  display the content on the retractable display screen.

2. The half-face air breathing device of claim 1, wherein the retractable display screen comprises a transparent display.

3. The half-face air breathing device of claim 1, wherein the retractable display screen is a head-up display (HUD).

4. The half-face air breathing device of claim 1, wherein the retractable display screen is a Liquid Crystal on Silicon (LCOS).

5. The half-face air breathing device of claim 1, wherein the retractable display screen is configured to have an adjustable opacity.

6. The half-face air breathing device of claim 5, wherein the retractable display screen comprises polymer dispersed liquid crystal (PDLC).

7. The half-face air breathing device of claim 6, wherein the retractable display screen comprises two layers of transparent conductive indium tin oxide (ITO) films with PDLC between the two layers.

8. The half-face air breathing device of claim 5 further comprising a switch or a knob for controlling the opacity of the retractable display screen.

9. The half-face air breathing device of claim 1 further comprising one or more batteries configured to provide power to the processor, the retractable display screen, and the wireless receiver.

10. The half-face air breathing device of claim 1, wherein the half-face air breathing device is configured to receive power from a power source external to the half-face air breathing device to provide power to the processor, the retractable display screen, and the wireless receiver.

11. The half-face air breathing device of claim 1, wherein the retractable display screen comprises a plurality of lenses configured to point images into eyes of the person wearing the half-face air breathing device.

12. The half-face air breathing device of claim 1, wherein the retractable display screen is configured to display content to the person wearing the half-face air breathing device.

13. The half-face air breathing device of claim 1, wherein the retractable display screen is configured to extend to an eye level of the person wearing the half-face air breathing device.

14. The half-face air breathing device of claim 1, wherein the retractable display screen is a curved display screen.

15. The half-face air breathing device of claim 1, wherein the retractable display screen is a flat display screen.

16. The half-face air breathing device of claim 1 further comprising:
  a rear facing camera positioned on the harness, wherein the retractable display screen is configured to display images captured by the rear facing camera.

17. The half-face air breathing device of claim 1 further comprising a fixed display screen.

18. The half-face air breathing device of claim 17, wherein the fixed display screen is a liquid crystal display (LCD) screen.

19. The half-face air breathing device of claim 17, wherein the fixed display screen is configured to display information to people other than the person wearing the half-face air breathing device.

20. The half-face air breathing device of claim 17, wherein the fixed display screen is located on an outside surface of the casing opposite to a face of the person that is wearing the half-face air breathing device.

21. The half-face air breathing device of claim 17 further comprising a camera configured to point to lips of the person wearing the half-face air breathing device, wherein:
  the camera is configured to capture video from movements of the lips of the person wearing the half-face air breathing device;
  the processor is configured to display the video captured by the camera on the fixed display.

22. The half-face air breathing device of claim 17, wherein the processor is configured to display one or more: text messages, emojis, augmented reality, or multimedia content on the fixed display screen.

23. The half-face air breathing device of claim 22, wherein the processor is configured to receive said one or more: text messages, emojis, augmented reality, or multimedia content from the one or more electronic devices external to the half-face air breathing device.

* * * * *